United States Patent
Hopfner et al.

(10) Patent No.: US 11,229,700 B2
(45) Date of Patent: Jan. 25, 2022

(54) TRISPECIFIC MOLECULE COMBINING SPECIFIC TUMOR TARGETING AND LOCAL IMMUNE CHECKPOINT INHIBITION

(71) Applicant: Ludwig-Maximilians-Universität München, Munich (DE)

(72) Inventors: Karl-Peter Hopfner, Berg (DE); Marion Subklewe, Munich (DE); Nadine Magauer, Innsbruck (AT); Nadja Fenn, Achmühle (DE)

(73) Assignee: LUDWIG-MAXIMILIANS-UNIVERSITÄT MÜNCHEN, Munich (DE)

(*) Notice: Subject to any disclaimer, the term of this patent is extended or adjusted under 35 U.S.C. 154(b) by 0 days.

(21) Appl. No.: 15/764,788

(22) PCT Filed: Nov. 9, 2016

(86) PCT No.: PCT/EP2016/077174
§ 371 (c)(1),
(2) Date: Mar. 29, 2018

(87) PCT Pub. No.: WO2017/081101
PCT Pub. Date: May 18, 2017

(65) Prior Publication Data
US 2018/0311348 A1 Nov. 1, 2018

(30) Foreign Application Priority Data
Nov. 9, 2015 (EP) .................................. 15193711

(51) Int. Cl.
| C07K 14/705 | (2006.01) |
| A61K 39/395 | (2006.01) |
| C07K 16/28 | (2006.01) |
| A61P 35/02 | (2006.01) |
| A61K 48/00 | (2006.01) |
| C07K 19/00 | (2006.01) |

(52) U.S. Cl.
CPC .... *A61K 39/39541* (2013.01); *A61K 39/3955* (2013.01); *A61K 39/39558* (2013.01); *A61K 39/39566* (2013.01); *A61K 48/005* (2013.01); *A61P 35/02* (2018.01); *C07K 14/705* (2013.01); *C07K 16/2803* (2013.01); *C07K 16/283* (2013.01); *C07K 16/2809* (2013.01); *C07K 16/2878* (2013.01); *C07K 16/2887* (2013.01); *C07K 19/00* (2013.01); *C07K 2317/31* (2013.01); *C07K 2317/622* (2013.01); *C07K 2317/92* (2013.01); *C07K 2319/00* (2013.01); *C07K 2319/33* (2013.01)

(58) Field of Classification Search
CPC .............. C07K 2317/31; C07K 16/283; C07K 16/2803; C07K 14/705
USPC ............................................ 424/133.1, 136.1
See application file for complete search history.

(56) References Cited

U.S. PATENT DOCUMENTS

| 2012/0251531 A1 | 10/2012 | Baehner et al. |
| 2015/0132217 A1 | 5/2015 | Chang et al. |
| 2019/0127465 A1* | 5/2019 | Zugmaier .......... C07K 16/2803 |
| 2019/0359710 A1* | 11/2019 | Fey ..................... C07K 16/2866 |

OTHER PUBLICATIONS

Braciak et al. (Oncoimmunology. Jul. 30, 2018;7(9):e1472195).*
Chatzopoulou et al. (Analyst, 2016, 141, 2284-2295).*
Kugler et al. (British Journal of Haematology, 150, 574-586 (Sep. 2010); published online Jul. 16, 2010).*
Braciak et al. (Journal of Translational Medicine 2013, 11:289).*
Schubert et al. (MAbs. Jan.-Feb. 2011;3(1):21-30. Epub Jan. 1, 2011).*
Coustan-Smith et al. (JCI Insight. May 3, 2018;3(9). pii: 98561. doi: 10.1172/jci.insight.98561).*
Majeti (Oncogene (2011) 30, 1009-1019).*
Liu et al (Life Sciences 122 (2015) 59-64).*
Chen et al (Adv Drug Deliv Rev. Oct. 15, 2013; 65(10): 1357-1369).*
Marvin et al. (Acta Pharmacologica Sinica Jun. 2005; 26 (6): 649-658).*
Stingaciu et al (Sci. Rep. 6, 22148; doi: 10.1038/srep22148 (2016)).*
Worn et al (J. Molec. Biol. 305:9891010 (2001)).*
USPTO BCPC, Kolker (Antibodies and the written description requirement of 35 U.S.C.112(a); pp. 1-36 (Sep. 17, 2020).*
Barclay, A.N., "Signal regulatory protein alpha (SIRPα)/CD47 interaction and function." Current Opinion in Immunology, 2009, 21: 47-52.
Braster, R et al., "Myeloid cells as effector cells for monoclonal antibody therapy of cancer." Methods, 2014, 65: 28-37.
Kügler, M et al., "A recombinant trispecific single-chain Fv derivative directed against CD123 and CD33 mediates effective elimination of acute myeloid leukaemia cells by dual targeting." British Journal of Haematology, Jul. 2010, 150: 574-586.
Osada, T. et al., "CEA/CD3-bispecific T cell-engaging (BiTE) antibody-mediated T lymphocyte cytotoxicity maximized by inhibition of both PD1 and PD-L1" Cancer Immunol. Immunother., 2015, 64: 677-688.
Roskopf, C.C. et al., "T cell-recruiting triplebody 19-3-19 mediates serial lysis of malignant B-lymphoid cells by a single T cell." Oncotarget, Jul. 2014, 5(15): 6466-6483.

(Continued)

*Primary Examiner* — Lynn A Bristol
(74) *Attorney, Agent, or Firm* — Saliwanchik, Lloyd & Eisenschenk

(57) ABSTRACT

The present invention relates to a novel molecule comprising three binding sites with specificity for a tumor cell, for an effector cell and for a checkpoint molecule, respectively. Moreover, the present invention relates to a pharmaceutical composition comprising such a molecule and to uses of such a molecule.

10 Claims, 39 Drawing Sheets

Figure 3C:
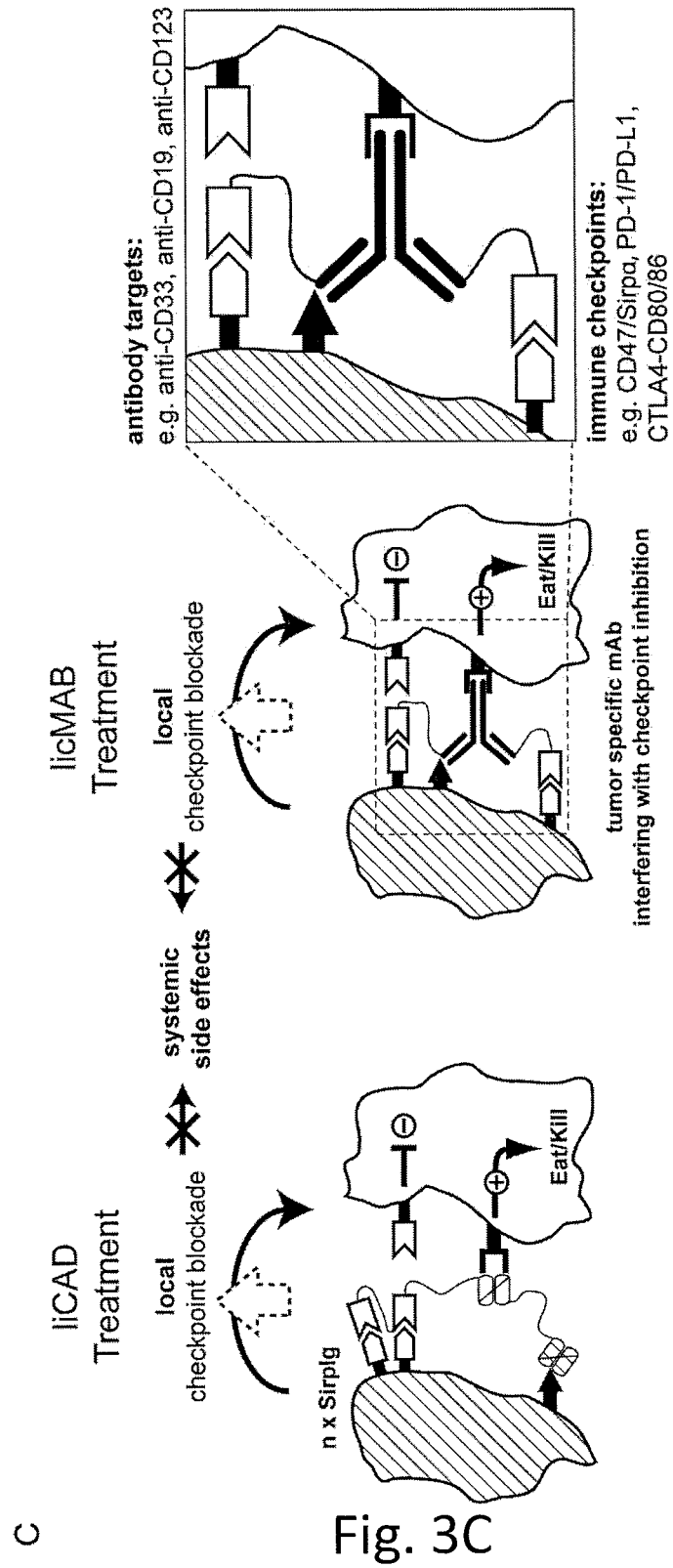

Specification includes a Sequence Listing.

(56) References Cited

OTHER PUBLICATIONS

Schubert, I. et al., "A dual-targeting triplebody mediates preferential redirected lysis of antigen double-positive over single-positive leukemic cells." Landes Bioscience, 2014, 6(1): 286-296.
Schubert, I. et al., "A single-chain triplebody with specificity for CD19 and CD33 mediates effective lysis of mixed lineage leukemia cells by dual targeting." Landes Bioscience, 2011, 3(1): 21-30.
Somasundaram, C. et al., "Development of a trispecific antibody conjugate that directs two distinct tumor-associated antigens to CD64 on myeloid effector cells." Human Antibodies, 1999, 9: 47-54.
Wang, X. et al., "A New Recombinant Single Chain Trispecific Antibody Recruits T Lymphocytes to Kill CEA (Carcinoma Embryonic Antigen) Positive Tumor Cells In Vitro Efficiently." J. Biochem., 2004, 135: 555-565.
Murata, Yoji et al. "The CD47-SIRPα signalling system: its physiological roles and therapeutic application," Journal of Biochemistry 155(6):335-344, Jun. 1, 2014.
Piccione, Emily C. et al. "A bispecific antibody targeting CD47 and CD20 selectively binds and eliminates dual antigen expressing lymphoma cells," MABS 7(5):946-956, Jun. 17, 2015.
Ponce, Laia Pascual et al. "SIRPα-antibody fusion proteins stimulate phagocytosis and promote elimination of acute myeloid leukemia cells," Oncotarget 8(7):11284-11301, Feb. 14, 2017.
European Search Report issued in the parallel European divisional Application No. 20165971.1.

\* cited by examiner

A
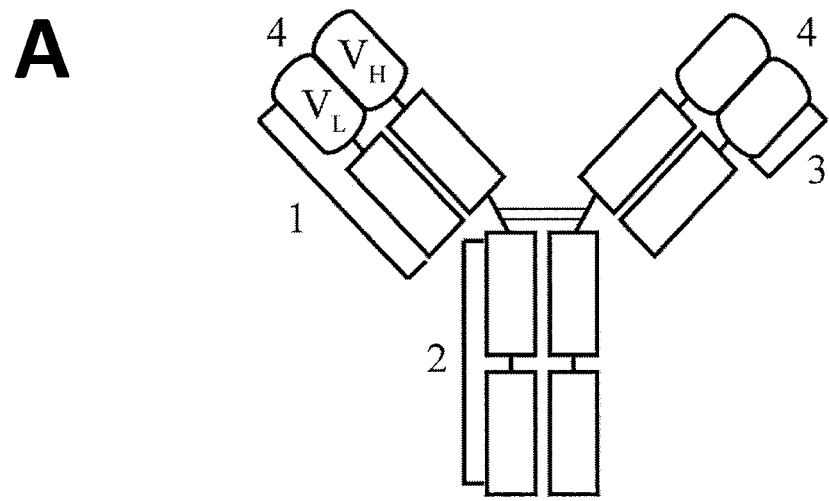
B
C
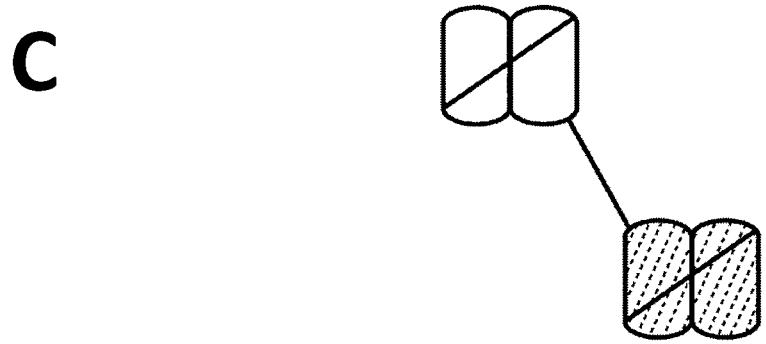
Fig. 1

A
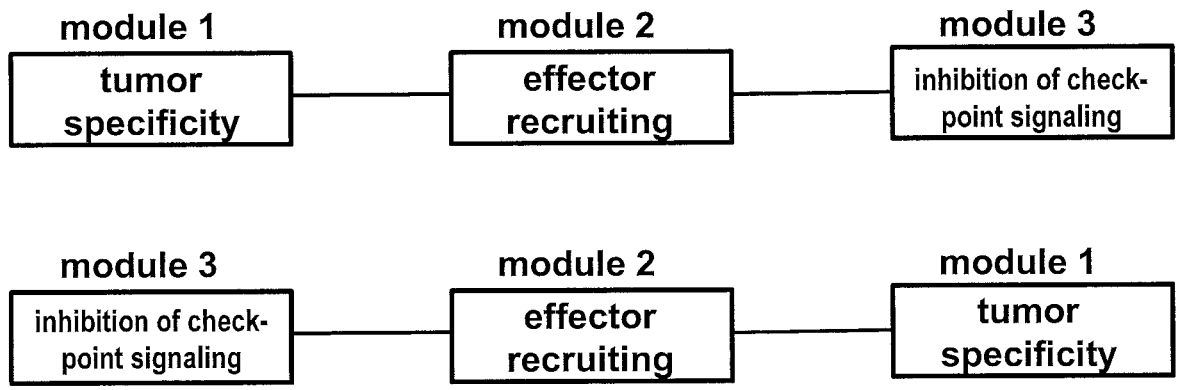
B
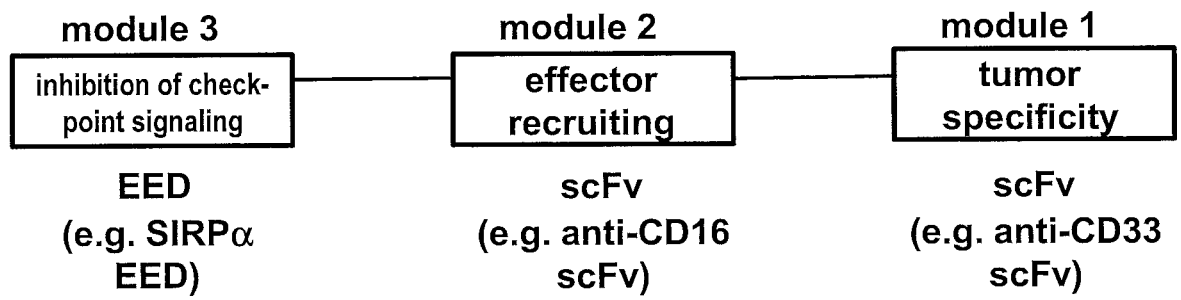
Fig. 2

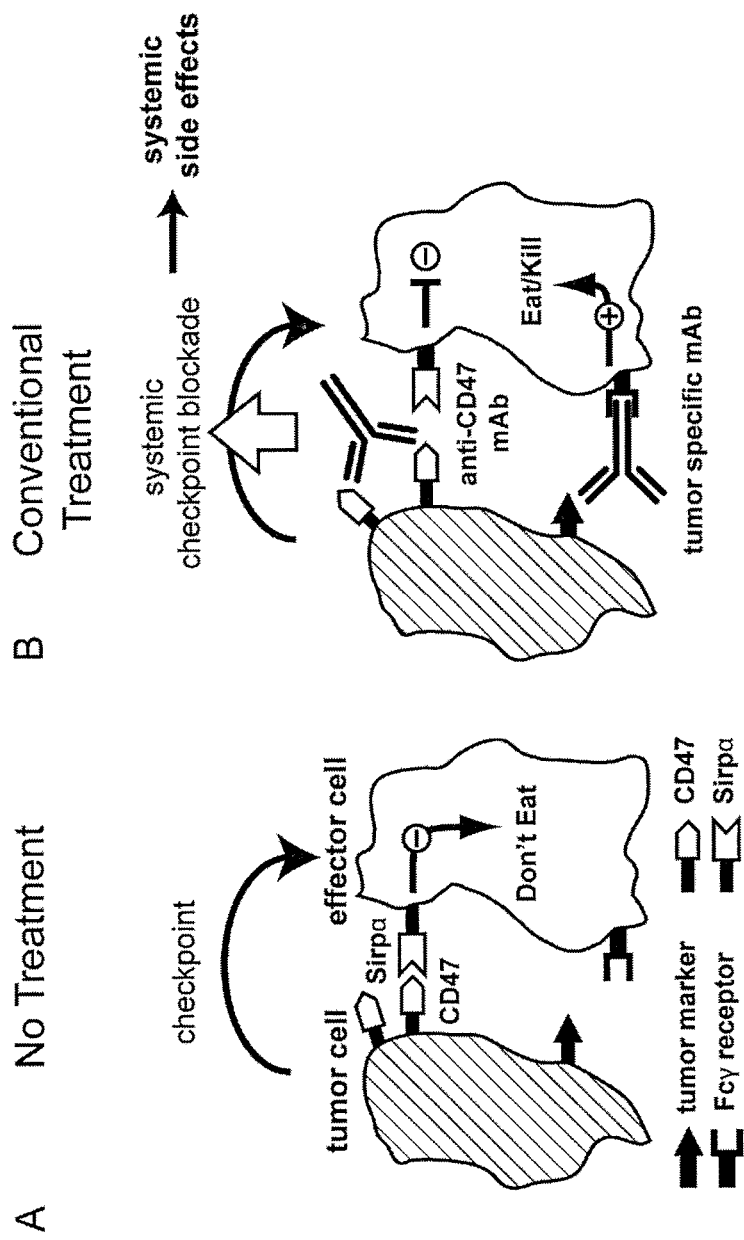
Fig. 3A, B

Binding of SirpIg to CHO.exCD47 cells
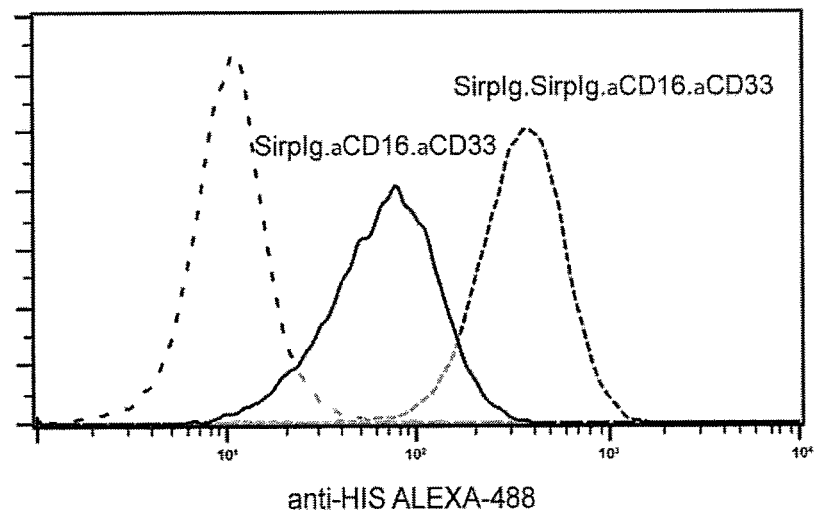
$K_D$ determination studies
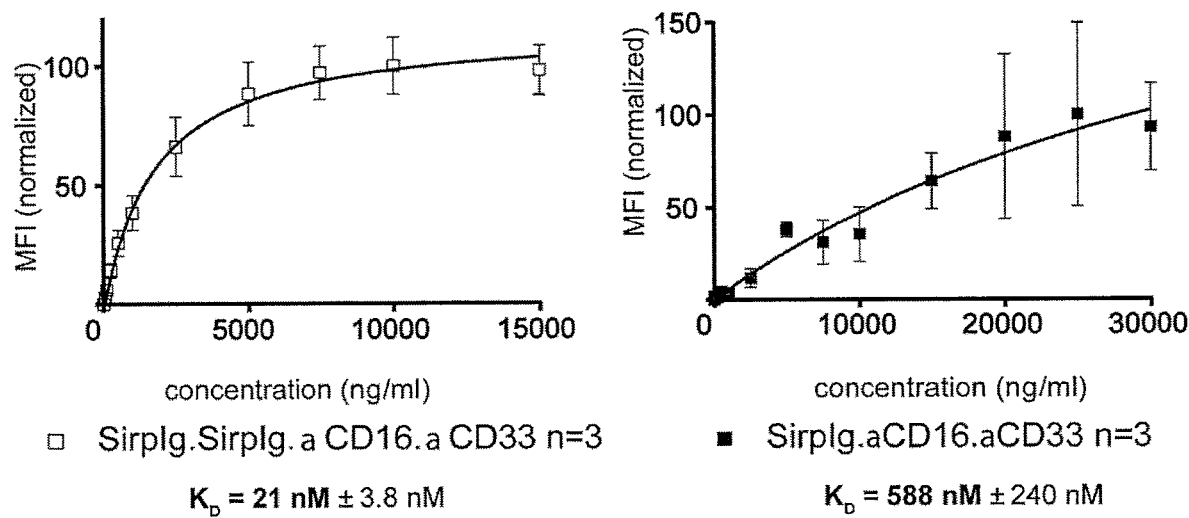
□ SirpIg.SirpIg.aCD16.aCD33 n=3
$K_D$ = 21 nM ± 3.8 nM
■ SirpIg.aCD16.aCD33 n=3
$K_D$ = 588 nM ± 240 nM
Fig. 6A Binding of CD33 to CHO.exCD33 cells
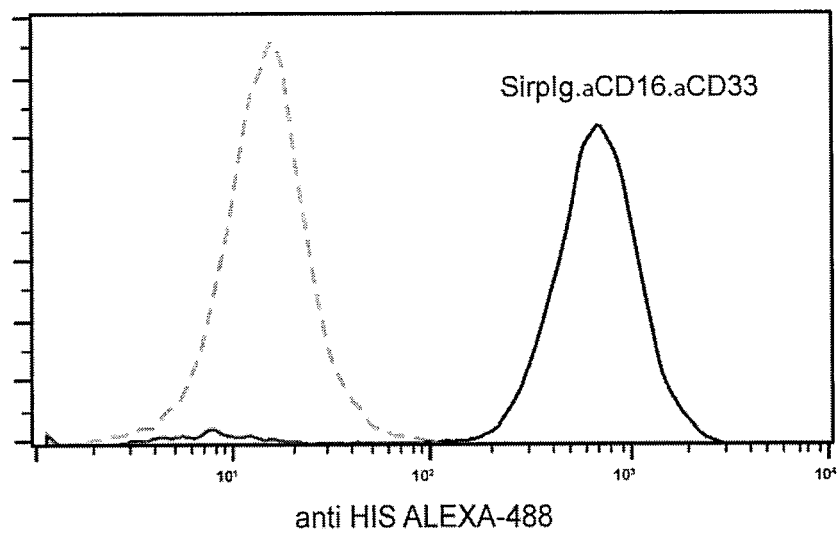
anti HIS ALEXA-488
$K_D$ determination studies
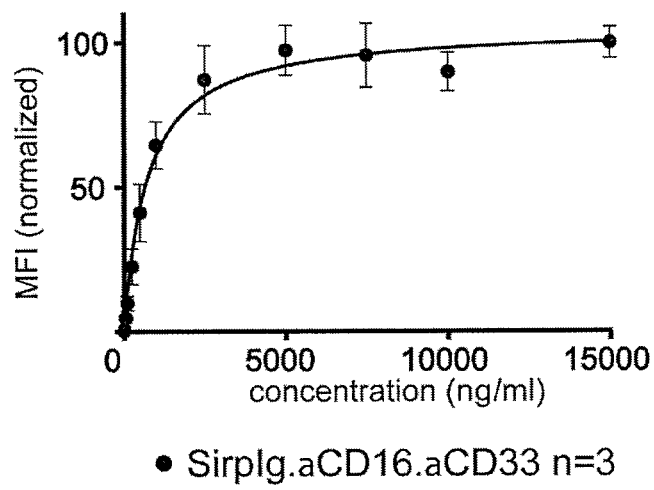
● SirpIg.aCD16.aCD33 n=3
$K_D$ = 9.8 nM ± 2.6 nM
Fig. 6B

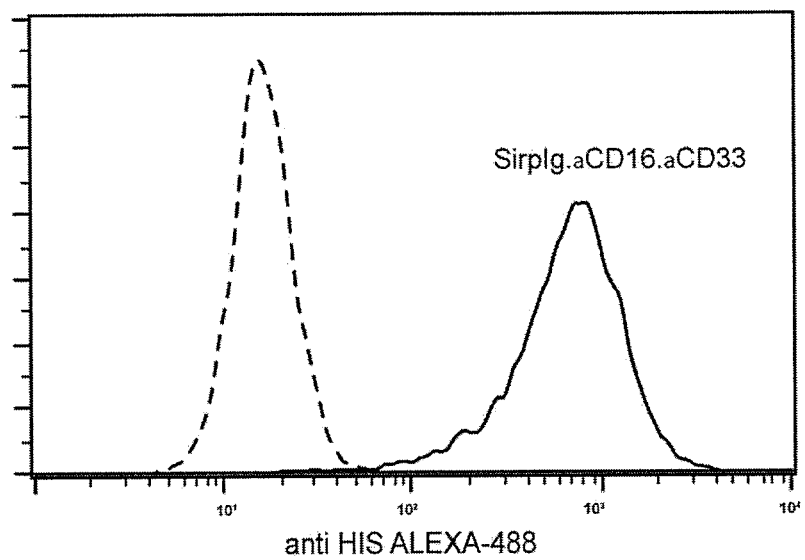
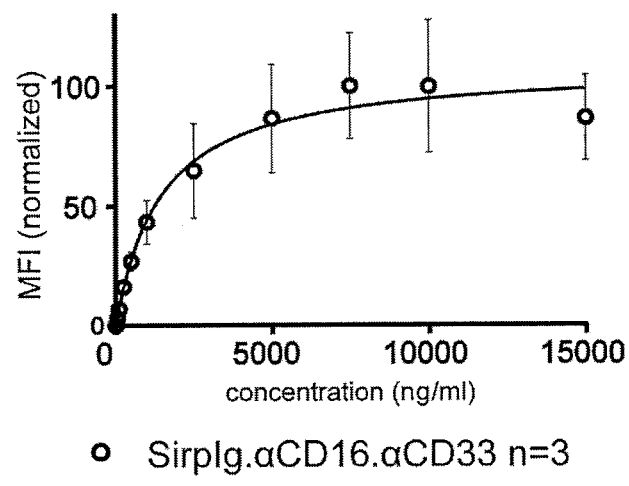
Fig. 6C

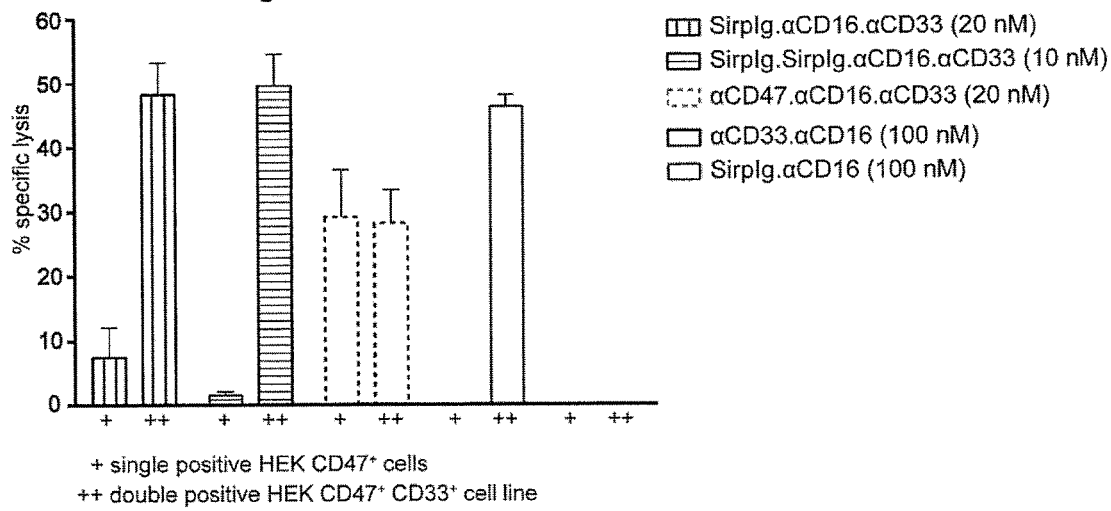
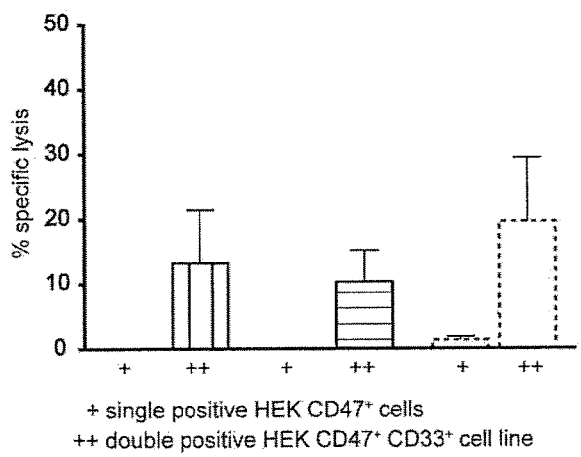
Fig. 7B, C

| | Molecule | Tm | Binding to CD16 (SEC) | K_D MOLM-13 | Internalization (120min) | ADCC (EC$_{50}$) | ADCP (100 nM) |
|---|---|---|---|---|---|---|---|
|  | αCD33 mAb | 68.4 °C | - | 3 nM | 50% | 29 pM | 55% |
|  | SirpIg.αCD33 licMAB | 67.2 °C | - | 6 nM | 68% | 23 pM | 80% |
|  | SirpIg.SirpIg.αCD33 licMAB | 66.5 °C | - | 14 nM | 56% | 34 pM | 95% |
|  | αCD33 Fc-eng. mAb | 49.7 °C / 70 °C | + | 2 nM | 60% | 7 pM | n.d. |
|  | SirpIg.αCD33 Fc-eng. licMAB | 50.0 °C / 69.0 °C | + | 4 nM | 67% | 2 pM | n.d. |
|  | SirpIg.SirpIg.αCD33 Fc-eng. licMAB | 48.3 °C / 68.8 °C | + | 9 nM | 64% | 3 pM | n.d. |
|  | SirpIg.αCD33 bispecific licMAB | 65 °C | - | 7 nM | 8% | 135 pM | n.d. |
|  | SirpIg.SirpIg.αCD33 bispecific licMAB | 64.5 °C | n.d. | 9 nM | n.d. | 192 pM | n.d. |
|  | SirpIg.αCD16.αCD33 licAD | 51 °C | n.d. | 19 nM | n.d. | 22 pM | 48% |
|  | SirpIg.SirpIg.αCD16.αCD33 licAD | 51.5 °C | n.d. | 30 nM | 14% | 1.5 pM | 54% |
|  | αCD47.αCD16.αCD33 triplebody | n.d. | n.d. | 16 nM | n.d. | 8 pM | n.d. |
|  | SirpIg.αCD33 bispecific Fc-eng. licMAB | | | Under development | | | |
|  | SirpIg.SirpIg.αCD33 bispecific Fc-eng. licMAB | | | Under development | | | |

Fig. 10

A
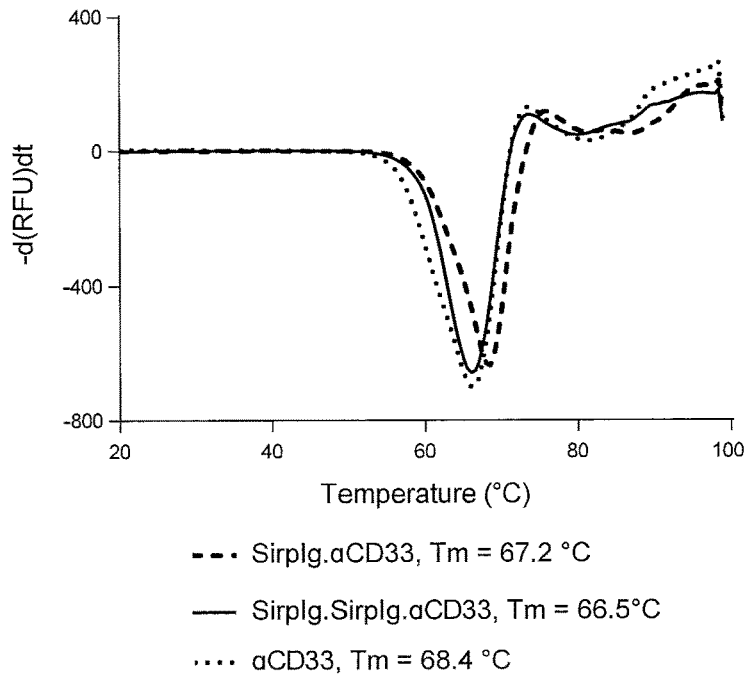
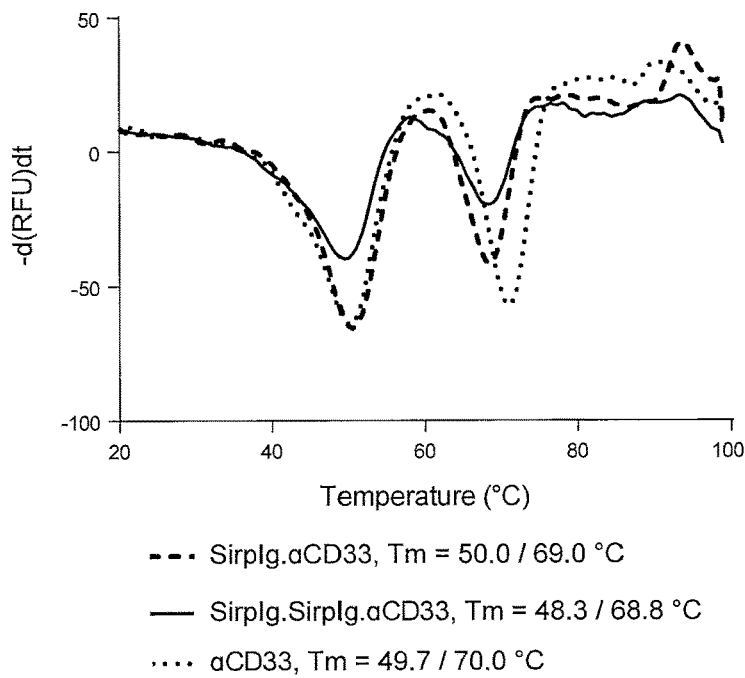
Fig. 11A

B
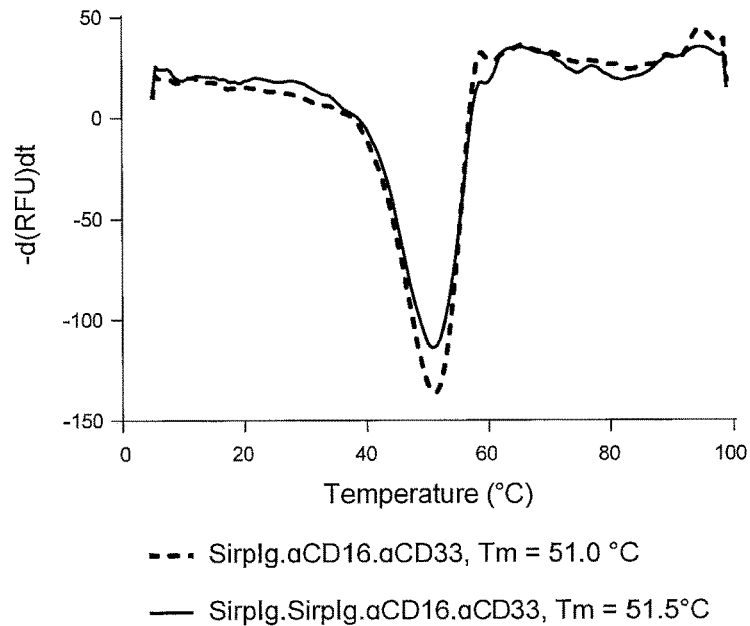
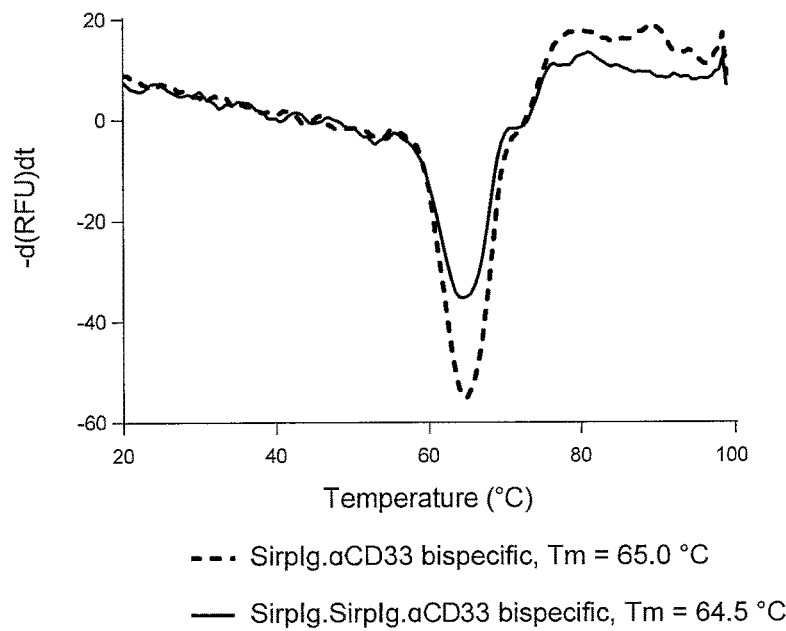
Fig. 11B

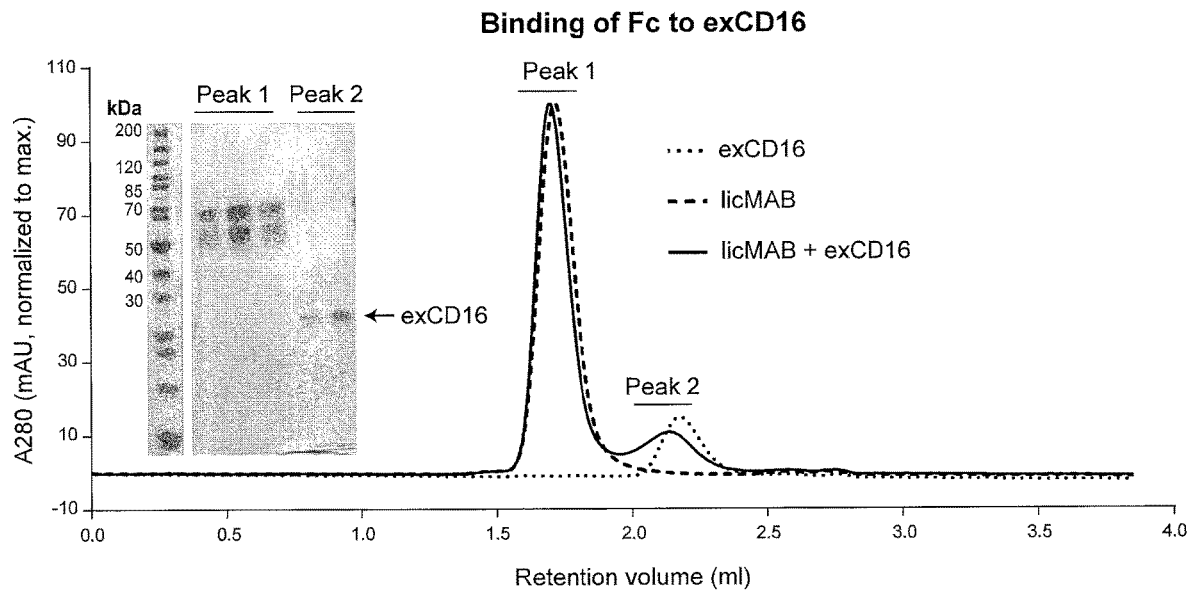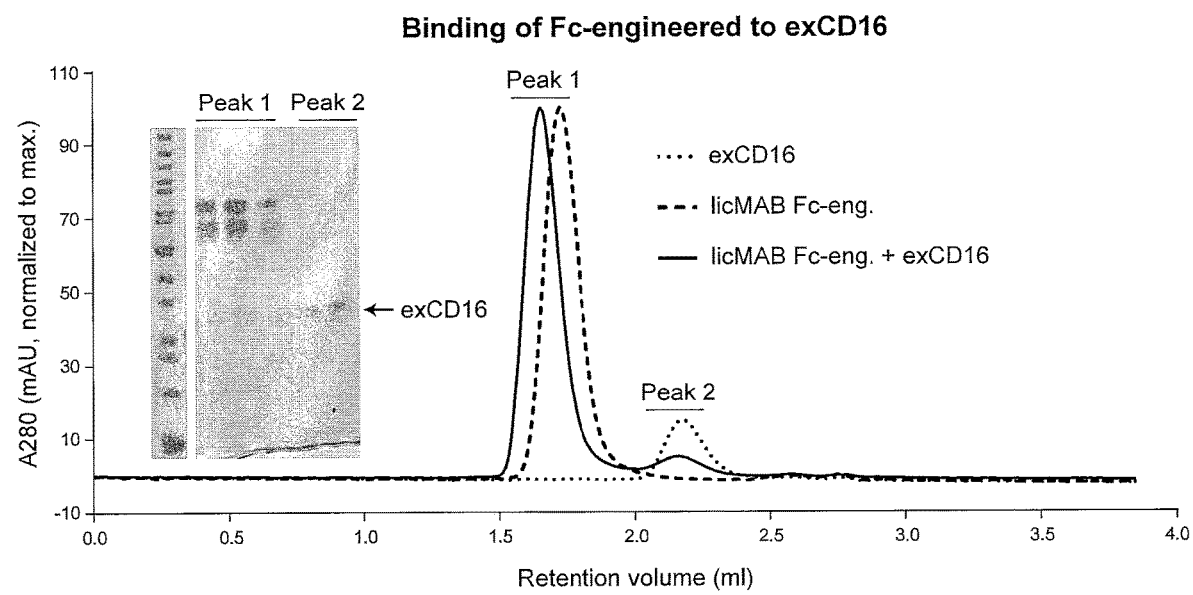
Fig. 12

A
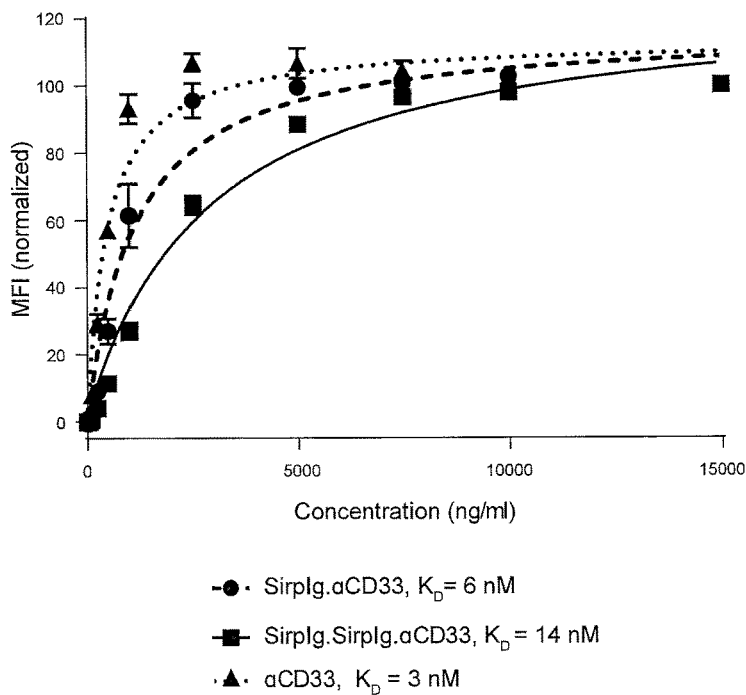
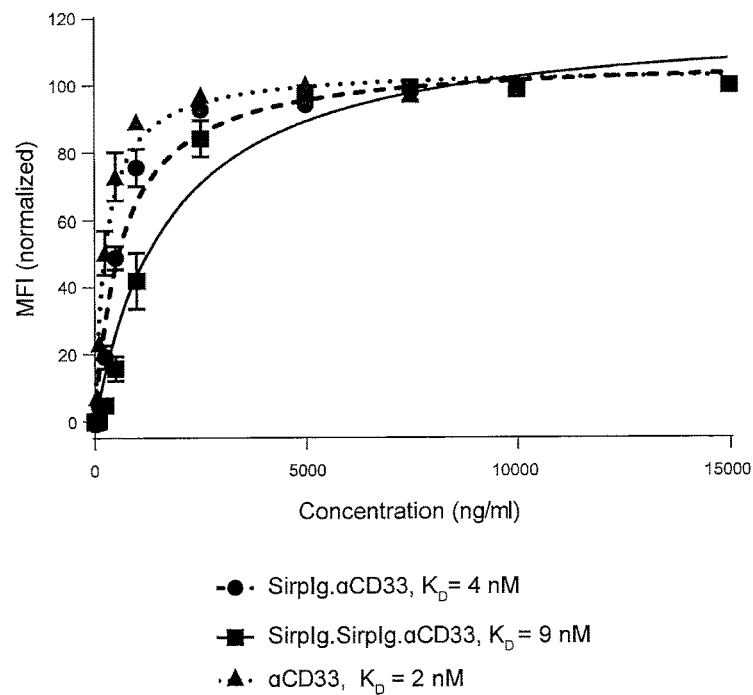
Fig. 13A

B
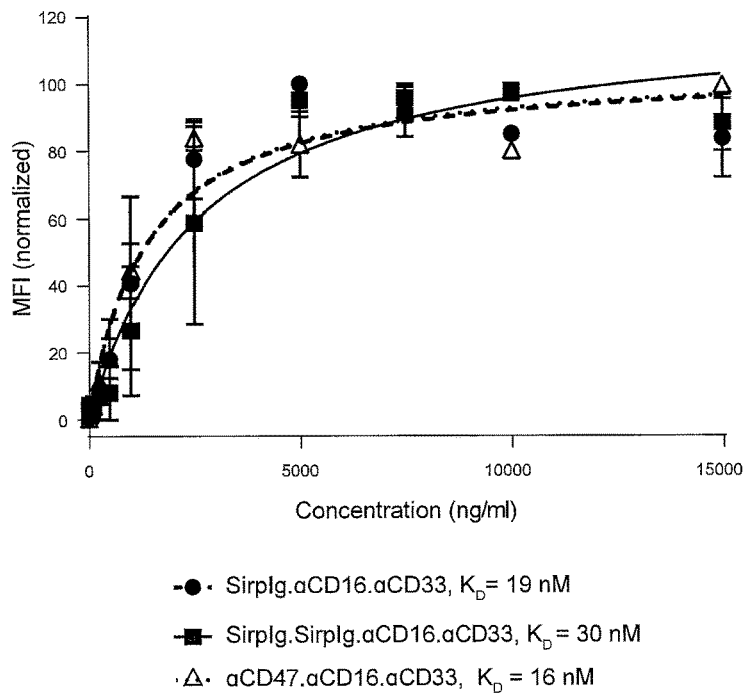
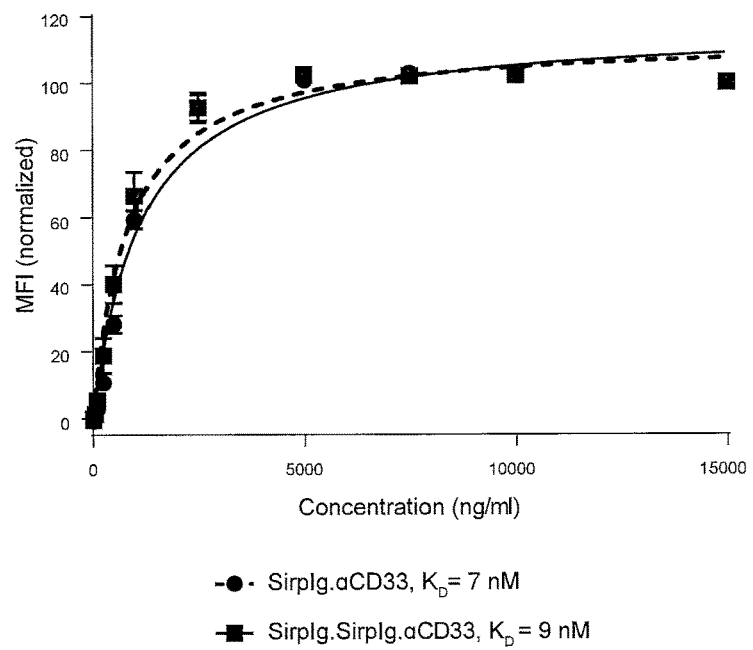
Fig. 13B

ADCC of licMABs
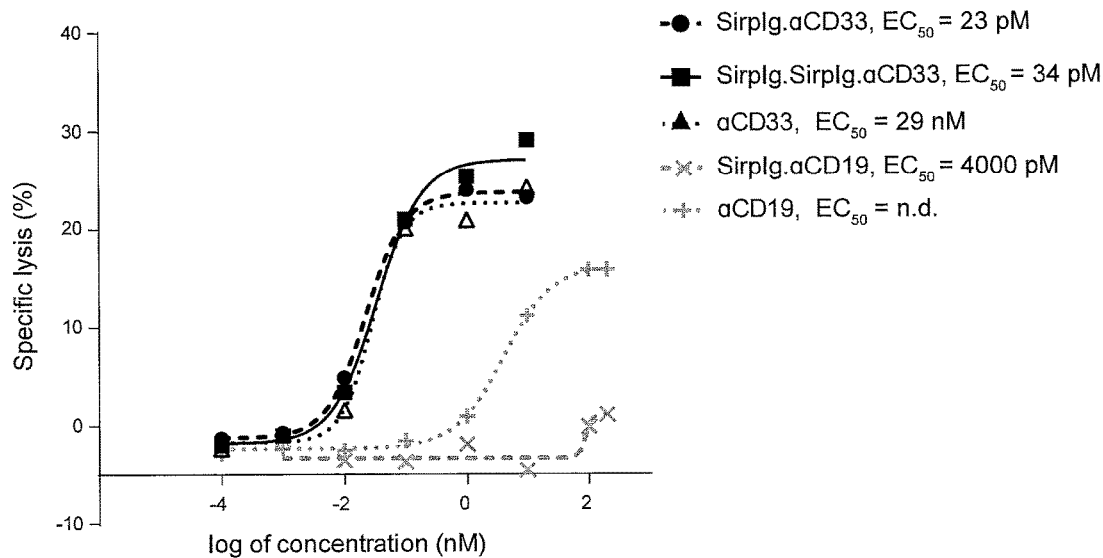
ADCC of Fc-engineered licMABs
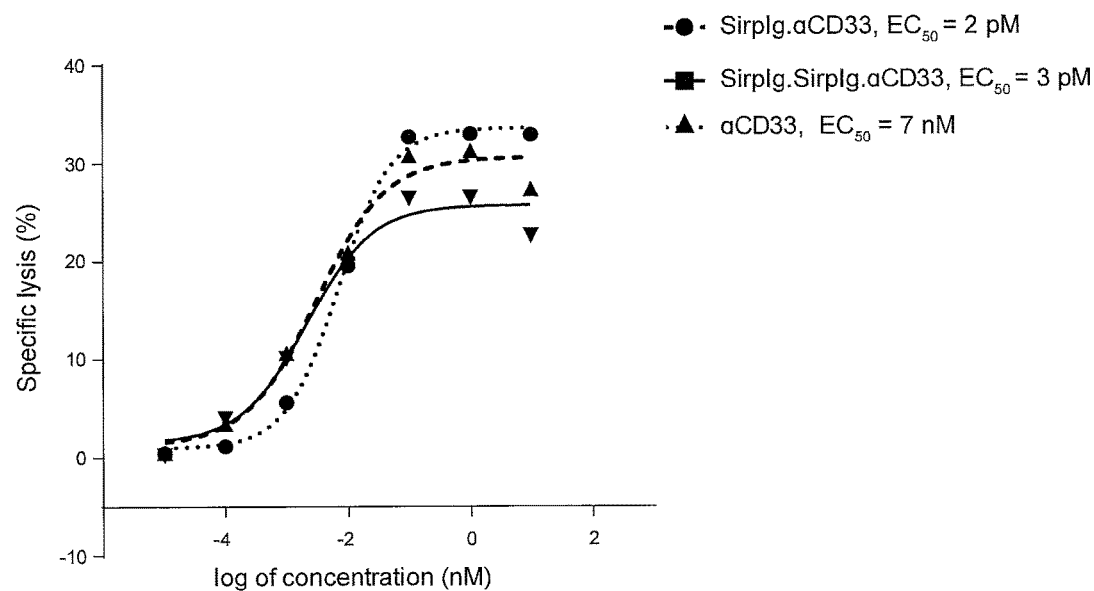
Fig. 15A

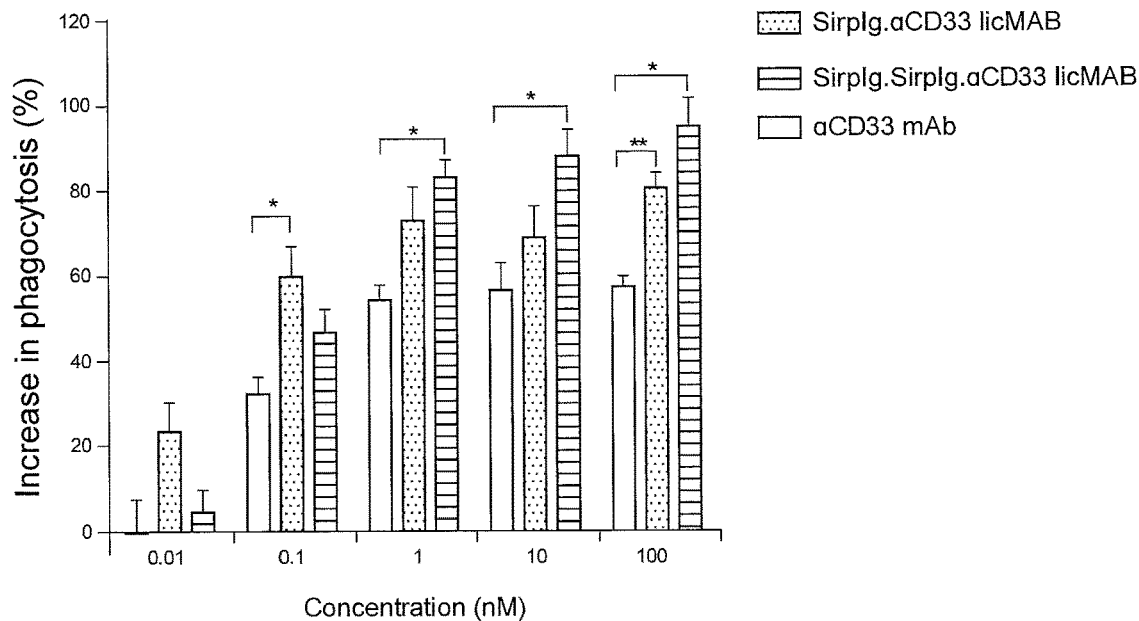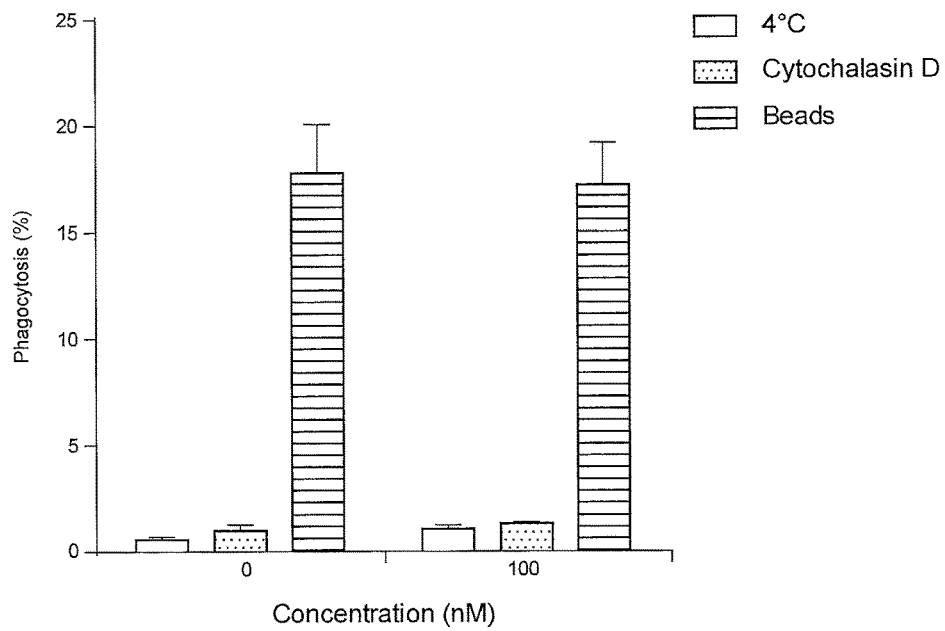
Fig. 16

Binding of PD1ex and αPD-L1 scFv to HEK293_PD-L1 cells
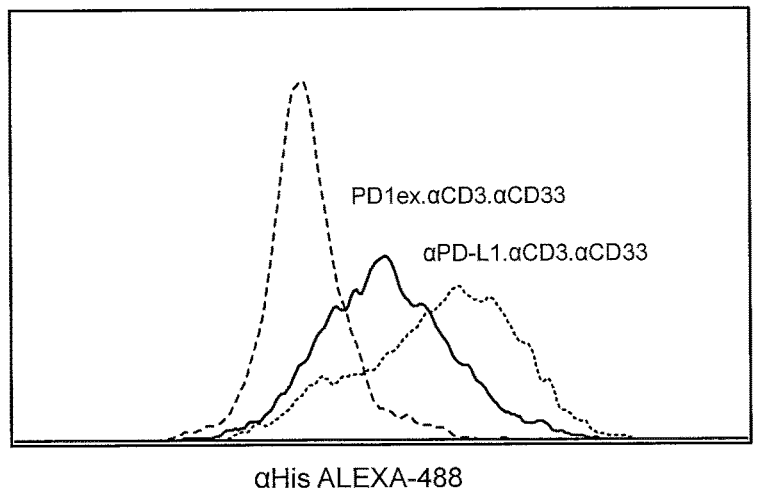
$K_D$ determination studies
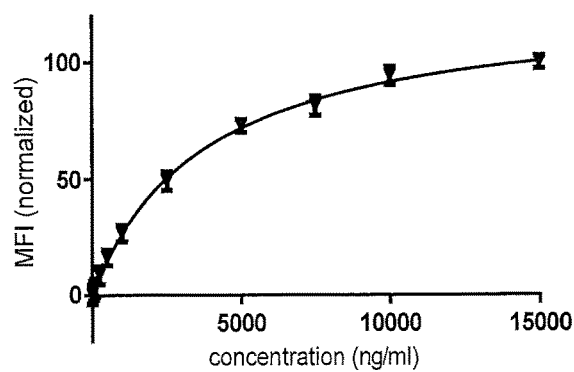
PD1ex.αCD3.αCD33
$K_D$ = 52 nM +/- 3 nM
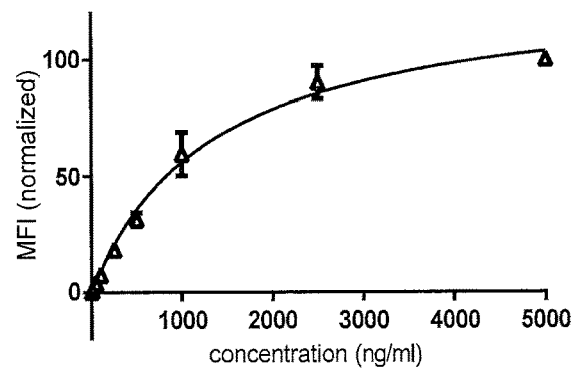
αPD-L1.αCD3.αCD33
$K_D$ = 16 nM +/- 2 nM
Fig. 19A

Binding of αCD3 scFv to Jurkat cells
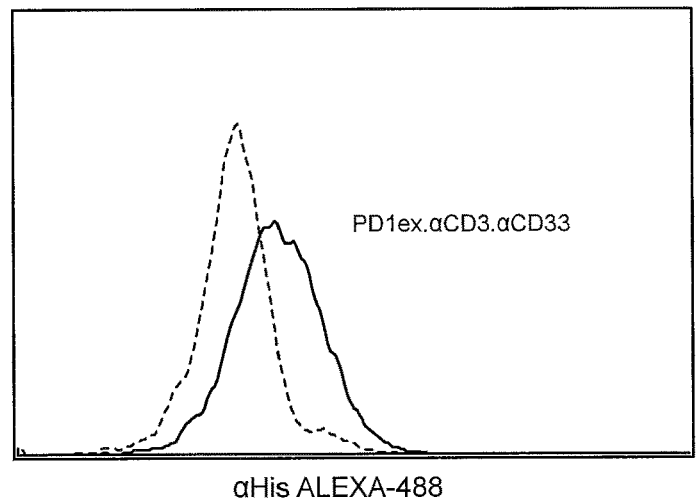
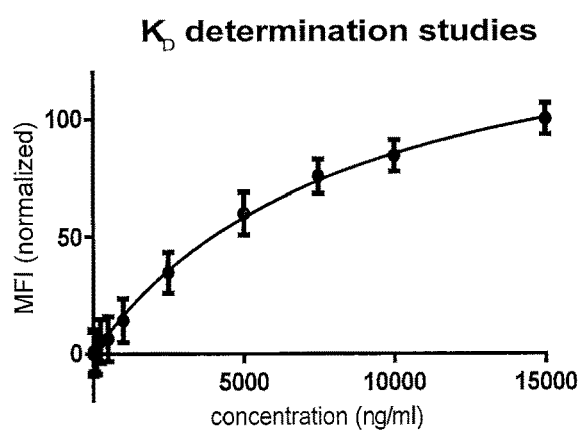
PD1ex.αCD3.αCD33
$K_D$ = 121 nM +/- 9 nM
Fig. 19B

Binding of αCD33 scFv to HEK293_CD33 cells
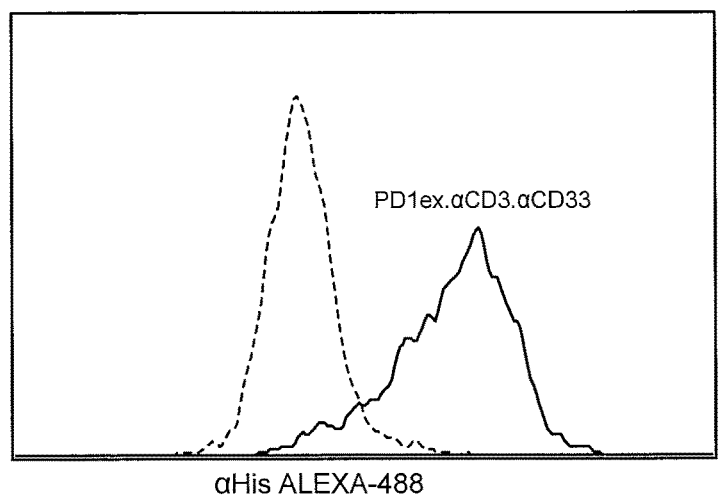
$K_D$ determination studies
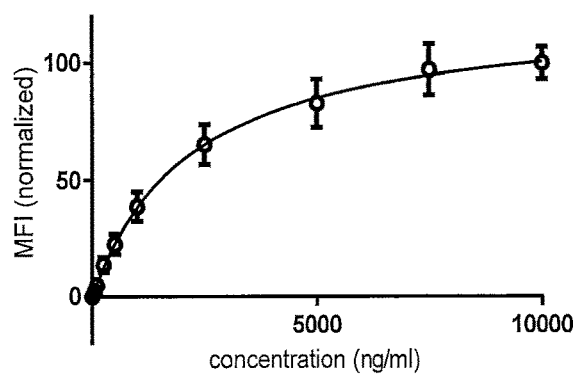
PD1ex.αCD3.αCD33
$K_D$ = 31 nM +/- 1 nM
Fig. 19C Redirected lysis of MOLM-13_PD-L1 cells

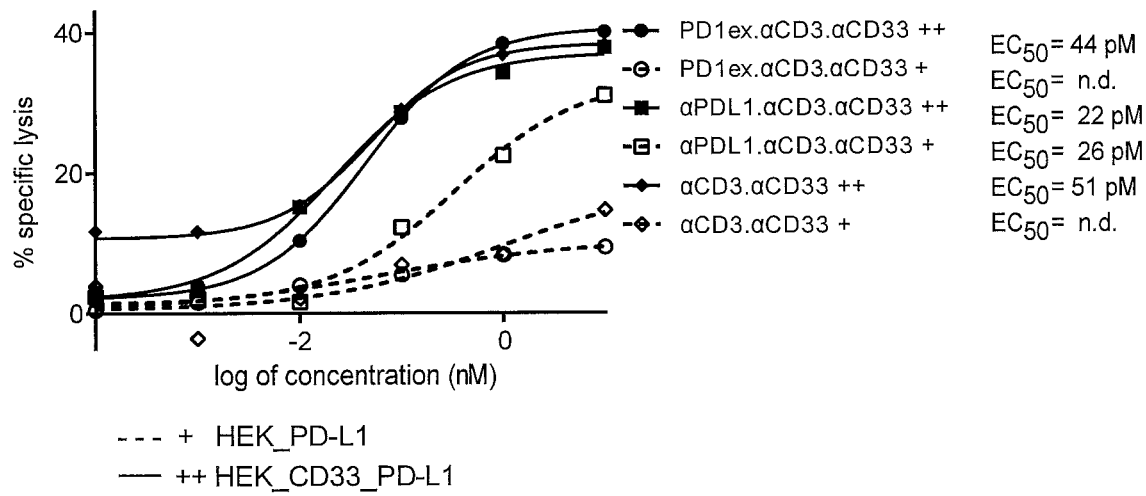
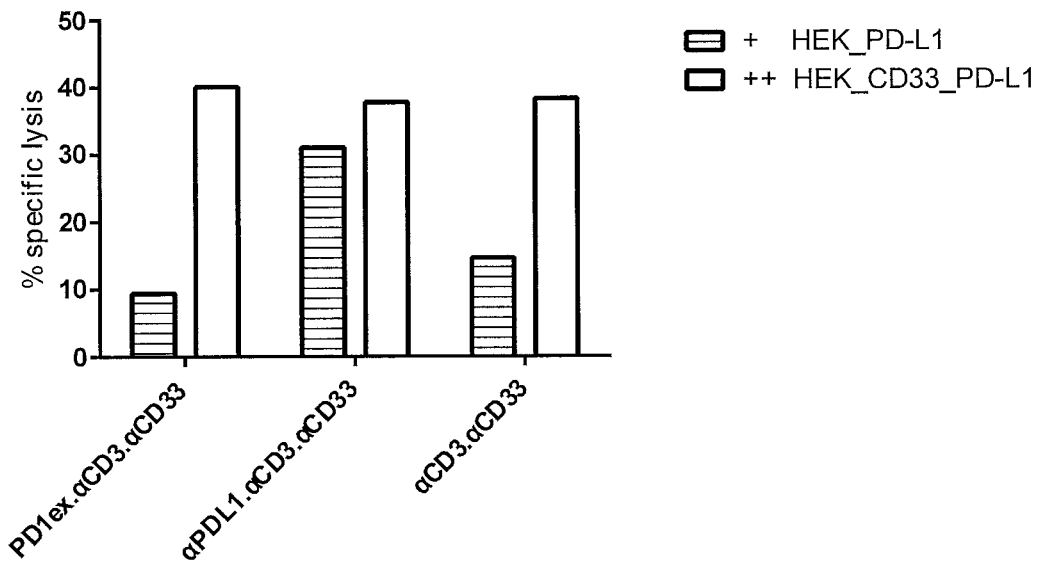
Fig. 21A, B

Killing of MOLM-13_PD-L1 cells by unstimulated T cells:
A  LiCADs in comparison to bispecific molecules
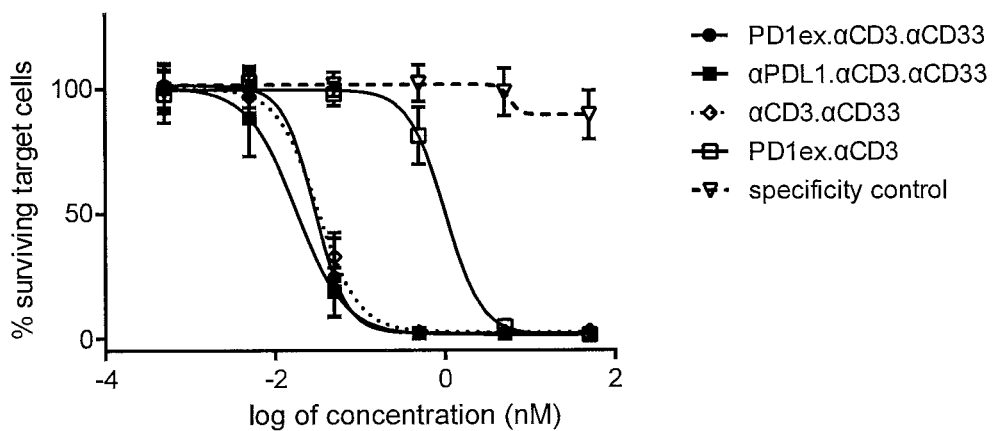
B
Killing of MOLM-13_PDL1 (++) vs. MOLM-13 (+) cells
by unstimulated T cells
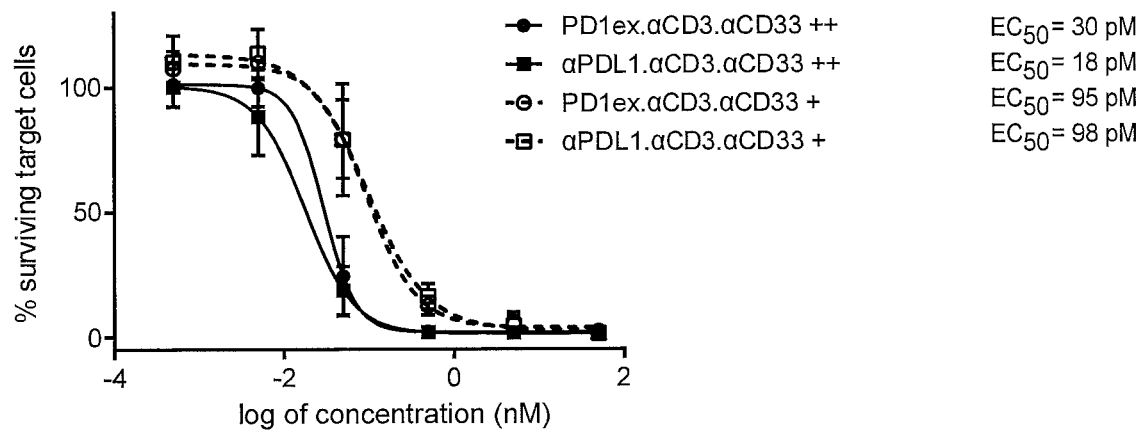
Fig. 22A, B A  T cell proliferation on MOLM-13 vs. MOLM-13_PD-L1 cells
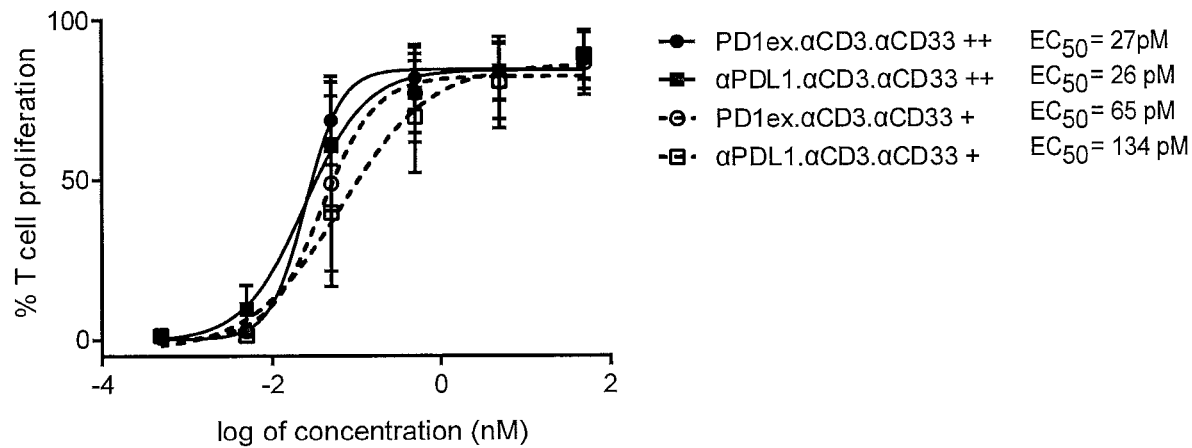
- PD1ex.αCD3.αCD33 ++    $EC_{50}$ = 27 pM
- αPDL1.αCD3.αCD33 ++    $EC_{50}$ = 26 pM
- PD1ex.αCD3.αCD33 +     $EC_{50}$ = 65 pM
- αPDL1.αCD3.αCD33 +     $EC_{50}$ = 134 pM
B  Relative IFNg release
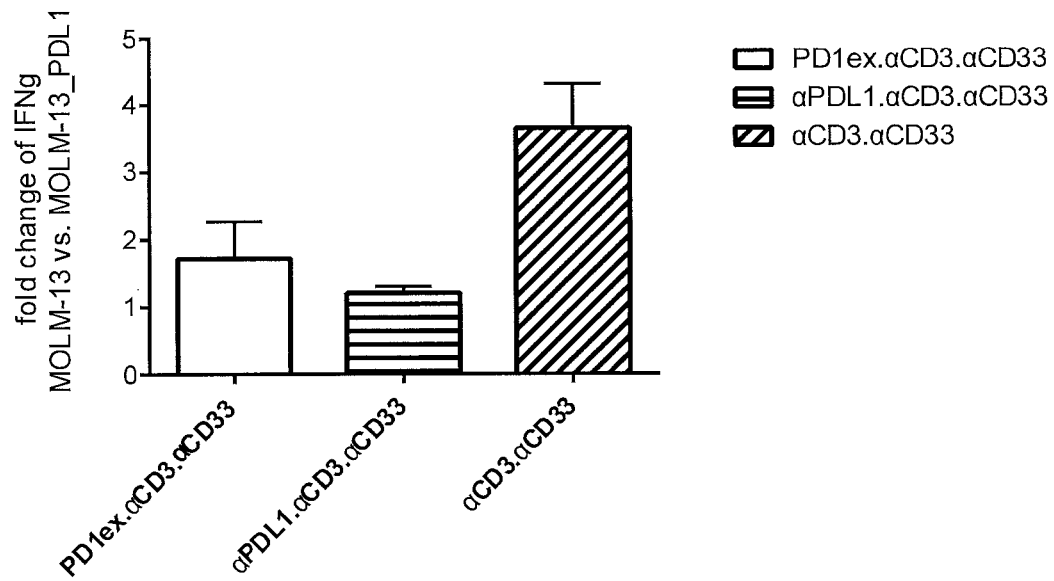
- PD1ex.αCD3.αCD33
- αPDL1.αCD3.αCD33
- αCD3.αCD33
Fig. 23A, B

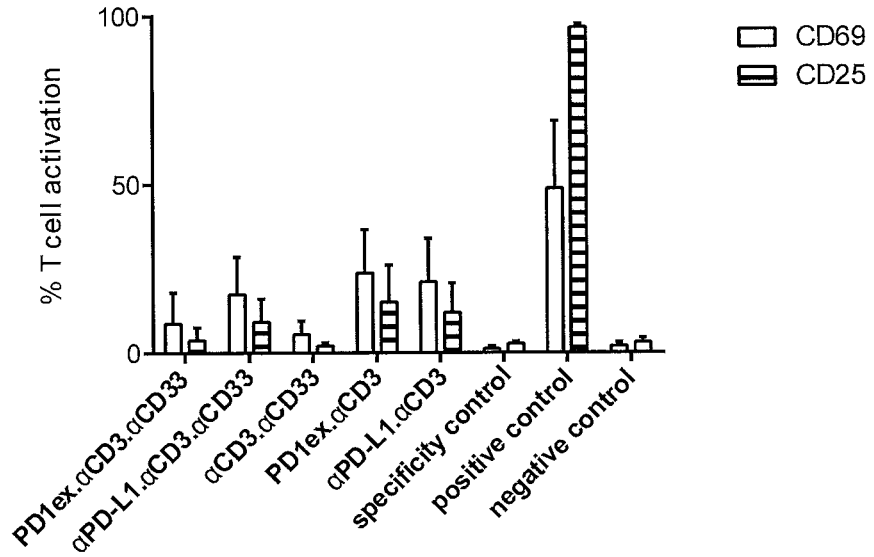
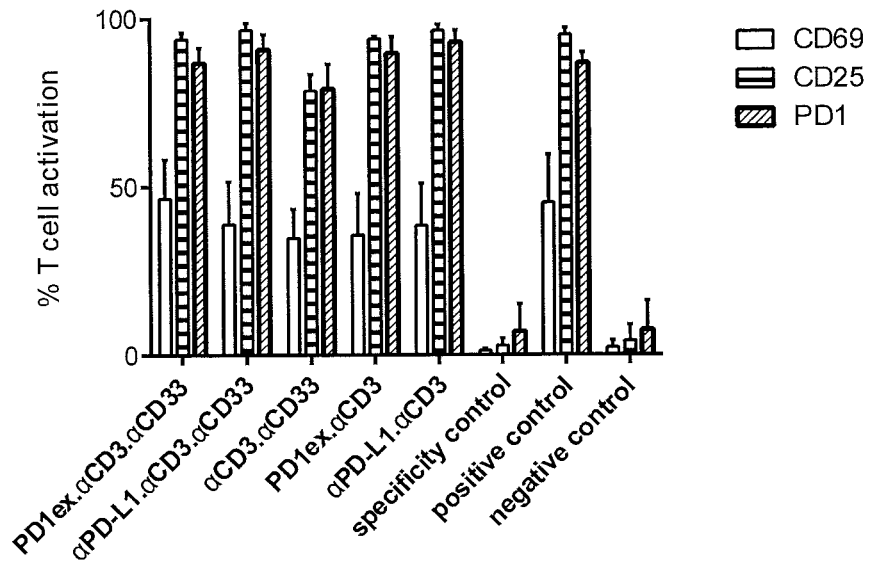
Fig. 24A, B

A
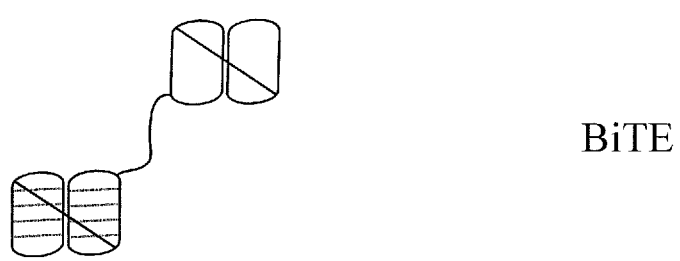
BiTE
B
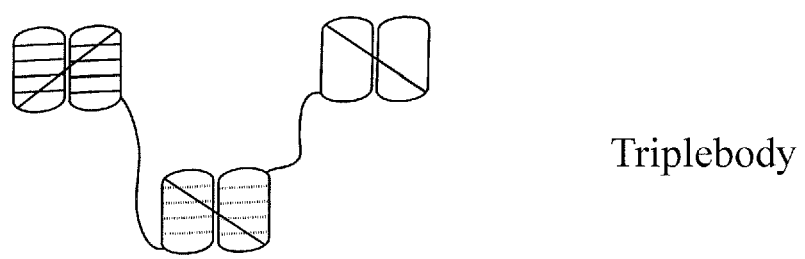
Triplebody
FIG. 27

A   liCAD
B 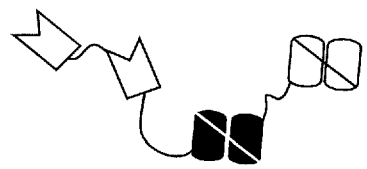  liCAD
FIG. 28

A
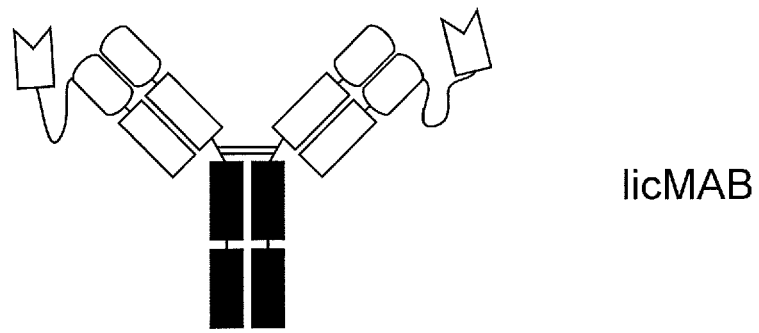
licMAB
B
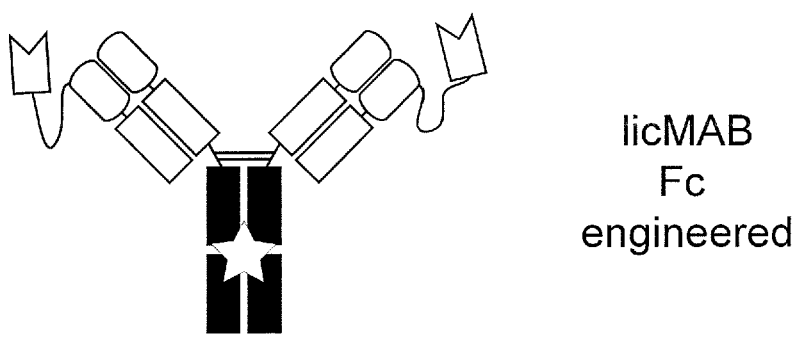
licMAB
Fc
engineered
C
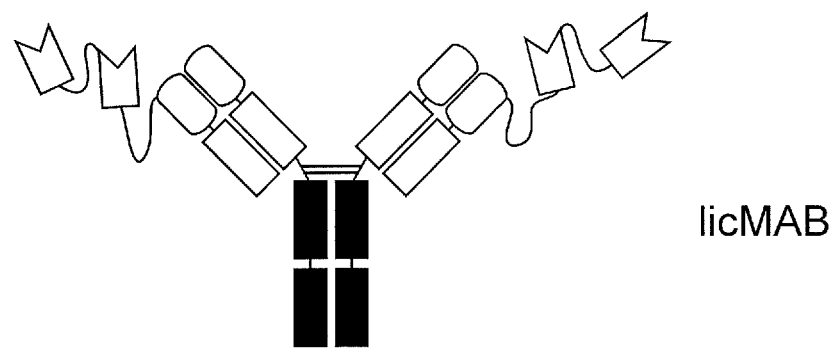
licMAB
FIG. 29

TRISPECIFIC MOLECULE COMBINING SPECIFIC TUMOR TARGETING AND LOCAL IMMUNE CHECKPOINT INHIBITION

CROSS REFERENCE TO RELATED APPLICATIONS

This application is a National Stage Application of International Application Number PCT/EP2016/077174, filed Nov. 9, 2016; which claims priority to European Patent Application No. 15193711.7, filed Nov. 9, 2015.

The Sequence Listing for this application is labeled "SeqList-23Jun21-ST25.txt", which was created on Jun. 23, 2021, and is 26 KB. The entire content is incorporated herein by reference in its entirety.

The present invention relates to a novel molecule comprising three binding sites with specificity for a tumor cell, for an effector cell and for a checkpoint molecule, respectively.

Moreover, the present invention relates to a pharmaceutical composition comprising such a molecule and to uses of such a molecule.

Over the past few decades monoclonal antibodies (mABs) and derivatives thereof have become a promising type of antitumor agents in approaches that are generally referred to as tumor immunotherapy. To date, the US Food and Drug Administration (FDA) has approved more than 20 mABs for therapeutic use and many more are in clinical development.

There are different mechanisms how monoclonal antibodies achieve their therapeutic effects in tumor immunotherapy. For instance, the mABs can specifically bind to the surface of target proteins and recruit immune effector cells via their Fc domain to eliminate the tumor cell.

To date, several antibody formats and derivatives as well as combinational immunotherapies are used in clinical studies or have been approved by the authorities, respectively. Conventional antibodies consist of an Fc (fragment crystallizable) stem and two antigen binding arms called Fab (fragment antigen binding). Antigens are recognized by the variable domains of the heavy ($V_H$) and light ($V_L$) chain, which together constitute the fragment variable (Fv) (FIG. 1A). By connecting the $V_H$ and $V_L$ chain by a flexible linker, a so-called single chain fragment variable (scFv) is generated (FIGS. 1B and C).

Table 1 shows exemplary antibody formats used in clinical therapy or studies, respectively. Antibodies and formats thereof can target different antigens (e.g. tumor specific antigen or checkpoint molecules) and can comprise different effector functions. Effector functions are dependent on the antibody or format thereof (e. g. anti-CD3 in the BiTE, tiplebody or bispecific antibody). Different therapies can be combined.

The conventional IgG format is still predominantly used in therapeutic applications. These molecules are highly stable and very specific for their tumor antigen. However, conventional IgGs lack specificity in binding to the desired effector cells as many immune cells express various Fc receptors. Thus, higher doses are needed which in turn could lead to side effects. Moreover, mABs target cancer cells monospecifically (i.e. through a single tumor antigen). Thus, cancer cells can develop "escape" mechanisms by downregulating the target antigen. Another way of escaping the recognition by the immune system is to upregulate immune checkpoint receptors/ligands.

Recently, IgGs have also been used to inhibit immune checkpoints. Furthermore, studies combining a tumor specific IgG together with an independently administered immune checkpoint inhibiting IgG show more efficient tumor cell killing compared to single application.

Immune checkpoints are fundamental for the maintenance of self-tolerance under normal physiologic conditions. Tumor cells utilize certain immune checkpoints as a main mechanism to escape the immune system and gain immune resistance (Pardoll, 2012). The first mAB interfering with the immune checkpoint, called ipilimumab was approved by the FDA in 2011 for the treatment of metastatic melanoma. Ipilimumab targets the cytotoxic T-lymphocyte-associated antigen 4 (CTLA4), thereby preventing T cell inhibition. However, systemic immune checkpoint inhibition leads to severe systemic side effects due to a general reduction in self-tolerance.

Thus, there is a need in the art for improved ways to treat tumors or cancer, in particular for improved ways of tumor immunotherapy. In particular, there is a need in the art for means to treat tumors or cancer, such as AML, with reduced side effects. Moreover, there is a need in the art for means to treat tumors or cancer, such as AML, which allows for effective elimination of tumor cells while keeping the side effects low. Furthermore, there is a need in the art for means to target tumor cells or cancer, such as AML cells, with improved selectivity. Moreover, there is a need in the art for ways to activate immune cells in tumor immunotherapy in a more specific manner. Moreover, there is a need in the art for means to treat AML that meet some or several of the above needs and at the same time target not only leukemic blasts, but also eliminate AML initiating leukemic stem cells.

It is the object of the present invention to meet such needs.

These objects are solved by the below-described aspects of the present invention, in particular by a molecule according to claim 1 and by a pharmaceutical composition according to claim 15. Preferable embodiments are defined in the dependent claims.

Before the present invention is described in more detail below, it is to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Moreover, the following embodiments can, wherever this does not lead to logical contradictions, be combined with each other without restrictions. Hence, the present disclosure encompasses, even where not explicitly spelled out in the following, any feasible combination of the embodiments described below. Furthermore, the present disclosure encompasses, wherever this does not lead to logical contradictions, the combination of any of the embodiments relating to one aspect of the present invention with the other aspects of the present invention described herein.

In a first aspect, the present invention relates to a molecule comprising:
(i) a first binding site, wherein said first binding site is capable of specifically binding to a cell surface molecule at the cell surface of a tumor cell;
(ii) a second binding site, wherein said second binding site is capable of specifically binding to a cell surface molecule at the cell surface of an immune cell/immune cells;

(iii) a third binding site, wherein said third binding site is capable of specifically binding to a checkpoint molecule at the cell surface of said tumor cell or of said immune cell(s).

The first, second and third binding sites function as three autonomous modules each binding a different target site (see FIG. 2A). Due to the inclusion of the first binding site which is capable of specifically binding to a cell surface molecule at the cell surface of the tumor cell (a tumor antigen on the surface of a tumor cell to be eliminated that is accessible to molecules from the exterior of the cell), molecules according to the invention specifically attach to the tumor cells carrying said tumor antigen. In addition, molecules according to the invention also bind specifically to the immune cells carrying the cell surface molecule to which the second binding site specifically binds (e.g. natural killer cells, macrophages or T cells). By this combination of first and second binding site, the molecule according to the invention is capable of recruiting immune cells specifically to the tumor cells to be eliminated.

Moreover, the molecule according to the invention also comprises a binding site capable of binding to a checkpoint molecule (third binding site). As the skilled person will appreciate, the binding interaction between said third binding site and said checkpoint molecule must be such that, if the molecule according to the invention binds to said checkpoint molecule through its third binding site, this precludes binding of said checkpoint molecule to its endogenous ligand or receptor (i.e. binding of said third binding site to said checkpoint molecule prevents (antiphagocytic) checkpoint signaling through said checkpoint molecule). Thus, binding of the molecule according to the invention through its third binding site to the checkpoint molecule has the effect that (a) if said checkpoint molecule is a checkpoint receptor ligand present on the tumor cell, said checkpoint receptor ligand cannot bind to its corresponding checkpoint receptor on the immune cell anymore and thus the immune cell cannot receive an antiphagocytic checkpoint signal (a "Do not eat me" signal) from said tumor cell, or (b) if said checkpoint molecule is a checkpoint receptor present on an immune cell, said checkpoint receptor cannot bind to a checkpoint receptor ligand on the tumor cell to be eliminated anymore and thus the immune cell cannot receive an antiphagocytic checkpoint signal from said tumor cell.

Since the first, second and third binding site are all present in a single molecule, the third binding site is brought into close proximity of the tumor cell to be eliminated and the immune cell. Thus, if the checkpoint molecule to which said third binding site specifically binds is a checkpoint receptor ligand, the third binding site binds, due to the spatial proximity, preferably to a checkpoint receptor ligand on the tumor cell (rather than on some other cell). Alternatively, if the checkpoint molecule to which said third binding site specifically binds is a checkpoint receptor, the third binding site binds, due to the spatial proximity, preferably to a checkpoint receptor on the immune cell to which the molecule according to the invention is linked via its second binding site. As a result, binding of the third binding site to other cells besides the tumor cells to be eliminated (if the checkpoint molecule to which said third binding site specifically binds is a checkpoint receptor ligand) or besides the immune cells recruited to the tumor cells to be eliminated (if the checkpoint molecule to which said third binding site specifically binds is a checkpoint receptor) is reduced and specific blockage of the checkpoint signaling from the tumor cells to be eliminated to the recruited immune cells is achieved (rather than an inhibition of the checkpoint signal from other cells than the tumor cells to be eliminated or to other cells than the immune cells that are specifically recruited to the tumor cells to be eliminated by the molecule according to the invention). This results in effective destruction of the tumor cells by the recruited immune cells, while at the same time side effects are reduced.

As indicated above, the first binding site of the molecule according to the invention should be capable of specifically binding to a cell surface molecule on the tumor cells to be eliminated. Preferably, said cell surface molecule at the cell surface of said tumor cell is specific for said tumor cell.

Cell surface molecules (or combinations of cell surface molecules) that are specific for certain tumor cells are known to the skilled person. CD33, for example, is a cell surface molecule that is highly expressed on AML (acute myeloid leukemia) cells. CD20 is a cell surface molecule that is expressed on B cell lymphomas and leukemias (but also on normal B cells). Further examples of tumor markers are shown in Table 2 below. Moreover, an extensive overview of tumor markers is available e.g. from http://www.proteinatlas.org/.

Alternatively, cell surface molecules (or combinations of cell surface molecules) that are specific for certain tumor cells may be identified by immunostaining in combination with flow cytometry or immunofluorescence staining of histological sections.

The second binding site of the molecule according to the invention should, as indicated above, have binding specificity for a cell surface molecule at the cell surface of immune cells to be recruited to the tumor cells. Preferably, said cell surface molecule at the cell surface of said immune cell/immune cells is specific for said immune cell(s).

Examples of suitable cell surface molecules that are specific for a certain immune cell/certain immune cells are as follows: CD16 is a cell surface molecule that is expressed specifically on natural killer cells (NK cells) and macrophages, monocytes and dendritic cells. CD3 is expressed on T cells. Further examples are shown in Table 3.

The third binding site of the molecule according to the invention should, as discussed above, have binding specificity for a checkpoint molecule, either for a checkpoint receptor ligand present at the cell surface of the tumor cell to be eliminated (which carries the cell surface molecule to which said first binding site binds), or for a checkpoint receptor on the cell surface of said immune cell (which carries the cell surface molecule to which said second binding site binds). As indicated above, this interaction should prevent checkpoint signaling mediated by said checkpoint molecule (i.e. upon binding of said third binding site to said checkpoint molecule, said checkpoint molecule is e.g. not capable of transmitting to said immune cell an antiphagocytic checkpoint signal (i.e. said checkpoint molecule is not capable of transmitting to said immune cell an inhibitory signal that prevents the immune cell from attacking/destroying said tumor cell) or of transmitting a regulatory suppression signal to said immune cell (such as a T cell suppression signal)).

Examples of suitable checkpoint molecules at the cell surface of said tumor cell are as follows: CD47, PD-L1, CD80, CD86, GAL9 and CD40.

Examples of suitable checkpoint molecules at the cell surface of said immune cell(s) are as follows: Sirp alpha, PD-A, CTLA-4, Tim3, CD40L.

The third binding site of the molecule according to the invention may for example be a binding site capable of binding to SIRPα. SIRPα (signal regulatory protein Q, also known as CD172a) is a checkpoint receptor that is specifically expressed on myeloid cells (e.g. macrophages). The endogenous checkpoint receptor ligand that binds to SIRPα and activates the receptor is the membrane protein CD47, which is broadly expressed on various cell types as marker of "self". CD47 binding to SIRPα functions as an antiphagocytic checkpoint signal (a "Don't eat me" signal) to phagocytic cells, in particular macrophages, i.e. upon binding to its checkpoint receptor ligand CD47, the checkpoint receptor SIRPα provides a signal to the immune cell that prevents the immune cell from phagocytosing the cell carrying the CD47 molecule (see FIG. 3 A). CD47 is for example present on red blood cells and prevents the clearance of these cells by phagocytic cells.

CD47 is also often highly overexpressed on cancer cells and correlates with a poor prognosis (Majeti et al., 2009; Chao et al., 2010). A blockade of the SIRPα-CD47 interaction by an anti-CD47 antibody increases phagocytosis of tumor cells tremendously and hinders the tumor cells to evade phagocytic destruction by the immune cell through overexpression of CD47 (Willingham et al., 2012).

The combined application of two antibodies, an anti-CD47 antibody and a tumor-specific mAB (e.g. rituximab, anti-CD20 mAB) leads to the inhibition of engraftment of cancer cells and even pre-established leukemias (Barclay and Van den Berg, 2014) (see FIG. 3 B; the tumor marker could e.g. be CD20 and the tumor-specific monoclonal antibody rituximab).

As the inventors have found, a molecule that combines a binding site that specifically binds to a marker of the tumor cell to be eliminated, a binding site that specifically binds to a marker of an immune cell and a binding site that specifically binds to a checkpoint molecule efficiently eliminates the tumor cell while at the same time reducing side effects due to systemic blockage of checkpoint signaling. Thus, a molecule that combines a binding site that is specific for e.g. CD33 (which is found on AML cells), a binding site that binds to CD16 (a marker for immune cells, in particular macrophages, NK cells, monocytes and dendritic cells) and a binding site that binds to the checkpoint receptor ligand CD47 (thus inhibiting antiphagocytic checkpoint signaling from the tumor cell through SIRPα to the immune cell) efficiently eliminates the AML blasts while at the same time avoiding side effects due to systemic blockage of CD47-SIRPα checkpoint signaling that otherwise may occur (see FIG. 3 C).

The concept underlying the present invention was to provide for a combination of tumor directed targeting using a high affinity domain ("first binding site"), with the recruitment of an immune cell using a second domain capable of specifically binding to an immune cell ("second binding site"), together with a simultaneous interference with an immune checkpoint, using a third domain that is capable of specifically binding to a checkpoint molecule either on the cell surface of the tumor cell or of the immune cell ("third binding site"). The high affinity binding to the tumor cells allows for an increased specificity for the tumor cells and for an overall recruitment of effector cells to the tumor site. The binding to the immune cells afforded by the second binding site brings the immune cells in close vicinity of the tumor cells. The binding through the third binding site to an immune checkpoint allows for the activation of the immune cells by either blocking inhibitory checkpoint signals or by promoting activating checkpoint signals at the tumor site. Because it is typically only a local interference with the checkpoint(s), there is no targeting effect to non-tumorigenic cells, and there is also a decrease of effects caused by binding to cells that lack the ligand for the "first binding site", but contain the ligand for the "third binding site". Typically, the third binding site does not have a targeting effect and thus delivers a checkpoint blockade (or checkpoint activation) specifically to cells expressing the tumor antigens, since the native checkpoint domains interact weekly with their receptors. Hence, strong binding to the tumor cells depends on the binding (through the first binding site) to the tumor antigen. Therefore, the endogenous extracellular domain of an immune checkpoint receptor/co-receptor ("third binding site") fused to the antibody or derivative thereof ("first binding site" and "second binding") will not target cells on their own but will activate immune cells at the tumor site.

The molecule according to the invention can easily be designed to target different tumor cells by exchanging the domain including the first binding site (module 1 in FIG. 2A) for a domain having a first binding site with a different binding specificity, namely a binding specificity for a cell surface molecule that is specific for the (other) tumor cells to be targeted. In order to increase the specificity with which the molecule according to the invention binds to the tumor cells, a further module with binding affinity for a second cell surface molecule of said tumor cell may be included in the molecule according to the invention.

As the immune system comprises different types of immune cells (e.g. T cells, NK cells, macrophages, monocytes etc.), the effector-recruiting module (module 2 in FIG. 2A) can be chosen such that the most suitable type of immune cell is recruited as effector cell, depending on the field of application. For example, T cells may be recruited as effector cells in melanoma (cf. treatment with ipilimumab, pembrolizumab or nivolumab). CD3/T cells may be recruited as effector cells in NHL and relapsed or refractory B-cell precursor acute lymphoblastic leukemia (cf. treatment with blinatumomab).

Moreover, the immune modulation achieved by the binding of the third binding site (included in module 3 of FIG. 2A) to the checkpoint molecule can be regulated. For example, by including two binding sites of the same specificity, a higher binding affinity and a higher local concentration of the third binding site can be achieved.

Thus, the molecule according to the invention can be specifically adapted for different indications.

Several examples how molecules according to the invention may be constructed are shown in Table 4, and FIGS. 28A-28C and 29A-C.

In some embodiments, said tumor cell is selected from the group consisting of an NHL (non-Hodgkin B-cell lymphoma) cell, a B-ALL (B-cell acute lymphoblastic leukemia) cell, a B cell lymphoma cell, a breast cancer cell, an AML (acute myeloid leukemia) cell, a gastrointestinal cancer cell, a lung cancer cell, an ovarian cancer cell and a colorectal cancer cell. More preferably, said tumor cell is selected from the group consisting of an AML cell, a B-ALL, and an NHL cell, even more preferably, said tumor cell is an AML cell.

In some embodiments, said cell surface molecule at the cell surface of said tumor cell is specific for said tumor cell.

In some embodiments, said immune cell is/immune cells are selected from the group consisting of NK cells, NKT cells, T cells, macrophages, monocytes, neutrophilic granulocytes and dendritic cells (DCs). More preferably, said immune cell is/immune cells are selected from the group consisting of NK cells, NKT cells, gamma delta T cells and macrophages, even more preferably from the group consisting of NK cells and macrophages. As cells of the innate immune system, NK cells and NKT cells have the advantage of a particularly fast response time. Moreover, upon activation these cells produce cytokines (e.g. IFN gamma and IL-12) that have anti-tumor activity and stimulate further cells of the immune system. T cells have the advantage of a strong cell proliferation after activation due to clonal expansion.

In some preferred embodiments, said cell surface molecule at the cell surface of said tumor cell, said cell surface molecule at the cell surface of said immune cell(s) and said checkpoint molecule are one of the following combinations (see also FIG. 9):

(i) said cell surface molecule at the cell surface of said tumor cell is CD33, said cell surface molecule at the cell surface of said immune cell(s) is CD16 and said checkpoint molecule is CD47;

(ii) said cell surface molecule at the cell surface of said tumor cell is CD33, said cell surface molecule at the cell surface of said immune cell(s) is CD3 and said checkpoint molecule is PD-L1 (programmed death-ligand 1);

(iii) said cell surface molecule at the cell surface of said tumor cell is CD33, said cell surface molecule at the cell surface of said immune cell(s) is CD3 and said checkpoint molecule is CD80/CD86;

(iv) said cell surface molecule at the cell surface of said tumor cell is CD19, said cell surface molecule at the cell surface of said immune cell(s) is CD16 and said checkpoint molecule is CD47;

(v) said cell surface molecule at the cell surface of said tumor cell is CD19, said cell surface molecule at the cell surface of said immune cell(s) is CD3 and said checkpoint molecule is PD-L1;

(vi) said cell surface molecule at the cell surface of said tumor cell is CD19, said cell surface molecule at the cell surface of said immune cell(s) is CD3 and said checkpoint molecule is CD80/CD86;

(vii) said cell surface molecule at the cell surface of said tumor cell is CD20, said cell surface molecule at the cell surface of said immune cell(s) is CD16 and said checkpoint molecule is CD47;

(viii) said cell surface molecule at the cell surface of said tumor cell is CD20, said cell surface molecule at the cell surface of said immune cell(s) is CD3 and said checkpoint molecule is PD-L1;

(ix) said cell surface molecule at the cell surface of said tumor cell is CD20, said cell surface molecule at the cell surface of said immune cell(s) is CD3 and said checkpoint molecule is CD80/CD86;

(x) said cell surface molecule at the cell surface of said tumor cell is CEA (carcinoembryonic antigen), said cell surface molecule at the cell surface of said immune cell(s) is CD16 and said checkpoint molecule is CD47;

(xi) said cell surface molecule at the cell surface of said tumor cell is CEA, said cell surface molecule at the cell surface of said immune cell(s) is CD3 and said checkpoint molecule is PD-L1;

(xii) said cell surface molecule at the cell surface of said tumor cell is CEA, said cell surface molecule at the cell surface of said immune cell(s) is CD3 and said checkpoint molecule is CD80/CD86;

(xiii) said cell surface molecule at the cell surface of said tumor cell is CEA, said cell surface molecule at the cell surface of said immune cell(s) is CD16 and said checkpoint molecule is PD-L1;

(xiv) said cell surface molecule at the cell surface of said tumor cell is Epcam (epithelial cell adhesion molecule), said cell surface molecule at the cell surface of said immune cell(s) is CD16 and said checkpoint molecule is CD47;

(xv) said cell surface molecule at the cell surface of said tumor cell is Epcam, said cell surface molecule at the cell surface of said immune cell(s) is CD3 and said checkpoint molecule is PD-L1;

(xvi) said cell surface molecule at the cell surface of said tumor cell is Epcam, said cell surface molecule at the cell surface of said immune cell(s) is CD3 and said checkpoint molecule is CD80/CD86;

(xvii) said cell surface molecule at the cell surface of said tumor cell is CD123, said cell surface molecule at the cell surface of said immune cell(s) is CD16 and said checkpoint molecule is CD47;

(xviii) said cell surface molecule at the cell surface of said tumor cell is CD123, said cell surface molecule at the cell surface of said immune cell(s) is CD3 and said checkpoint molecule is PD-L1;

(xix) said cell surface molecule at the cell surface of said tumor cell is CD123, said cell surface molecule at the cell surface of said immune cell(s) is CD3 and said checkpoint molecule is CD80/CD86; Preferred are combinations (i), (ii), (iii) and (iv).

In some preferred embodiments, said first binding site, said second binding site and said third binding site are one of the following combinations (see also FIG. 9):

(i) said first binding site is formed by an αCD33 scFv, said second binding site is formed by an αCD16 scFv and said third binding site is formed by SirpIg, wherein, preferably, only one or more than one copy of SirpIg is present in the molecule according to the invention;

(ii) said first binding site is formed by an αCD33 scFv, said second binding site is formed by an αCD3 scFv and said third binding site is formed by PD1ex ("PD1ex" designates the extracellular domain of PD1), wherein, preferably, only one or more than one copy of PD1ex is present in the molecule according to the invention;

(iii) said first binding site is formed by an αCD33 scFv, said second binding site is formed by an αCD3 scFv and said third binding site is formed by CTLA4ex ("CTLA4ex" designates the extracellular domain of CTLA4), wherein, preferably, only one or more than one copy of CTLA4ex is present in the molecule according to the invention;

(iv) said first binding site is formed by an αCD33 scFv, said second binding site is formed by an Fc domain and said third binding site is formed by SirpIg, wherein, preferably, only one or more than one copy of SirpIg is present in the molecule according to the invention;

(v) said first binding site is formed by an αCD33 scFv, said second binding site is formed by an Fc (inactive engineered) domain and said third binding site is formed by SirpIg, wherein, preferably, only one or more than one copy of SirpIg is present in the molecule according to the invention; (an "Fc (inactive engineered)" domain, as used herein, is an Fc domain in which the amino acid sequence of the Fc domain has been mutated in such a way that the Fc (inactive engineered) domain is still able to bind to Fc receptors, such as CD64 and CD32a but has a reduced or abolished binding the CD16 receptor; see e.g. Wines et al., 2000; US 2012/0251531)

(vi) said first binding site is formed by an αCD33 scFv, said second binding site is formed by an Fc (inactive engineered) domain and said third binding site is formed by PD1ex, wherein, preferably, only one or more than one copy of the PD1ex is present in the molecule according to the invention;

(vii) said first binding site is formed by an αCD33 scFv, said second binding site is formed by an Fc (inactive engineered) domain and said third binding site is formed by CTLA4ex, wherein, preferably, only one or more than one copy of CTLA4ex is present in the molecule according to the invention;

(viii) said first binding site is formed by an αCD19 scFv, said second binding site is formed by an αCD16 scFv and said third binding site is formed by SirpIg, wherein, preferably, only one or more than one copy of SirpIg is present in the molecule according to the invention;

(ix) said first binding site is formed by an αCD19 scFv, said second binding site is formed by an αCD3 scFv and said third binding site is formed by PD1ex, wherein, preferably, only one or more than one copy of PD1ex is present in the molecule according to the invention;

(x) said first binding site is formed by an αCD19 scFv, said second binding site is formed by an αCD3 scFv and said third binding site is formed by CTLA4ex, wherein, preferably, only one or more than one copy of CTLA4ex is present in the molecule according to the invention;

(xi) said first binding site is formed by an αCD19 scFv, said second binding site is formed by an Fc domain and said third binding site is formed by SirpIg, wherein, preferably, only one or more than one copy of SirpIg is present in the molecule according to the invention;

(xii) said first binding site is formed by an αCD19 scFv, said second binding site is formed by an Fc (inactive engineered) domain and said third binding site is formed by SirpIg, wherein, preferably, only one or more than one copy of SirpIg is present in the molecule according to the invention;

(xiii) said first binding site is formed by an αCD19 scFv, said second binding site is formed by an Fc (inactive engineered) domain and said third binding site is formed by PD1ex, wherein, preferably, only one or more than one copy of the PD1ex is present in the molecule according to the invention;

(xiv) said first binding site is formed by an αCD19 scFv, said second binding site is formed by an Fc (inactive engineered) domain and said third binding site is formed by CTLA4ex, wherein, preferably, only one or more than one copy of CTLA4ex is present in the molecule according to the invention;

(xv) said first binding site is formed by an αCD20 scFv, said second binding site is formed by an αCD16 scFv and said third binding site is formed by SirpIg, wherein, preferably, only one or more than one copy of SirpIg is present in the molecule according to the invention;

(xvi) said first binding site is formed by an αCD20 scFv, said second binding site is formed by an αCD3 scFv and said third binding site is formed by PD1ex, wherein, preferably, only one or more than one copy of PD1ex is present in the molecule according to the invention;

(xvii) said first binding site is formed by an αCD20 scFv, said second binding site is formed by an αCD3 scFv and said third binding site is formed by CTLA4ex, wherein, preferably, only one or more than one copy of CTLA4ex is present in the molecule according to the invention;

(xviii) said first binding site is formed by an αCD20 scFv, said second binding site is formed by an Fc domain and said third binding site is formed by SirpIg, wherein, preferably, only one or more than one copy of SirpIg is present in the molecule according to the invention;

(xix) said first binding site is formed by an αCD20 scFv, said second binding site is formed by an Fc (inactive engineered) domain and said third binding site is formed by SirpIg, wherein, preferably, only one or more than one copy of SirpIg is present in the molecule according to the invention;

(xx) said first binding site is formed by an αCD20 scFv, said second binding site is formed by an Fc (inactive engineered) domain and said third binding site is formed by PD1ex, wherein, preferably, only one or more than one copy of the PD1ex is present in the molecule according to the invention;

(xxi) said first binding site is formed by an αCD20 scFv, said second binding site is formed by an Fc (inactive engineered) domain and said third binding site is formed by CTLA4ex, wherein, preferably, only one or more than one copy of CTLA4ex is present in the molecule according to the invention;

(xxii) said first binding site is formed by an αCEA scFv, said second binding site is formed by an αCD16 scFv and said third binding site is formed by SirpIg, wherein, preferably, only one or more than one copy of SirpIg is present in the molecule according to the invention;

(xxiii) said first binding site is formed by an αCEA scFv, said second binding site is formed by an αCD3 scFv and said third binding site is formed by PD1ex, wherein, preferably, only one or more than one copy of PD1ex is present in the molecule according to the invention;

(xxiv) said first binding site is formed by an αCEA scFv, said second binding site is formed by an αCD3 scFv and said third binding site is formed by CTLA4ex, wherein, preferably, only one or more than one copy of CTLA4ex is present in the molecule according to the invention;

(xxv) said first binding site is formed by an αCEA scFv, said second binding site is formed by an Fc domain and said third binding site is formed by SirpIg, wherein, preferably, only one or more than one copy of SirpIg is present in the molecule according to the invention;

(xxvi) said first binding site is formed by an αCEA scFv, said second binding site is formed by an Fc (inactive engineered) domain and said third binding site is formed by SirpIg, wherein, preferably, only one or more than one copy of SirpIg is present in the molecule according to the invention;

(xxvii) said first binding site is formed by an αCEA scFv, said second binding site is formed by an Fc (inactive engineered) domain and said third binding site is formed by PD1ex, wherein, preferably, only one or more than one copy of the PD1ex is present in the molecule according to the invention;

(xxviii) said first binding site is formed by an αCEA scFv, said second binding site is formed by an Fc (inactive engineered) domain and said third binding site is formed by CTLA4ex, wherein, preferably, only one or more than one copy of CTLA4ex is present in the molecule according to the invention;

(xxix) said first binding site is formed by an αEpcam scFv, said second binding site is formed by an αCD16 scFv and said third binding site is formed by SirpIg, wherein, preferably, only one or more than one copy of SirpIg is present in the molecule according to the invention;

(xxx) said first binding site is formed by an αEpcam scFv, said second binding site is formed by an αCD3 scFv and said third binding site is formed by PD1ex, wherein, preferably, only one or more than one copy of PD1ex is present in the molecule according to the invention;

(xxxi) said first binding site is formed by an αEpcam scFv, said second binding site is formed by an αCD3 scFv and said third binding site is formed by CTLA4ex, wherein, preferably, only one or more than one copy of CTLA4ex is present in the molecule according to the invention;

(xxxii) said first binding site is formed by an αEpcam scFv, said second binding site is formed by an Fc domain and said third binding site is formed by SirpIg, wherein, preferably, only one or more than one copy of SirpIg is present in the molecule according to the invention;

(xxxiii) said first binding site is formed by an αEpcam scFv, said second binding site is formed by an Fc (inactive engineered) domain and said third binding site is formed by SirpIg, wherein, preferably, only one or more than one copy of SirpIg is present in the molecule according to the invention;

(xxxiv) said first binding site is formed by an αEpcam scFv, said second binding site is formed by an Fc (inactive engineered) domain and said third binding site is formed by PD1ex, wherein, preferably, only one or more than one copy of the PD1cx is present in the molecule according to the invention;

(xxxv) said first binding site is formed by an αEpcam scFv, said second binding site is formed by an Fc (inactive engineered) domain and said third binding site is formed by CTLA4ex, wherein, preferably, only one or more than one copy of CTLA4ex is present in the molecule according to the invention;

(xxxvi) said first binding site is formed by an αCD123 scFv, said second binding site is formed by an αCD16scFv and said third binding site is formed by SirpIg, wherein, preferably, only one or more than one copy of SirpIg is present in the molecule according to the invention;

(xxxvii) said first binding site is formed by an αCD123 scFv, said second binding site is formed by an αCD3 scFv and said third binding site is formed by PDIex, wherein, preferably, only one or more than one copy of PD1ex is present in the molecule according to the invention;

(xxxviii) said first binding site is formed by an αCD123 scFv, said second binding site is formed by an αCD3 scFv and said third binding site is formed by CTLA4ex, wherein, preferably, only one or more than one copy of CTLA4ex is present in the molecule according to the invention;

(xxxix) said first binding site is formed by an αCD123 scFv, said second binding site is formed by an Fc domain and said third binding site is formed by SirpIg, wherein, preferably, only one or more than one copy of SirpIg is present in the molecule according to the invention;

(xl) said first binding site is formed by an αCD123 scFv, said second binding site is formed by an Fc (inactive engineered) domain and said third binding site is formed by SirpIg, wherein, preferably, only one or more than one copy of SirpIg is present in the molecule according to the invention;

(xli) said first binding site is formed by an αCD123 scFv, said second binding site is formed by an Fc (inactive engineered) domain and said third binding site is formed by PD1ex, wherein, preferably, only one or more than one copy of the PD1ex is present in the molecule according to the invention;

(xlii) said first binding site is formed by an αCD123 scFv, said second binding site is formed by an Fc (inactive engineered) domain and said third binding site is formed by CTLA4ex, wherein, preferably, only one or more than one copy of CTLA4cx is present in the molecule according to the invention.

Preferred are combinations (i), (ii), (iii), (iv), (v), (viii), (xi), and (xxxix).

In some embodiments, said first binding site is capable of specifically binding to CD33, said second binding site is capable of specifically binding to CD16 and said third binding site is capable of specifically binding to CD47.

In some embodiments, said cell surface molecule at the cell surface of said immune cell(s) is specific for said immune cell(s).

In some embodiments, said checkpoint molecule is a checkpoint receptor ligand and/or said checkpoint molecule is present at the cell surface of said tumor cell (i.e. of the cells carrying the cell surface molecule to which the first binding site binds). Preferably, said checkpoint molecule is a checkpoint receptor and/or said checkpoint molecule is present at the cell surface of said immune cell (i.e. of the immune cell carrying the cell surface molecule to which the second binding site binds).

In some embodiments, said checkpoint molecule is a checkpoint receptor that is present on the cell surface of said immune cell(s). As the skilled person will appreciate, the immune cell to which said molecule according to the invention is capable of binding through its second binding site must also carry on its cell surface said checkpoint receptor to which said third binding site is capable of binding.

In some preferred embodiments, said checkpoint molecule is a checkpoint receptor ligand for a checkpoint receptor that is present on the cell surface of said immune cell(s). As the skilled person will appreciate, the immune cell to which said molecule according to the invention is capable of binding through its second binding site must also carry on its cell surface said checkpoint receptor to which said checkpoint receptor ligand binds. Moreover, as the skilled person will appreciate, the tumor cell to which said molecule according to the invention is capable of binding through its first binding site must also carry on its cell surface said checkpoint receptor ligand to which said third binding site binds.

In some embodiments, said tumor cell overexpresses said checkpoint molecule.

In some embodiments, the affinity of said first binding site for said cell surface molecule at the cell surface of said tumor cell is higher than the affinity of said third binding site for said checkpoint molecule, preferably by at least a factor of 10, more preferably by at least a factor of 25, even more preferably by at least a factor of 50.

In some embodiments, the affinity of said second binding site for said cell surface molecule at the cell surface of said immune cell(s) is higher than the affinity of said third binding site for said checkpoint molecule, preferably by at least a factor of 10, more preferably by at least a factor of 25, even more preferably by at least a factor of 50.

In some embodiments, the affinity of said first binding site for said cell surface molecule at the cell surface of said tumor cell is within a range of from 0.1 to 200 nM, preferably within a range of from 1 nM to 50 nM.

In some embodiments, the affinity of said second binding site for said cell surface molecule at the cell surface of said immune cell/immune cells is within a range of from 0.1 to 200 nM, preferably within a range of from 1 to 50 nM.

In some embodiments, the affinity of said third binding site for said checkpoint molecule is within a range of from 100 nM to 5 μM, preferably within a range of from 500 nM to 3 μM.

The relative affinities of the different binding sites defined above, and the low to medium affinity of the third binding site for its target as defined above have the effect that the molecule according to the invention is capable of binding tightly and specifically to the tumor cell to be eliminated and the effector cell; the much lower affinity of the third binding site for its target is not sufficient to cause stable association with other cells that the molecule may encounter before or after binding to the tumor cell and/or the effector cell, but only allows the molecule according to the invention to locally inhibit checkpoint signaling between the tumor cell and the effector cell by competitively inhibiting the interaction between the checkpoint receptor and the checkpoint receptor ligand. As a consequence, side effects due to inhibition of checkpoint signaling on other cells are reduced.

FIG. 2B shows an exemplary embodiment that illustrates how a molecule with affinities as described above may be achieved. The depicted molecule comprises an scFv as first module (which includes the first binding site providing specificity for the tumor cell to be eliminated), an scFv as second module (which includes the second binding site for recruitment of the immune cell) and a third module formed from an endogenous extracellular domain (EED) of a checkpoint receptor, e.g. of SIRPα, with only a low to medium physiological affinity for its checkpoint receptor ligand (in the example of SIRPα: for CD47). In contrast to e.g. a triplebody format consisting of three scFvs on one polypeptide chain, this special combination allows the molecule to be highly specific for tumor and effector cells on one hand, while only locally affecting immune checkpoint signaling by local competition with the checkpoint receptor or checkpoint receptor ligand.

In some embodiments, said cell surface molecule at the cell surface of said tumor cell is selected from the group consisting of CD33, CD19, CD20, Her2/neu, CD123, CEA (carcinoembryonic antigen) and EpCAM (epithelial cell adhesion molecule) (see Table 2). Preferably, said cell surface molecule at the cell surface of said tumor cell is CD33.

As the skilled person will be aware, said cell surface molecule at the cell surface of said immune cell(s) (i.e. the cell surface molecule which said second binding site is capable of binding to) should not be an immune checkpoint molecule.

In some embodiments, said cell surface molecule at the cell surface of said immune cell(s) is selected from the group consisting of CD3, TCRαβ, CD16, NKG2D, NKp30, NKp40, LFA1, CD89, CD64, CD32a and CD15a (see Table 3).

Preferably, said cell surface molecule at the cell surface of said immune cell(s) is CD16 or CD3.

In some embodiments, binding of said second binding site to said cell surface molecule at the cell surface of said immune cell/immune cells sends an activation-inducing signal to said immune cell. Preferably, said second binding site is capable of binding to CD16 or CD3.

In some embodiments, said checkpoint molecule is selected from the group consisting of cytotoxic T lymphocyte-associated antigen 4 (CTLA4), signal regulatory protein alpha (SIRPα), PD-1, CD40 L and Tim3. Preferably, said checkpoint molecule is signal regulatory protein alpha (SIRPα).

In some preferred embodiments, said checkpoint molecule is selected from the group consisting of CD47, PD-L1, CD40, Gal9. Preferably, said checkpoint molecule is CD47.

In some preferred embodiments, said cell surface molecule at the cell surface of said tumor cell is CD33, said cell surface molecule at the cell surface of said immune cell(s) is CD16 and said checkpoint molecule at the cell surface of said tumor cell is CD47, wherein, preferably, said molecule comprises an antibody or a fragment of an antibody ("first antibody"/"first fragment of an antibody") which constitutes a part of said molecule (i.e. of said molecule according to the invention), wherein said first binding site of said molecule (i.e. of said molecule according to the invention) is formed by said antibody (i.e. by said "first antibody") or said fragment of an antibody (i.e. by said "first fragment of an antibody"), or said molecule comprises an scFv (single chain fragment variable) which constitutes a part of said molecule, wherein said first binding site of said molecule (i.e. of said molecule according to the invention) is formed by said scFv; and said molecule comprises an antibody or a fragment of an antibody ("second antibody"/"second fragment of an antibody") which constitutes a part of said molecule (i.e. of said molecule according to the invention), wherein said second binding site of said molecule (i.e. of said molecule according to the invention) is formed by said antibody (i.e. by said "second antibody") or said fragment of an antibody (i.e. said "second fragment of an antibody"), or said molecule comprises an scFv (single chain fragment variable) which constitutes a part of said molecule (i.e. of said molecule according to the invention), wherein said second binding site of said molecule (i.e. of said molecule according to the invention) is formed by said scFv; and said third binding site consists of the Ig like V type immunoglobulin like domain of the extracellular part of Sirp alpha (herein named SirpIg), wherein, preferably, said molecule comprises a further copy of said immunoglobulin-like domain of SIRPα.

A molecule with such binding specificities is able to target 1) CD33 as a specific maker expressed on AML cells; 2) CD16, expressed on NK cells and macrophages; and 3) CD47 for inhibition of the antiphagocytic "Don't eat me" checkpoint signal.

CD33 serves as a well-established target in AML therapy (Krupka et al., 2014; Petersdorf et al., 2013). It has further been used in a BiTE format demonstrating significant inhibition of tumor growth (Aigner et al., 2013). The molecule as defined above can be used as a successful tool in AML therapy engaging NK cells and macrophages instead of T cells. Locally blocking the "Don't eat me" immune checkpoint of macrophages is beneficial for tumor clearance.

SirpIg-anti-CD16-anti-CD33 and SirpIg-SirpIg-anti-CD16-anti-CD33 are particularly advantageous (and therefore intended) for the treatment of AML patients whose cancer returned after treatment (relapsed) or who did not respond to previous treatment (refractory).

In some embodiments, said molecule is a protein. Preferably, said third binding site is located N-terminally of said first binding site and said second binding site or C-terminally of said first binding site and said second binding site. This has the advantage that, if the third binding site has a lower binding affinity for its target molecule than the first binding site for its target molecule and than the second binding site for its target molecule, the mechanical forces exerted on the linkage between the tumor cell to be eliminated and the immune cell cannot disrupt the interaction of the third binding site with its target molecule.

In some embodiments, said molecule further comprises a fourth binding site, wherein said fourth binding site is capable of specifically binding to a cell surface molecule at the cell surface of said tumor cell.

Preferably, said cell surface molecule to which said fourth binding site is capable of specifically binding is the same as the cell surface molecule to which said first binding site is capable of specifically binding. Inclusion of two binding sites which specifically bind to the same cell surface molecule at the cell surface of the tumor cell to be eliminated allows to increase the affinity of the molecule according to the invention for the tumor cells to be eliminated.

Alternatively, cell surface molecule to which said fourth binding site is capable of specifically binding is a different cell surface molecule than the cell surface molecule to which said first binding site is capable of specifically binding. Preferably, the combination of said cell surface molecule to which said first binding site is capable of specifically binding and said cell surface molecule to which said fourth binding site is capable of specifically binding is specific for said tumor cell. By including in the molecule according to the invention two binding sites (the first and the fourth binding site) which specifically bind to different cell surface molecules at the cell surface of the tumor cell to be eliminated, the specificity of the molecule according to the invention for the tumor cells to be eliminated is increased.

In some embodiments, said molecule comprises an antibody or a fragment of an antibody ("first antibody"/"first fragment of an antibody") which constitutes a part of said molecule (i.e. of said molecule according to the invention), wherein said first binding site of said molecule (i.e. of said molecule according to the invention) is formed by said antibody (i.e. by said "first antibody") or said fragment of an antibody (i.e. by said "first fragment of an antibody"). This may for example be achieved by providing an antibody with binding specificity for a cell surface molecule at the cell surface of the tumor cell to be eliminated (or a fragment of such an antibody which fragment is still capable of specifically binding to said cell surface molecule at the cell surface of said tumor cell to be eliminated) and covalently linking said antibody (or said fragment thereof) to a domain that specifically binds to an immune cell and a domain that specifically binds to a checkpoint molecule.

In some embodiments, said molecule comprises an amino acid sequence ("first amino acid sequence") that has a length of at least 25 amino acids and that is at least 80%, preferably at least 88%, more preferably at least 92%, more preferably at least 96%, more preferably 100% identical to the amino acid sequence of an antibody, wherein, preferably, said amino acid sequence (i.e. said "first amino acid sequence") forms said first binding site or forms part of said first binding site.

In some embodiments, said molecule comprises an scFv (single chain fragment variable) which constitutes a part of said molecule, wherein said first binding site of said molecule (i.e. of said molecule according to the invention) is formed by said scFv.

In some embodiments, said molecule further comprises a second copy of said second binding site (i.e. another "second binding site" of the same structure and further characteristics as the first "second binding site"). By including in the molecule according to the invention two "second binding sites" which specifically bind to the same cell surface molecule at the cell surface of the immune cell(s), the affinity of the molecule according to the invention for the immune cell(s) to be recruited is increased.

In some embodiments, said molecule comprises an antibody or a fragment of an antibody ("second antibody"/"second fragment of an antibody") which constitutes a part of said molecule (i.e. of said molecule according to the invention), wherein said second binding site of said molecule (i.e. of said molecule according to the invention) is formed by said antibody (i.e. by said "second antibody") or said fragment of an antibody (i.e. said "second fragment of an antibody").

In some embodiments, said second binding site comprises an amino acid sequence ("second amino acid sequence") that has a length of at least 25 amino acids and that is at least 80%, preferably at least 88%, more preferably at least 92%, more preferably at least 96%, more preferably 100% identical to the amino acid sequence of an antibody, wherein, preferably, said amino acid sequence (i.e. said "second amino acid sequence") forms said second binding site or forms part of said second binding site.

In some embodiments, said molecule comprises an scFv (single chain fragment variable) which constitutes a part of said molecule (i.e. of said molecule according to the invention), wherein said second binding site of said molecule (i.e. of said molecule according to the invention) is formed by said scFv.

In some embodiments, said molecule comprises an Fc fragment of an antibody which constitutes a part of said molecule (i.e. of said molecule according to the invention), wherein said second binding site of said molecule (i.e. of said molecule according to the invention) is formed by said Fc fragment of an antibody.

In some embodiments, said molecule comprises an Fc fragment of an antibody which constitutes a part of said molecule (i.e. of said molecule according to the invention), wherein said second binding site of said molecule (i.e. of said molecule according to the invention) is formed by said Fc fragment of an antibody, wherein said cell surface molecule at the cell surface of an immune cell/immune cells is an Fc receptor. This has the advantage that binding of the molecule according to the invention to a Fc receptor molecule on said immune cell allows not only to recruit the immune cell to the tumor cell, but at the same time also activates the immune cell by signaling through Fc receptors and thus promotes destruction of the tumor cell.

In some embodiments, said molecule further comprises a second copy (and, possibly, even a third copy) of said third binding site (i.e. another "third binding site" having the same structure as the first "third binding site"). By including in the molecule according to the invention two (or even three) "third binding sites" which specifically bind to the same checkpoint molecule, one molecule according to the invention can bind to two (or even three) checkpoint molecules. This has the effect that an increased overall affinity of the molecule according to the invention for the cell carrying the checkpoint molecule at its cell surface is achieved, even if the individual binding affinity of one third binding site for its target is low. Moreover, the efficiency of checkpoint signaling inhibition is increased, because each molecule according to the invention can block/inhibit two (or even three) checkpoint receptor molecules.

In some embodiments, said molecule comprises an antibody or a fragment of an antibody ("third antibody"/"third fragment of an antibody") which constitutes a part of said molecule (i.e. of said molecule according to the invention), wherein said third binding site of said molecule (i.e. of said molecule according to the invention) is formed by said antibody (i.e. by said "third antibody") or said fragment of an antibody (i.e. said "third fragment of an antibody").

In some embodiments, said third binding site comprises an amino acid sequence ("third amino acid sequence") that has a length of at least 25 amino acids and that is at least 80%, preferably at least 88%, more preferably at least 92%, more preferably at least 96%, more preferably 100% identical to the amino acid sequence of an antibody, wherein, preferably, said amino acid sequence (i.e. said "third amino acid sequence") forms said third binding site or forms part of said third binding site.

In some embodiments, said molecule comprises an scFv (single chain fragment variable) which constitutes a part of said molecule (i.e. of said molecule according to the invention), wherein said third binding site of said molecule (i.e. of said molecule according to the invention) is formed by said scFv.

In some embodiments, said third binding site of said molecule (i.e. of said molecule according to the invention) is not formed by an antibody or a fragment of an antibody.

In some embodiments, said third binding site does not comprise an amino acid sequence that has a length of at least 25 amino acids and that is at least 80%, preferably at least 88%, more preferably at least 92%, more preferably at least 96%, more preferably 100% identical to the amino acid sequence of an antibody and that forms said third binding site or forms part of said third binding site.

In some embodiments, said third binding site of said molecule (i.e. of said molecule according to the invention) is not formed by an scFv.

In some embodiments, said molecule comprises a checkpoint receptor capable of binding to said checkpoint molecule or a fragment of a checkpoint receptor capable of binding to said checkpoint molecule, which checkpoint receptor/fragment of a checkpoint receptor constitutes a part of said molecule (i.e. of said molecule according to the invention), wherein said third binding site of said molecule (i.e. of said molecule according to the invention) is formed by said checkpoint receptor capable of binding to said checkpoint molecule or by said fragment of a checkpoint receptor capable of binding to said checkpoint molecule. Preferably, said checkpoint receptor capable of binding to said checkpoint molecule is SIRPα. Preferably, said fragment of a checkpoint receptor capable of binding to said checkpoint molecule is a fragment of SIRPα.

In some preferred embodiments, said third binding site is formed by a fragment of an immune cell checkpoint receptor, preferably by an endogenous extracellular domain (EED) of an immune cell checkpoint receptor, wherein, preferably, said molecule does not comprise any other part of said immune cell checkpoint receptor besides said endogenous extracellular domain. Preferably, said endogenous extracellular domain of an immune cell checkpoint receptor is an immunoglobulin-like domain of SIRPα (signal regulatory protein alpha). In some embodiments, said third binding site is formed by a fragment of SIRPα, preferably by an immunoglobulin-like domain of SIRPα, wherein, preferably, said molecule does not comprise any other part of said immune cell checkpoint receptor besides said immunoglobulin-like domain of SIRPα.

In some embodiments, said molecule comprises a checkpoint receptor ligand capable of binding to said checkpoint molecule or a fragment of a checkpoint receptor ligand capable of binding to said checkpoint molecule, which checkpoint receptor ligand/fragment of a checkpoint receptor ligand constitutes a part of said molecule (i.e. of said molecule according to the invention), wherein said third binding site of said molecule (i.e. of said molecule according to the invention) is formed by said checkpoint receptor ligand capable of binding to said checkpoint molecule or by said fragment of a checkpoint receptor ligand capable of binding to said checkpoint molecule. Preferably, said checkpoint receptor ligand capable of binding to said checkpoint molecule is CD47. Preferably, said fragment of a checkpoint receptor ligand capable of binding to said checkpoint molecule is a fragment of CD47.

In cases where the binding site(s) are antibody-derived (i.e. based on antibody sequence), a molecule according to the invention may be referred to as a "local inhibitory checkpoint antibody derivative" (liCAD).

In cases, where the molecules according to the present invention are based on a monoclonal antibody format i.e. they include at least one light chain at least one heavy chain, and optionally, further domains of an antibody, they may also be referred to as local inhibitory checkpoint monoclonal antibodies (licMAB).

In some embodiments, said molecule comprises a bispecific antibody which constitutes a part of said molecule (i.e. of said molecule according to the invention), wherein said first binding site and said second binding site of said molecule (i.e. of said molecule according to the invention) are formed by said bispecific antibody.

In some embodiments, said molecule comprises a BiTE (bispecific T cell engager) which constitutes a part of said molecule (i.e. of said molecule according to the invention), wherein said first binding site and said second binding site of said molecule (i.e. of said molecule according to the invention) is formed by said BiTE.

In some embodiments, said molecule has a molecular weight of below 300 kDa, preferably below 250 kDa, more preferably below 200 kDa, even more preferably below 150 kDa, even more preferably below 100 kDa.

In some embodiments, said tumor cell is a cell of a solid tumor. In some embodiments, said tumor cell is a cell of a non-solid tumor. In some embodiments, said tumor cell is a blood cancer cell, preferably a cell of an acute myeloid leukemia (AML).

In some embodiments, said molecule is for use as a medicament.

In some embodiments, said molecule is for use in the treatment of cancer, wherein, preferably said cancer comprises cancer cells that overexpress CD47 (i.e. said cancer cells express CD47 at their cell surface at a higher level than corresponding non-cancerous, healthy cells).

Preferably, said molecule is for use in the treatment of a cancer selected from the group consisting of AML (acute myeloid leukemia), B-ALL (B-cell acute lymphoblastic leukemia), NHL (non-Hodgkin B-cell lymphoma), pancreatic cancer, prostate cancer and bladder cancer, more preferably AML.

In some embodiments, said molecule is for administration to a patient in need thereof, wherein, preferably, said patient is a human.

Preferably, said patient is suffering from a tumor, more preferably from cancer (i.e. from a malignant tumor), more preferably from a blood cancer, even more preferably from AML (acute myeloid leukemia).

Preferably, said tumor cell is a cell of the tumor which said patient is suffering from. Preferably, said tumor cell is a cancer cell of the cancer which said patient is suffering from.

Preferably, said patient is suffering from AML and either the AML of said patient has returned after previous treatment (i.e. there was a relapse) or the patient did not respond to a previous treatment (i.e. the cancer was refractory). As the skilled person will appreciate, said previous treatment was not a treatment with the molecule according to the invention.

In one embodiment, said cancer is a cancer that overexpresses CD47. Preferably, said cancer is selected from the group consisting of AML, ALL, NHL, pancreatic cancer, prostate cancer and bladder cancer. More preferably, said cancer is AML.

In a second aspect, the present invention relates to a pharmaceutical composition comprising the molecule as defined in any of the embodiments above, wherein, preferably, said pharmaceutical composition further comprises a pharmaceutically acceptable carrier.

In a third aspect, the present invention relates to a method for treatment of a patient who is suffering from a tumor, preferably from cancer (i.e. from a malignant tumor), said method comprising the steps:

obtaining a molecule comprising
(i) a first binding site, wherein said first binding site is capable of specifically binding to a cell surface molecule at the cell surface of a tumor cell;
(ii) a second binding site, wherein said second binding site is capable of specifically binding to a cell surface molecule at the cell surface of an immune cell/immune cells;
(iii) a third binding site, wherein said third binding site is capable of specifically binding to a checkpoint molecule at the cell surface of said tumor cell or of said immune cell(s);
administering said molecule to said patient.

In such method for treatment, said tumor, said cancer, said patient, said molecule, said first binding site, said tumor cell, said cell surface molecule at the cell surface of said tumor cell, said second binding site, said immune cell/immune cells, said cell surface molecule at the cell surface of an immune cell/immune cells, said third binding site and said checkpoint molecule are preferably as defined in any of the embodiments above.

In a fourth aspect, the present invention relates to the use of a molecule as defined in any of the embodiments above for the manufacture of a medicament for the treatment of a patient suffering from a tumor, preferably of a patient suffering from cancer (i.e. from a malignant tumor).

In such use, said patient, said tumor and said cancer are preferably as defined in any of the embodiments above.

As used herein, the term "binding site" refers to a part or region of a molecule that is responsible for selective binding of said molecule to a target molecule of interest (e.g. an antigen, ligand, receptor or inhibitor).

At some instances, the present application indicates that a molecule or binding site A is "capable of specifically binding to" a certain binding partner, for example a molecule B. This is meant to designate that molecule or binding site A, in the presence of molecule B and other molecules, binds to molecule B, but does not bind in a significant amount to other molecules that lack the structural motive which molecule or binding site A interacts with in the structure of molecule B.

The term "specifically binds to" or "specifically binds", as used by the present invention in the context of a molecule A that specifically binds (to) an interaction partner B, means that a molecule A binds to said interaction partner B, preferably by non-covalent binding, or is capable of binding said interaction partner B, preferably by non-covalent binding, and does not or essentially not cross-react with any other interaction partner or molecule with a structure similar to that of the interaction partner B.

As used herein, a "cell surface molecule at the cell surface of a cell" is a molecule that is present (or at least part of which is present) at the exterior surface of said cell, such that the molecule may undergo a binding interaction with e.g. a soluble molecule that exists in the exterior environment of said cell or with a cell surface molecule at the cell surface of another cell that is spatially close to said cell. An example for a cell surface molecule at the cell surface of a cell is a transmembrane protein in the cell membrane of said cell or an integral membrane protein in the cell membrane of said cell with an extracellular domain that is accessible to other molecules from outside of said cell. If the present application indicates that a certain molecule "is present on the cell surface" of a certain cell or that a certain cell "carries on its cell surface" a certain molecule, this refers to the same situation as described above.

At some instances, the present application indicates that a certain cell surface molecule/molecule at the cell surface of a cell or combination of cell surface molecules "is specific" for a certain cell type. This means that said cell surface molecule/molecule at the cell surface or combination of cell surface molecules is highly present at the cell surface of said cell type, but present at a lower levels or not at all at the cell surface of other cell types. In some embodiments, it means that said cell surface molecule/molecule at the cell surface of a cell or combination of cell surface molecules is present at the cell surface of said cell type and at the cell surface of one or a few other cell types besides said cell type, but is not present (or only present at a negligible level) at the cell surface of other cell types. A cell surface molecule that is specific for a certain type of tumor cell is known as a "tumor marker".

If the present application refers to a "tumor cell", this may be a cell of a malignant or benign tumor (i.e. of a malignant or benign neoplasm). Preferably, the term "tumor cell" refers to a cell of a malignant tumor. Tumor cells can form a solid tumor, in which the tumor cells are massed together, or exist as dispersed cells, thus forming a non-solid tumor, as in leukemia. "Cancer" as used herein, refers to a diseases caused by the uncontrolled, abnormal growth of cells that can spread to adjoining tissues or other parts of the body. The cells of a cancer (such as the cells of a solid cancer, e.g. a breast cancer, or the cells of a blood cancer, e.g. a malignant B cell tumor) are malignant tumor cells.

As used herein, an "immune cell" is a cell of hematopoietic origin that plays a role in the immune response. The term includes lymphocytes (such as B cells and T cells), natural killer cells and myeloid cells (such as monocytes, macrophages, eosinophils, mast cells, basophils, and granulocytes).

As used herein, the term "CD16" refers to the Fc receptor FcγRIIIa as well as the Fc receptor FcγRIIIb. Preferably, the term refers to the Fc receptor FcγRIIIa. The Fc receptor FcγRIIIa (CD16a) is present in particular at the cell surface of NK cells and macrophages, the Fc receptor FcγRIIIb (CD16b) at the cell surface of neutrophils.

A "checkpoint molecule", as used herein, is a molecule involved in immune checkpoint signaling of an immune cell, wherein a checkpoint molecule may either be a "checkpoint receptor" or "immune checkpoint receptor" (i.e. a receptor at the cell surface of an immune cell regulated by said immune checkpoint signaling) or a "checkpoint receptor ligand" (i.e. a ligand of such a checkpoint receptor, typically at the cell surface of another cell). Binding of the checkpoint receptor ligand to the immune checkpoint receptor sends an inhibitory/antiphagocytic signal to the immune cell and thus prevents the immune cell from becoming activated and attacking/phagocytosing the cell carrying the checkpoint receptor ligand at its cell surface. Examples of checkpoint receptors are SIRPα (signal regulatory protein alpha), PD-1, CTLA4, CD40L and TIM3. Examples of checkpoint receptor ligands are CD47, PD-L1, CD80/CD86, CD40, Gal9.

An endogenous extracellular domain (EED) of an immune cell checkpoint receptor is a domain or part of said immune checkpoint receptor that is located outside of the immune cell and that is able to bind to the corresponding checkpoint receptor ligand of said immune checkpoint receptor. Endogenous SIRPα checkpoint receptor, for example, comprises three extracellular immunoglobulin-like domains which form the EED of SIRPα checkpoint receptor; this EED of SIRPα checkpoint receptor mediates binding of SIRPα checkpoint receptor to its checkpoint receptor ligand CD47. Specifically, binding of SIRPα checkpoint receptor to its checkpoint receptor ligand CD47 is mediated by the N-terminal immunoglobulin-like domain of SIRPα. The designations "SIRPα-Ig", "SIRP-Ig" and "SirpIg" are used interchangeably and refer to a CD47-binding immunoglobulin-like domain of SIRPα.

The phrase "single chain fragment variable" or "scFv" refers to an antibody derivative in which the variable domains of the heavy chain and of the light chain of a conventional antibody have been joined to form one chain. Typically, a linker peptide is inserted between the two chains to allow for proper folding and creation of an active binding site.

As used herein, the term "overexpress", as used e.g. in the context of a certain tumor cell that "overexpresses" a certain molecule, means that said molecule is expressed by said tumor cell (such as a malignant B-cell tumor cell) at a higher rate or amount than by a cell of the corresponding non-tumoral cell type (such as a normal, non-malignant B-cell), wherein the cell of the corresponding non-tumoral cell type does not (or only to a negligible extent) express that molecule or, in some embodiments, has a small but detectable expression of said molecule which, however, is lower than the expression of said molecule by said tumor cell.

At some instances, the present application defines that the affinity of a certain binding site A for a certain molecule X is "higher" than the affinity of another binding site B for a certain molecule Y by a certain factor. In this context, "higher" affinity refers to stronger binding, and thus to a lower $K_d$ value (dissociation constant). Hence, if the affinity of binding site A for a molecule X is higher than the affinity of binding site B for molecule Y by at least a factor of 10, this means that, in a situation where the $K_d$ for the interaction of binding site A with molecule X is 1 mM, the $K_d$ for the interaction of binding site B with molecule Y is ≥10 mM.

If the present application states that the affinity of a certain binding site or molecule for a certain molecule "is within a certain range from x to y", this means that the dissociation constant ($K_d$) of said interaction at physiological conditions is ≥x and ≤y.

If the present application refers to a specific affinity or ratio of affinities, this refers to affinities measured by flow cytometry (This may be done with cells that express only the target of the domain to be measured, not the targets of the other domains of the molecule according to the invention. For example, if the molecule according to the invention is SIRP-Ig-αCD16-αCD33 and the affinity of the αCD33 domain to CD33 is to be measured, cells expressing at their cell surface CD33, but not CD16 or CD47, should be used. Molecules according to the invention bound to the cells may for example be detected by inclusion of a his tag in the molecule according to the invention and detection of the his tag with a labelled anti-his-tag antibody. The $K_d$ can be determined by classical methods of $K_d$ determination known to the skilled person upon measuring binding at different concentrations of the molecule according to the invention.) or, if this is not possible, surface plasmon resonance measurements (immobilization of the target on the surface, molecule according to the invention as ligand).

Unless indicated otherwise, any binding specificities or affinities referred to in the present application refer to the binding specificity/affinity measured in PBS (phosphate buffered saline), pH 7.4, comprising 1% bovine serum albumin and 0.1% sodium azide, at room temperature.

If the present application states that binding of a certain binding site or molecule to a certain cell surface molecule at the cell surface of an immune cell causes activation of said immune cell, this refers to a situation where upon binding of said binding site or molecule to said cell surface molecule the phagocytic and/or cytotoxic activity of said immune cell is increased.

If the present application indicates that a certain molecule "is a protein", this means that said molecule or parts of said molecule consist of a polymeric chain of amino acids. Preferably, the term designates that the said entire molecule consists of a polymeric chain of amino acids.

The term "pharmaceutically acceptable carrier" refers to a non-toxic, inert, solid, semi-solid, or liquid diluent material or formulation auxiliary of any type. "Pharmaceutically acceptable" in this context is meant to designate that said carrier is compatible with the other ingredients of the pharmaceutical composition and not harmful to the patient that the pharmaceutical composition is administered to. Examples of pharmaceutically acceptable carriers include, but are not limited to, water-propylene glycol solutions, or aqueous polyethylene glycol solutions.

The production of medicaments or pharmaceutical compositions containing a molecule according to the present invention and their application can be performed according to well-known pharmaceutical methods.

The term "patient who is suffering from a tumor", as used herein, refers to a subject who has been tested and found to have tumor cells in his/her body. The term "patient who is suffering from cancer", as used herein, refers to a subject who has been tested and found to have cancer cells in his/her body. The presence of tumor/cancer cells may be diagnosed using any suitable method, including but not limited to, biopsy, x-ray, blood test, etc.

The present inventors have surprisingly found that a molecule according to the invention that comprises a binding site that allows for specific targeting of tumor cells, a binding site that allows to recruit an immune cell as effector cell and a binding site that allows for local checkpoint inhibition (e.g. in a multi-specific antibody derivative including such three binding sites) provides for tumor specific effector cell recruitment and efficient killing of said tumor cells while keeping the systemic blocking of said checkpoint at a minimum, and thus allows for treatment of cancer while reducing the side effects.

Moreover, the present inventors have found that if the molecule according to the invention includes a third binding site with only a low affinity for its checkpoint molecule target and/or includes a third binding site which has a much weaker affinity for its target molecule than the affinity of the first and second binding sites for their respective target molecules, this leads to surprising effects with regard to a further reduction of systemic side effects (which otherwise may still occur to some degree through immune cells attacking other cells besides the tumor cells to be targeted).

In the following, reference is made to the figures:

All methods mentioned in the figure descriptions below were carried out as described in detail in the examples.

FIGS. 1A-1C show a schematic depiction of a conventional mAB and scFv constructs.

(1A) Conventional IgG antibody. 1: Fab (fragment antigen binding); 2: Fc (fragment crystallizable); 3: Fv (fragment variable): variable domain of heavy and light chain; 4: antigen binding region.

(1B) scFv (single chain fragment variable): Heavy and light chain are connected by a flexible linker.

(1C Single chain bispecific molecule: Two different scFvs connected with flexible linker, resulting in a bispecific molecule comprising two scFv.

FIGS. 2A-2B show a schematic overview of autonomous modules within an exemplary embodiment of the molecule according to the invention indicating (2A) the function of the different modules and (2B) examples for domains that may be used for these modules.

Module 1 comprises the first binding site and mediates specific binding to the tumor cell to be eliminated through a cell surface molecule of the tumor cell. Module 1 can for example be an scFv that specifically binds to a tumor antigen at the cell surface. This domain is connected by a flexible linker to module 2, which mediates effector cell recruitment and can for example be an scFv that specifically binds to an immune cell, such as a macrophage cell.

Module 3 comprises a binding site that specifically binds to a checkpoint molecule on the immune cell or the tumor cell. For example, module 3 may be formed by the endogenous extracellular domain (EED) of an immune checkpoint receptor. For example, the EED of the immune checkpoint receptor SIRPα on immune cells binds specifically to its immune checkpoint ligand, the transmembrane protein CD47, on cells encountering the immune cell. Upon binding of module 1 to the tumor antigen and of module 2 to the effector cell (i.e. the immune cell), the effector cell and tumor cell are brought into close vicinity. Binding of module 3 to the checkpoint molecule prevents checkpoint signaling and thus activation of the effector cell will cause elimination of the tumor cell.

(Note: According to the present invention, different orders of the different modules within the molecule according to the invention are considered, including, but not limited to, the exemplary orders shown in FIG. 2A.)

FIGS. 3A-3C show a schematic illustration of checkpoint signaling and immune surveillance in cancer in the absence or presence of different forms of treatment.

(3A) Checkpoint signaling in the absence of treatment. The tumor cell overexpresses CD47 at its cell surface. Due to binding of CD47 to Sirpα at the cell surface of the effector cell (immune cell), the effector cell receives an antiphagocytic signal and thus does not phagocytose the tumor cell.

(3B) In certain conventional treatments, two antibodies are applied: A tumor-specific mAb binds to a tumor antigen at the surface of the tumor cell. The Fc region of the tumor-specific mAb binds to an Fcγ receptor at the cell surface of the immune cell. This recruits the immune cell to the tumor cell (and also sends, upon engagement of Fcy receptor, an additional activation signal to the effector cell). At the same time, an anti-CD47 mAb is administered that binds to CD47 at the cell surface of the tumor cell. This prevents binding of CD47 to Sirpα at the cell surface of the immune cell and thus prevents the tumor cell from sending an antiphagocytic checkpoint signal to the immune cell. Thus, the effector cell destroys the tumor cell. However, the anti-CD47 mAbs bind not only to CD47 molecules on the tumor cell, but also to CD47 molecules on other cell types. Consequently, severe systemic side effects because of effector cell activity against such other cell types might be observed.

(3C shows examples of treatment with molecules according to the present invention.

Left: A molecule according to the present invention contains a module (e.g. a scFv) binding to a tumor antigen, a module (e.g. a scFv) binding to an Fcy receptor on the effector cell, and a module (which may e.g. be formed by one, two (or n) Sirp-Ig domains) binding to CD47 on the tumor cell. Simultaneous binding of the molecule to the tumor antigen on the tumor cell and the Fcγ receptor on the effector cell recruits the effector cell to the tumor cell. The binding of the CD47-binding module to CD47 at the cell surface of the tumor cell prevents antiphagocytic checkpoint signaling to the immune cell. Thus, the effector cell kills the tumor cell. Since the Sirp-Ig domains are part of the same molecule as the tumor targeting and the effector cell recruitment/activation modules, inhibition of checkpoint signaling occurs locally. Accordingly, systemic side effects are reduced compared to the treatment in (B).

Right: A molecule according to the present invention contains an antibody with binding specificity to a tumor marker on the tumor cell. The antibody is linked to two domains binding to CD47 on the tumor cell (in this case, each of the antibody "arms" is linked through its light chain to a Sirp-Ig). By binding to a tumor antigen on the cell surface of the tumor cell and to an Fcγ receptor on the effector cell, the effector cell is recruited to the tumor cell. At the same time, binding of the two Sirp-Ig domains to CD47 molecules at the cell surface of the tumor cell efficiently prevents binding of CD47 to the Sirpα receptor and thus prevents the tumor cell from sending an antiphagocytic checkpoint signal to the effector cell. As a consequence, the effector cell destroys the tumor cell. Again, the Sirp-Ig domains are part of the same molecule as the tumor targeting and the effector cell recruitment modules. Hence, inhibition of checkpoint signaling occurs only locally and systemic side effects are reduced compared to the treatment in (B).

Figure 4A:
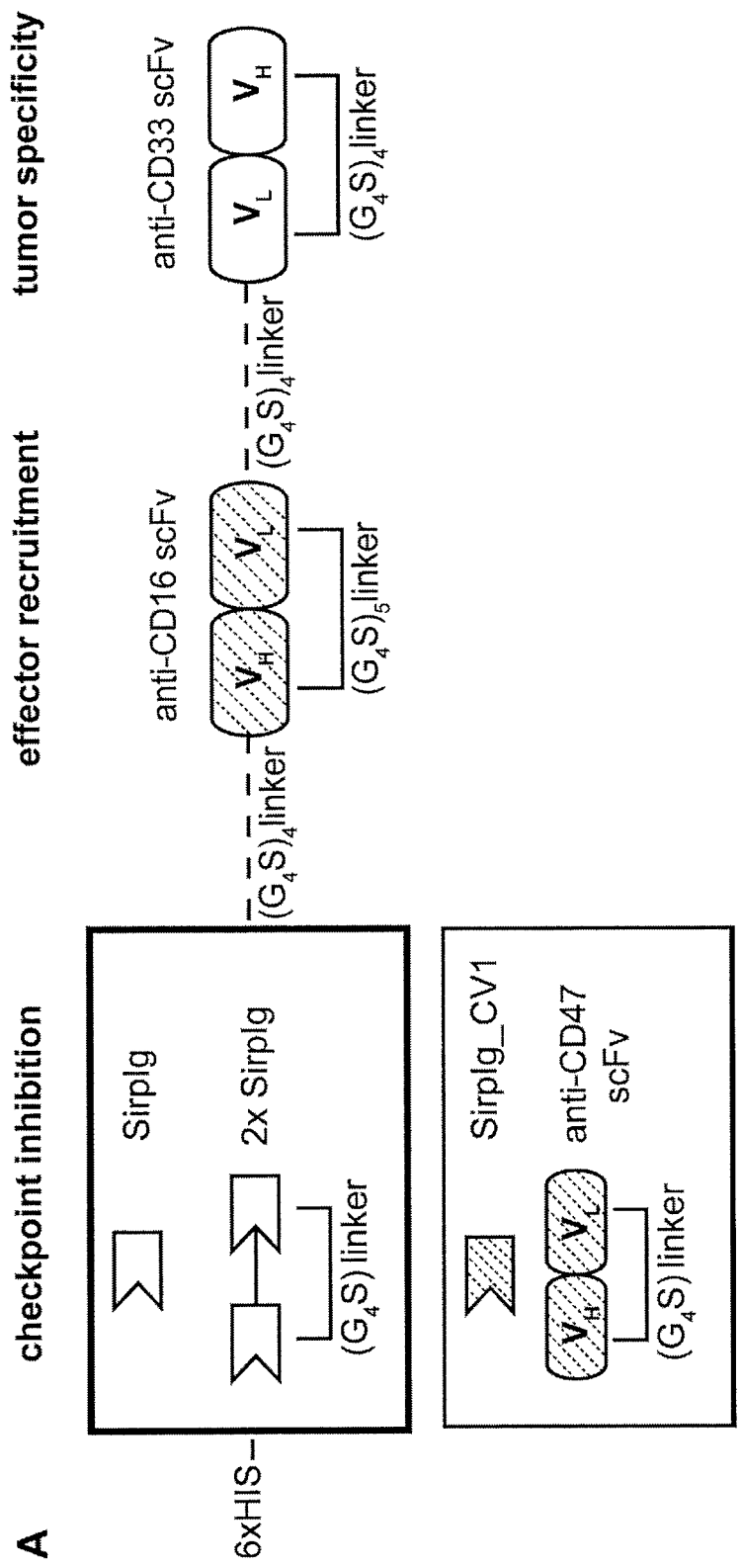
Figure 4B:
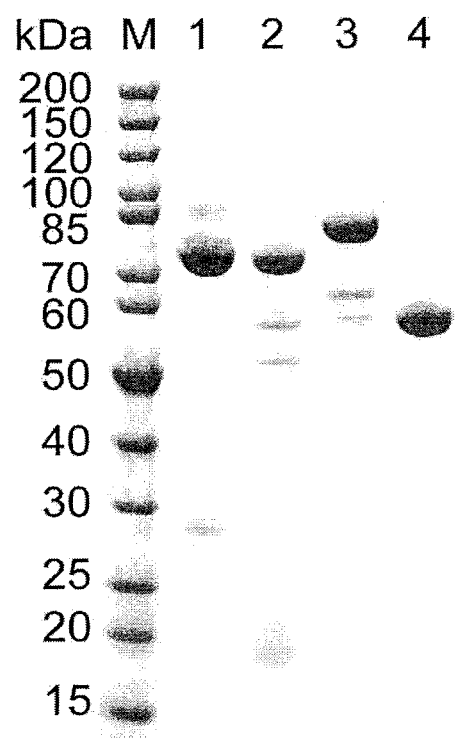

FIGS. 4A-4B show the construct design and an expression analysis of the liCADs prepared in Example 1.

(4A) Schematical view of different constructs used in this study. The constructs consist of an N-terminal hexa-histidine tag (6×HIS), followed by different approaches to target CD47 (shown within the upper black box, the lower box displays control molecules). The central anti-CD16 as well as the anti-CD33 domain remain unchanged in all constructs.

(4B) SDS-PAGE analysis of purified proteins (1) SIRPα-αCD16-αCD33, (2) SIRPα_CV1-αCD16-αCD33, (3) αCD47-αCD16-αCD33 and (4) αCD16-αCD33. (M) molecular weight marker.

FIGS. 5A-5F show experimental data generated by FACS analysis, confirming binding of individual modules of liCADs to their antigens or ligands, respectively.

(5A) HEK cells show binding of SIRPα_CV1, (5B) MOLM-13 cells show binding of anti-CD47 scFv and (5C) THP-1 cells show binding of anti-CD33 scFv. (SD) To demonstrate the binding of the anti-CD16 scFv CHO cells, stably transfected with CD16, were used. (SE) FACS analysis did not allow for the detection of SIRPα binding to CD47 on Jurkat cells.

FIGS. 6A-6C show experimental data generated by FACS analysis to determine the dissociation constant (KD values) using highly over-expressing stable CHO cell lines.

(6A) Top: FACS Analysis of SirpIg.CD16.CD33 and SirpIg.SirpIgCD16.CD33 binding to CHO cells highly over-expressing CD47 (CHO.exCD47). Bottom left: CHO-.exCD47 cells were used to determine KD values of SirpIg.SirpIg.CD16.CD33. Bottom right: and KD values of SirpIg.CD16.CD33.

(6B) Top: Binding of anti-CD33 within the SirpIg.CD16.CD33 molecule was analysed by FACS analysis using CD33 over-expressing CHO cells (CHO.exCD33). Bottom: KD-values were determined for anti-CD33 scFV using CHO.exCD33 cells.

(6C) Top: Again binding of anti-CD16 to CD16 overexpressing CHO (CHO.exCD16) cells shown by FACS analysis. Bottom: KD values were determined for anti-CD16 scFv using CHO.exCD16 cells.

Figure 7A:
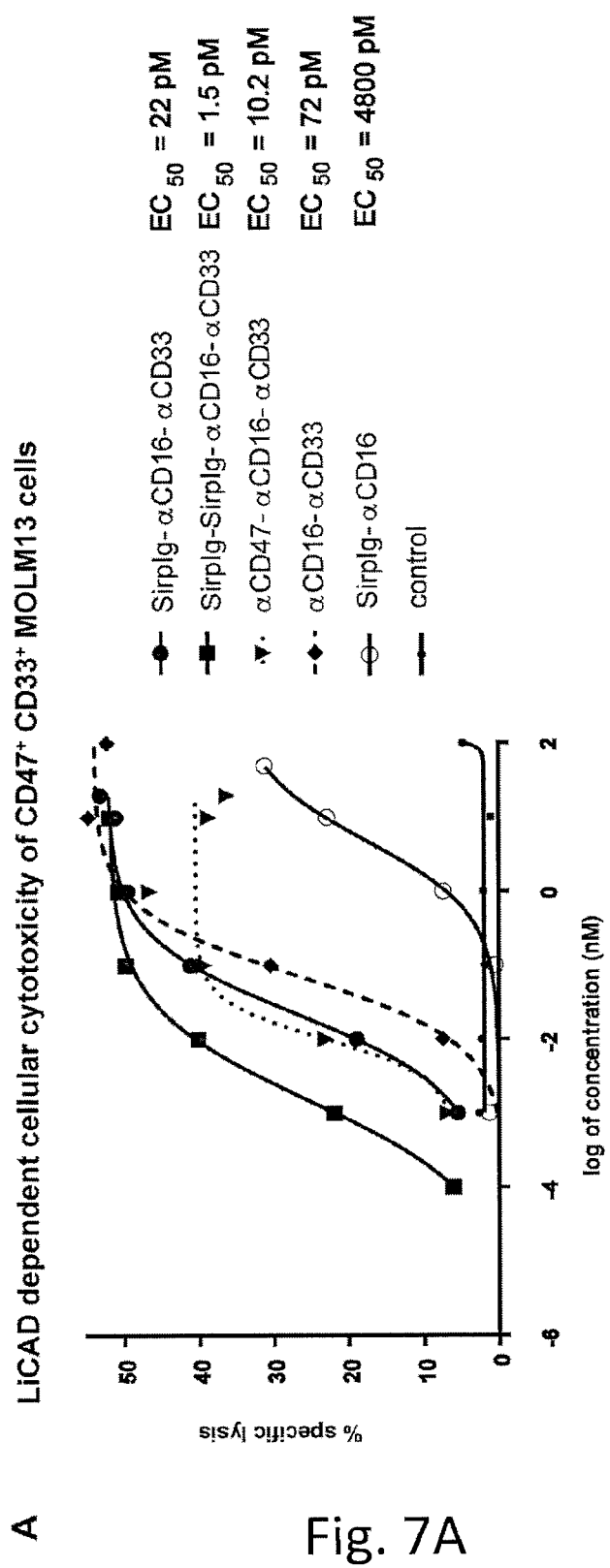

FIGS. 7A-7C shows data obtained from a redirected lysis (RDL) assay testing the dose-dependent induction of redirected lysis of MOLM 13 and HEK 293T cells.

(7A) LiCAD dependent cellular cytotoxicity of CD47+/CD33+ MOLM-13 target cells. Killing efficiency correlates with affinities for CD47.

(7B) Calcein-AM labeled HEK CD47 single positive cells, mixed with unlabeled HEK CD47/CD33 double positive cells, were used as targets to compare efficacy of liCADs and control molecules at a constant effector:target ratio of 2:1 at maximal protein concentrations. In a parallel reaction unlabeled HEK CD47 single positive cells, mixed with Calcein-AM labeled HEK CD47/CD33 double positive cells were used as targets to compare efficacy of liCADs and control molecules at a constant effector:target ratio of 2:1 as well at maximal protein concentrations. % specific lysis was analysed and demonstrates the potential of liCADs to preferentially kill double positive target cells.

(7C) Calcein-AM labeled HEK CD47 single positive cells, mixed with unlabeled HEK CD47/CD33 double positive cells, were used as targets to compare efficacy of liCADs and control molecules at a constant effector-target ratio of 2:1 at $EC_{50}$ values. In a parallel reaction unlabeled HEK CD47 single positive cells, mixed with Calcein-AM labeled HEK CD47/CD33 double positive cells were used as targets to compare efficacy of liCADs and control molecules at a constant effector:target ratio of 2:1 as well at $EC_{50}$ values. % specific lysis was analysed and demonstrates the potential of liCADs to preferentially kill double positive target cells.

Figure 8:
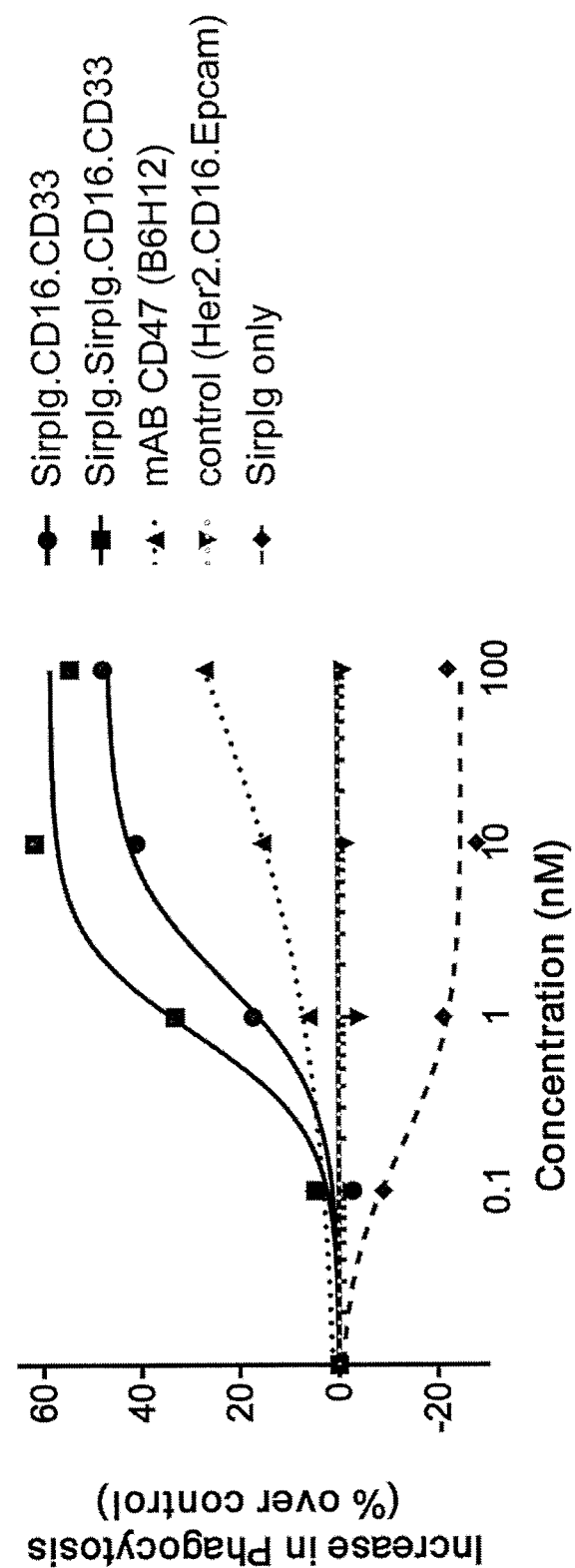

FIG. 8 shows the increase in phagocytosis of MOLM-13 target cells in a dose-response manner for liCADs and controls.

Figure 9:
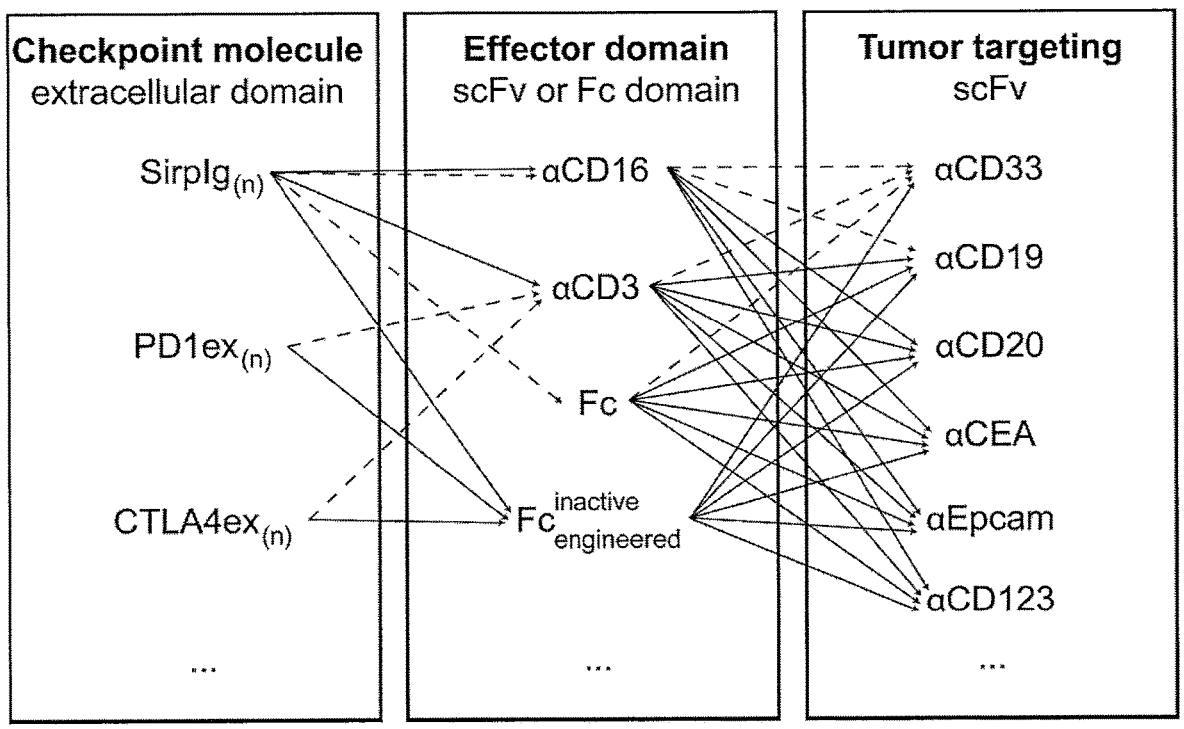

FIG. 9 shows some liCAD formations (i.e. combinations of (a) a domain providing a first binding site capable of specifically binding to a cell surface molecule at the cell surface of said tumor cell, (b) a domain providing a second binding site capable of specifically binding to a cell surface molecule at the cell surface of said immune cell(s), and (c) a domain providing a third binding site capable of specifically binding to a checkpoint molecule) considered by the present application. Particularly preferred combinations are indicated by dashed lines.

FIG. 10 shows a summary of experimental data for molecules according to the invention. Additional licCAD and licMAB molecules targeting CD33, interfering with CD47, and effector cell function, according to the invention were expressed and tested in different experiments. The summary includes monoclonal antibody (mAB) formats and Fc-engineered variants thereof (for control, high affinity variants), licMABs as described in Table 4 and Fc-engineered variants thereof, bispecific licMABs and liCADs as indicated in Table 4. Fc-engineered variants of bispecific licMABs are currently under development. The summary includes measurements for thermo stability (thermofluor assays, Tm), binding to the recombinantly expressed extracellular domain of CD16 (exCD16) analyzed by size exclusion chromatography (SEC), binding to MOLM-13 cells ($K_D$ determination), internalization of liCADs and licMABs, antibody-dependent cellular cytotoxicity (ADCC) and antibody-dependent cellular phagocytosis (ADCP) assays at 100 nM (shown as % of phagocytosis). n.d.=not determined; "a" in the figure represents "anti" (as in antibody fragment, e.g. scFv).

FIGS. 11A-11B show original data obtained from thermal stability assays. The thermal stability of the indicated molecules was determined by fluorescence thermal shift assays using the CFX96 Touch Real-lime PCR Detection System. 10 μg of protein containing 1× SYPRO Orange were measured using FAM and SYBR Green I filter pairs. All molecules show reasonable thermo stability in the performed assay.

(11A) Thermal stability assays for αCD33 mAB and licMABs (SirpIg.αCD33 and SirpIg. SirpIg.αCD33; upper panel) and Fc-engineered variants thereof (lower panel).

(11B) Thermal stability assays of liCADs (upper panel) and bispecific licMABs (lower panel)

FIG. 12 exemplary shows data on binding of a SirpIg.SirpIg.αCD33 licMAB and a Fc-engineered variant thereof to the recombinantly expressed extracellular domain of CD16 (exCD16) analyzed by size exclusion chromatography (SEC). As summarized in FIG. 10 control mABs, licMABs and Fc-engineered variants thereof were tested for their binding ability to exCD16 by SEC. As indicated in Table 4 conventional antibodies have a rather low affinity to Fc receptors in comparison to Fc-engineered variants which have a much higher affinity. As exemplarily shown in this figure conventional Fc domains do not form a stable complex with exCD16 (upper panel) in contrast to Fc-engineered variants (lower panel) measured by SEC. Co-migration of exCD16 with the Fc-engineered molecules is validated by SDS-PAGE. Conclusively, conventional Fc domains of IgG1 molecules have low affinity to exCD16 and thus do not form a stable complex as shown by SEC. Fc-engineered mABs and licMABs however, can recruit effector cells or cells expressing Fc receptors with higher affinity.

FIGS. 13A-13B show the $K_D$ determination as an avidity value of different molecules indicated in this invention. All molecules tested show binding to target antigen expressing cells in the nM range.

(13A) Binding analysis of αCD33 mAB, SirpIg.CD33 and SirpIg.SirpIg.αCD33 licMABs to MOLM-13 cells measured by flow cytometry (upper panel). $K_D$ determination of Fc-engineered variants of αCD33 mAB and licMABs (lower panel). Mean values and SEM (error bars) are plotted and $K_D$ values are indicated.

(13B) $K_D$ determination of liCADs (upper panel) and bispecific licMABs (lower panel). Mean values and SEM (error bars) are plotted and $K_D$ values are indicated.

Figure 14:
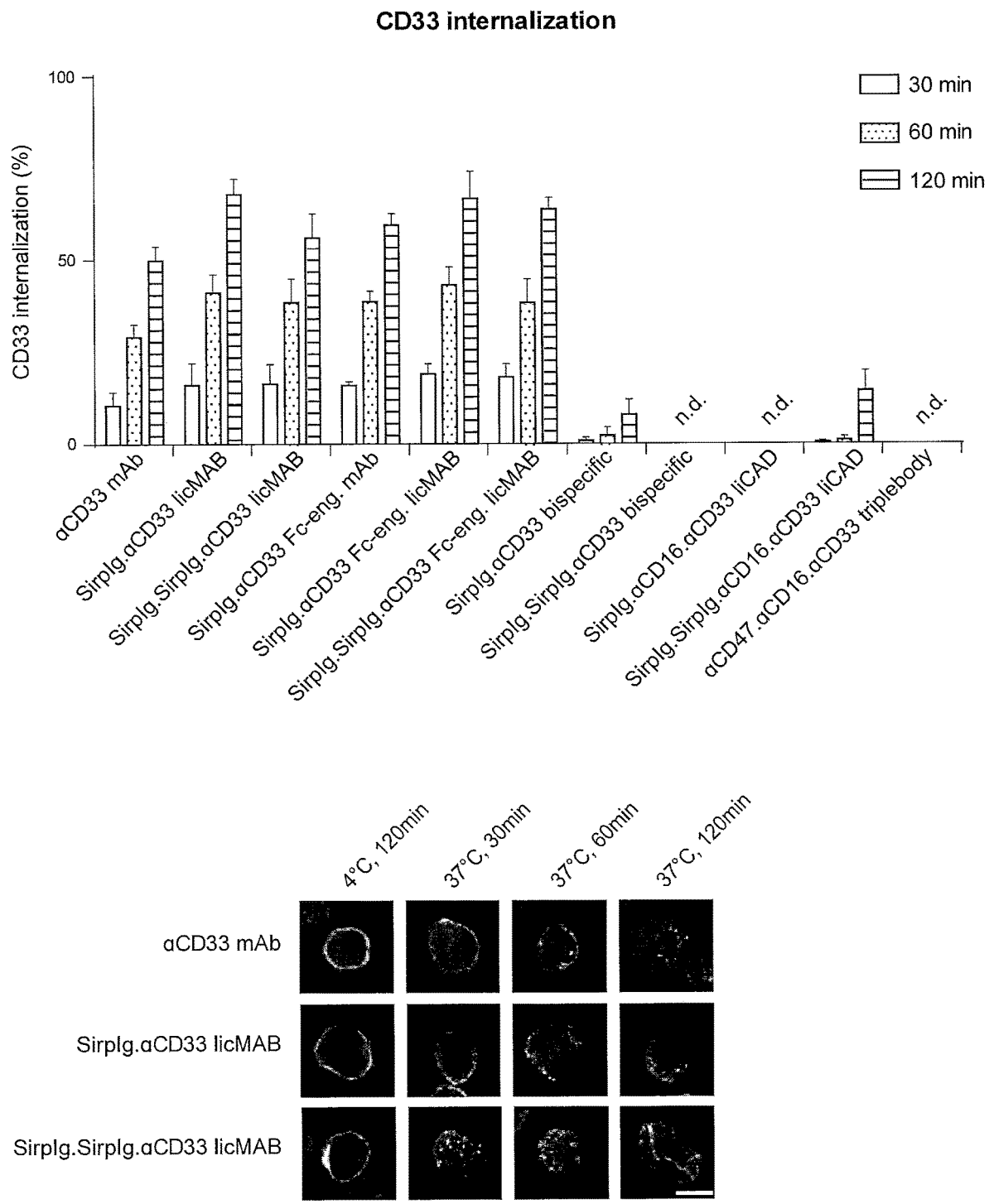

FIG. 14 shows data obtained from internalization assays. MOLM-13 cells were incubated with 15 μg/ml of licMABs or mAb either on ice-cold water for 2 h (to prevent internalization) or at 37° C. for 30, 60 or 120 min. Cells were then washed with ice-cold FACS buffer and antibodies remaining on the surface were detected by staining with FITC αHuman IgG Fc. To define the background fluorescence, MOLM-13 cells were directly stained with the secondary antibody. % of CD33 internalization is indicated (upper panel). Internalization was co-evaluated by confocal fluorescence microscopy (lower panel). Scale bar=10 μm. As expected, bivalent binding of CD33 causes internalization of mABs and licMABs. However, internalization can be omitted by monovalent molecules binding CD33 such as bispecific licMABs or liCADs targeting CD33. Thus, these monovalent binders provide a highly promising approach to target CD33 positive cells, while avoiding internalization, locally interfere with an immune checkpoint and recruit effector immune cell.

Figure 15B:
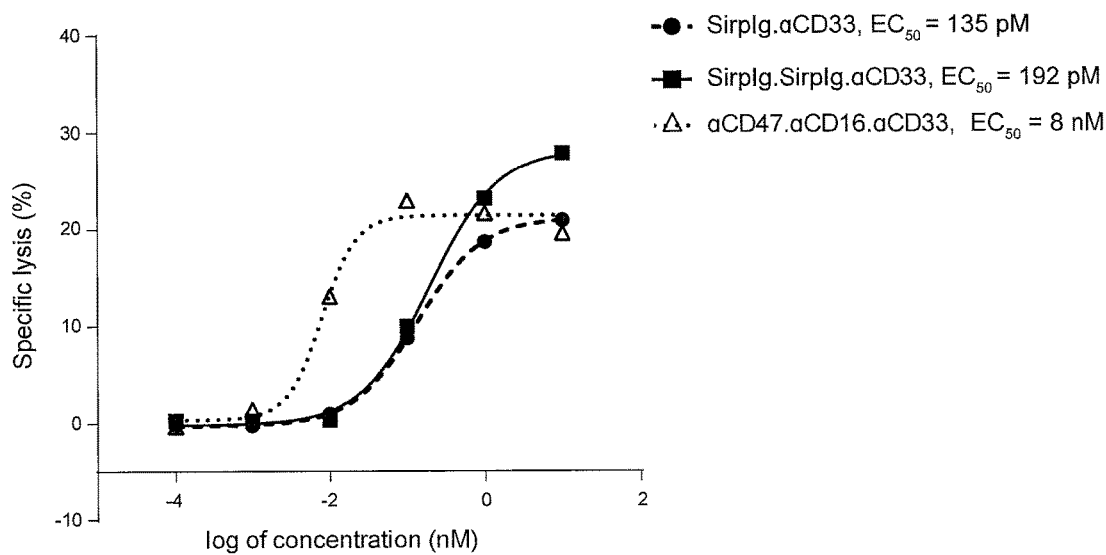

FIGS. 15A-15B show data obtained from an antibody-dependent cellular cytotoxicity (ADCC) assay testing the dose-dependent induction of specific lysis of MOLM-13 cells. MOLM-13 cells were labeled with Calcein-AM as described for FIG. 7. Calcein-AM labeled MOLM-13 cells were incubated with NK cells (effector:target ratio 2:1) for 4 h at increasing protein concentration. Cytotoxic effects induced by the molecules were analyzed and plotted as a dose-response curve.

(15A) Cytotoxic effects on MOLM-13 cells induced by SirpIg.αCD33 licMAB, SirpIg.SirpIg.αCD33 licMAB, αCD33 mAB, SirpIg.αCD19 licMAB and αCD19 mAB. αCD19 mAB and licMAB were used as a controls (upper panel). Cytotoxic effects on MOLM-13 cells induced by Fc-engineered variants of SirpIg.αCD33 licMAB, SirpIg.SirpIg.αCD33 licMAB and αCD33 mAB (lower panel).

(15B) Cytotoxic effects on MOLM-13 cells induced by liCADs and a control triplebody (αCD47.αCD16.αCD33).

FIG. 16 shows data obtained from an antibody-dependent cellular phagocytosis (ADCP) assay testing the dose-dependent induction of specific phagocytosis of MOLM-13 cells by donor-derived human macrophages.

Phagocytosis of MOLM-13 cells by donor-derived human macrophages stimulated by SirpIg.αCD33 licMAB, SirpIg.SirpIg.αCD33 licMAB and αCD33 mAB at different concentrations was evaluated by imaging flow cytometry. Percentage of macrophages that engulfed MOLM-13 cells was determined with respect to all macrophages, corrected for unspecific phagocytosis (in the absence of licMABs or mAB) and normalized to maximal phagocytosis (obtained with beads). Error bars indicate SEM of three independent experiments using three independent donors and statistical significance was calculated with a t-test with Welch's correction (*p-value <0.05, **p-value <0.01) (upper panel). Control experiments for phagocytosis are shown in the lower panel.

In conclusion, licMABs significantly increase phagocytosis in comparison to a conventional αCD33 mAB in a concentration dependent manner, most likely because of the blockade of the CD47-Sirp interaction.

Figure 17:
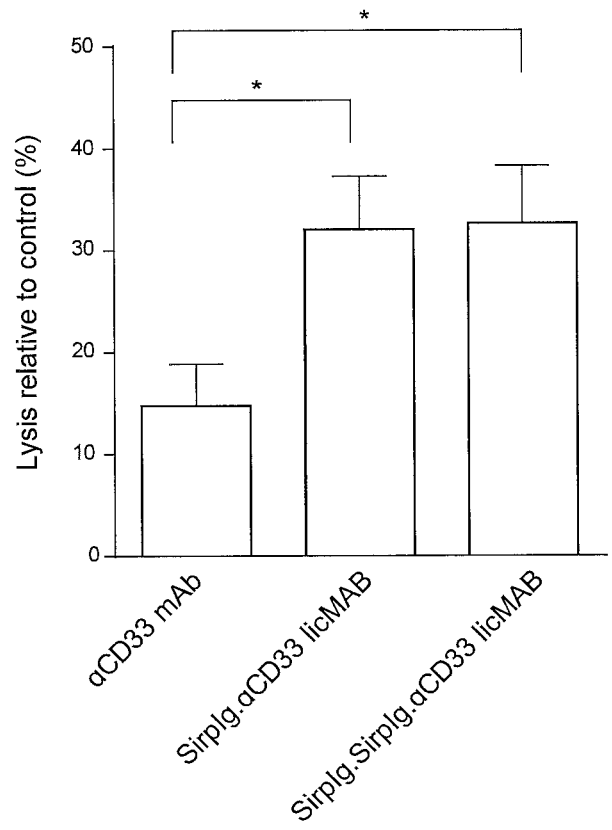

FIG. 17 shows licMAB induced NK cell-mediated cytotoxicity of AML patient samples. Cytotoxicity of primary, patient-derived AML cells triggered by αCD33 mAB, SirpIg.αCD33 licMAB and SirpIg.SirpIg.αCD33 licMAB at a concentration of 10 nM was analyzed by determining the percentage of remaining CD33 or CD123 positive cells by flow cytometry. Values were normalized to control cultures. Columns represent the mean value and SEM (error bars) of 6 different AML patient samples. Statistical differences were assessed by the Mann-Whitney U test (*p-value <0.05).

Figure 18:
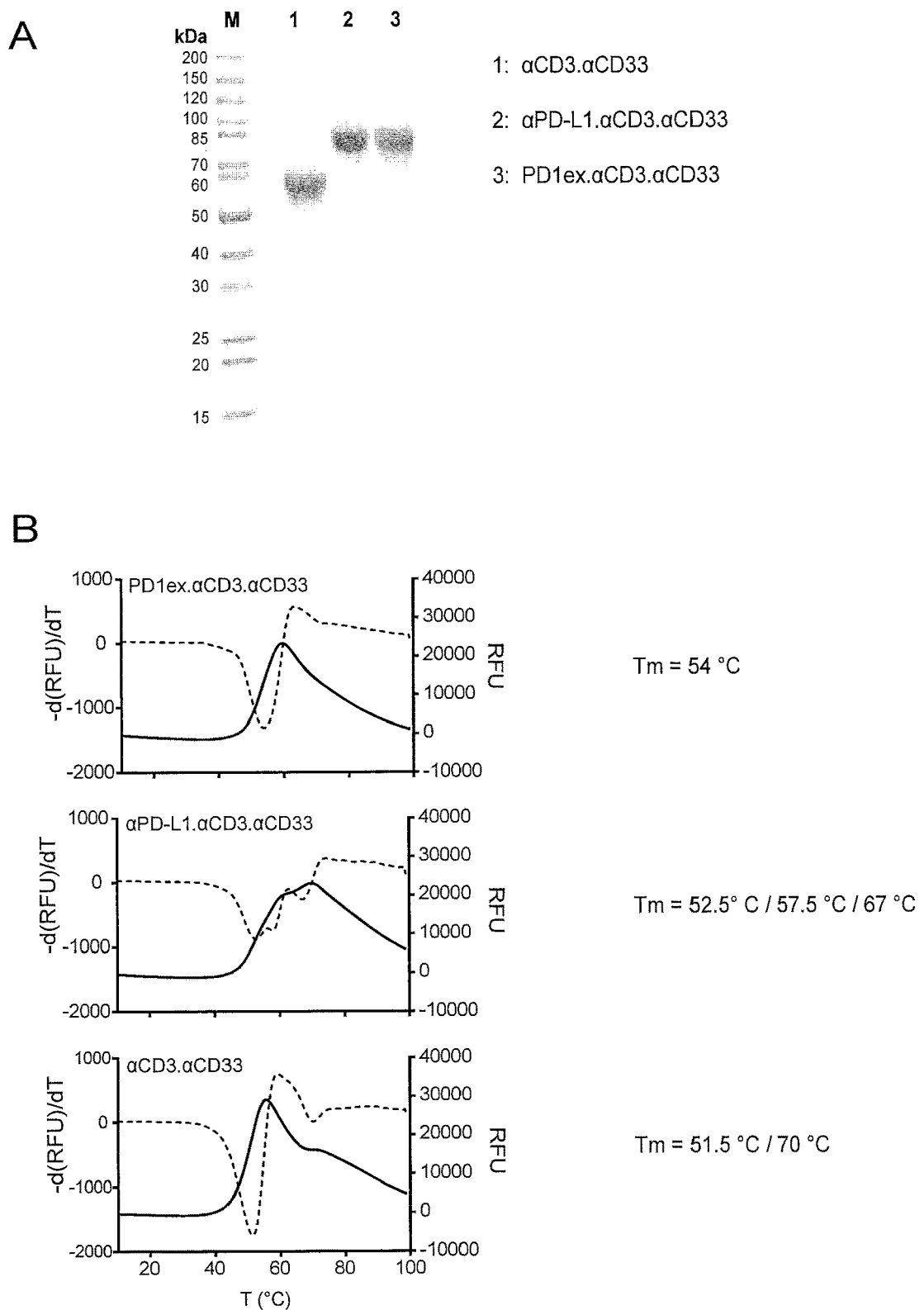

FIGS. 18A-18R show the purity and stability of the two liCAD molecules αPD-L1.αCD3.αCD33 and PD1ex.αCD3.αCD33 in comparison to the bispecific control molecule αCD3.αCD33.

(18A) SDS-PAGE analysis of the proteins described. (M) molecular weight marker.

(18B) Melting curves of the molecules with calculated melting temperatures as determined by thermofluor assay.

Conclusively, liCADs can be expressed and purified in suitable amounts and show sufficient stability in thermo stability assays.

FIGS. 19A-19C show binding of the liCAD binding modules to their targets by flow cytometry analysis as well as the determination of the dissociation constants ($K_D$).

(19A) Binding of the αPD-L1 scFv and PD1ex binding arms (in the molecules αPD-L1.αCD3.αCD33 and PD1ex.αCD3.αCD33) to PD-L1 on a stably transfected HEK293_PD-L1 cell line overexpressing PD-L1 (upper panel). $K_D$ determination studies are shown in the lower panel and $K_D$ values are indicated (n=3, error bars show SEM).

(19B) Binding of the αCD3 scFv in the molecule PD1ex.αCD3.αCD33 to Jurkat cells (upper panel) and determination of $K_D$ values as indicated (n=3, error bars show SEM) (lower panel).

(19C) Binding of the αCD33 scFv in the molecule PD1ex.αCD3.αCD33 to stably transfected HEK293_CD33 cells overexpressing CD33 and determination of $K_F$ values as indicated (n=3, error bars show SEM).

Taken together, the single modules within the liCAD framework are binding their respective antigens or receptors.

Figure 20:
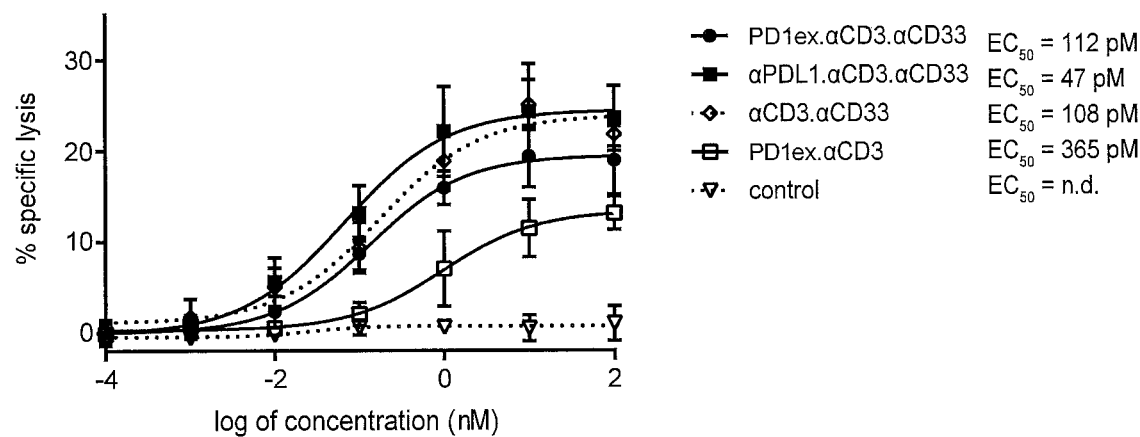

FIG. 20 shows experimental data of a redirected lysis (RDL) assay evaluating the dose-dependent specific killing behavior of pre-expanded T cells. The RDL assay was performed with MOLM-13_PD-L1 (stably expressing PD-L1) as target cells at an effector to target ratio of 5 to 1 (n=3, error bars show SEM).

In RDL assays, the recruitment of T cells to their target cells as well as the specificity of target cell killing can be analyzed in vitro using pre-activated T cells that are able to kill their target cells in a short time frame. Briefly, CD33 and PD-L1 double positive target cells are labeled with Calcein-AM and mixed with pre-activated T cells in an effector to target ratio of 5 to 1. After 4 h incubation, the release of the fluorescent dye into the supernatant was analyzed.

The results indicate that targeting of tumor cells is assured by the tumor antigen targeting domain αCD33 scFv. The extracellular domain of PD1 (PD1ex) only has minor effects on targeting the stable MOLM-13_PD-L1 cell line.

FIGS. 21A-21B display experimental data of preferential killing of stably transfected HEK_CD33_PD-L1 cells over stably transfected HEK_PD-L1 cells using pre-expanded T cells as effectors.

(21A) Dose-dependent preferential killing assay on double positive HEK_CD33_PD-L1 cells (++) versus single positive HEK_PD-L1 cells (+) at an effector to target ratio of 2 to 1 (one exemplary dataset is shown out of three).

Calcein-AM labeled HEK_PD-L1 single positive cells, mixed with unlabeled HEK_CD33_PD-L1 double positive cells, were used as targets to compare efficacy of liCADs and control molecules at a constant effector to target ratio of 2 to 1 in a dose-dependent manner. In a parallel reaction, unlabeled HEK_PD-L1 single positive cells, mixed with Calcein-AM labeled HEK_CD33_PD-L1 double positive cells, were used as targets to compare efficacy of liCADs and control molecules at a constant effector to target ratio of 2 to 1 as well in a dose-dependent manner. % specific lysis was analyzed and demonstrates the potential of liCADs to preferentially kill double positive target cells.

(21B) The assay described in (A) is displayed at maximal protein concentrations of 10 nM.

In summary, killing of tumor cells is highly dependent on the tumor targeting module within the liCAD molecules. The PD1ex domain does not contribute to tumor cell targeting.

FIGS. 22A-22B show flow cytometry data of T cell killing using unstimulated T cells as effector cells at an effector to target ratio of 2 to 1. Dose-dependent induction of target cell killing was evaluated.

(22A) Percentage of survival of CD33 and PD-L1 double positive MOLM-13_PD-L1 cells using liCAD molecules in comparison to controls (n=4). Error bars show SEM.

General efficacy of liCAD molecules was already demonstrated using pre-activated T cells (FIG. 20 and FIG. 21). To evaluate the efficacy of liCAD molecules one step further, in the T cell killing assay shown here, unstimulated T cells were used as effector cells to analyze the induction of T cell effector functions by the liCAD molecules without additional stimuli. Freshly isolated human T cells were incubated with CD33 and PD-L1 double positive stable MOLM-13_PDL1 cells at a constant effector to target ratio of 2 to 1 in a dose dependent manner. After 72 h the percentage of surviving target cells was analyzed by flow cytometry by analyzing CD33 positive living target cells.

The results clearly show that liCAD molecules are able to induce specific killing of double positive target cells in a dose-dependent manner and that PD1ex plays a minor role in targeting the stable MOLM-13_PDL1 cell line.

(22B) Percentage of survival in a direct comparison of liCAD molecules on CD33 single positive MOLM-13 cells versus CD33 and PD-L1 double positive MOLM-13_PD-L1 cells (n=4). Error bars show SEM.

The results demonstrate that liCAD molecules lead to more efficient killing of CD33 and PD-L1 double positive target cells in comparison to CD33 single positive target cells.

FIGS. 23A-23B show flow cytometry based T cell assays with CD33 single positive MOLM-13 cells versus CD33 and PD-L1 double positive MOLM-13_PDL1 cells using unstimulated T cells as effector cells at an effector to target ratio of 2 to 1.

(23A) Dose-dependent T cell proliferation assay (n=3).

One readout of T cell activation is the analysis of the T cell proliferation behavior. Freshly isolated T cells were labeled with CFSE and mixed with either CD33 single positive MOLM-13 cells or, in a parallel reaction, with CD33 and PD-L1 double positive stable MOLM-13_PDL1 cells at a constant effector to target ratio of 2 to 1 in a dose dependent manner.

With every T cell division, the CFSE cell dye is diluted, which can be monitored by flow cytometry. By this, after 96 h the percentage of proliferated living T cells was evaluated.

The data clearly indicates that, in line with the results from T cell killing assays, liCAD molecules lead to more efficient T cell proliferation when incubated with CD33 and PD-L1 double positive target cells in comparison to CD33 single positive target cells.

(23B) IFNγ release at 5 nM liCAD concentration, displayed as ratio of IFNγ release on MOLM-13 versus MOLM-13_PDL1 cells (n=4). Error bars show SEM.

The activation of T cells correlates with their secretion of cytokines like IFNγ into the supernatant. To evaluate IFNγ release, freshly isolated human T cells were incubated with either CD33 single positive MOLM-13 cells or, in a parallel reaction, with CD33 and PD-L1 double positive stable MOLM-13_PDL1 cells at a constant effector to target ratio of 2 to 1 at a constant liCAD concentration of 5 nM. After 72 h, the supernatant of the reactions was analyzed using a bead-based flow cytometry method, in which the cytokine is captured on pre-coated beads.

The results indicate that both liCAD molecules tested here lead to similar IFNγ release, independent of the presence of PD-L1 on the respective cell line, whereas the bispecific control molecule shows reduced IFNγ levels in the presence of PD-L1.

FIGS. 24A-24B display the flow cytometry analysis of T cell activation using unstimulated T cells as effector cells and double positive MOLM-13_PD-L1 cells as targets at an effector to target ratio of 2 to 1.

(24A) T cell activation without target cells at 5 nM liCAD concentration (n=3).

During the process of T cell activation, different characteristic surface molecules are upregulated. To analyze the effect of liCAD molecules on T cells without target cells, unstimulated human T cells were incubated with liCADs at a concentration of 5 nM. After 96 h, the T cells were analyzed by flow cytometry regarding their expression of the two activation markers CD25 and CD69.

Taken together, liCAD molecules alone only lead to a slight upregulation of activation markers and thereby to minor T cell activation.

(24B) T cell activation with MOLM-13_PD-L1 target cells at 5 nM liCAD concentration (n=3). Error bars show SEM.

Unstimulated human T cells were incubated with either CD33 single positive MOLM-13 cells or with CD33 and PD-L1 double positive stable MOLM-13_PDL1 cells at a constant effector to target ratio of 2 to 1 at 5 nM liCAD concentration. After 96 h the T cells were analyzed by flow cytometry regarding their expression of the two activation markers CD25 and CD69 as well as the upregulation of PD-1.

In summary, liCAD molecules are able to activate T cells in the presence of both MOLM-13 and MOLM-13_PD-L1 cells.

FIGS. 25A-25C schematically show exemplary antibody formats used in clinical therapy or studies. 25A) An IgG antibody targeting a tumor antigen that is expressed on tumor cells. Examples from clinical therapy or studies are Herceptin or Rituximab. This type of antibody has an effector (cell) function and a tumor specificity. 25B) An IgG antibody targeting an immune checkpoint such as CTLA4 or PD-1/L1. Examples from clinical therapy or studies are Ipilimumab, Tremelimumab, CT-011, BMS-936558 or MPDL3280A. This type of antibody has an effector (cell) function, no tumor specificity but inhibits an immune checkpoint by binding to the respective immune checkpoint. 25C) A tumor specific antibody and an immune checkpoint antibody can be combined as combination therapy in clinical applications.

FIGS. 26A-26D schematically show different exemplary antibody formats, fragments and derivatives thereof such as Fc-fusions. 26A) A bispecific antibody in the IgG format with tumor specificity on one binding site and effector (cell) function on the other binding side, e.g. anti-CD3. Examples are Catumaxomab and Ertumaxumab. 26B) A F(ab')2 fragment with tumor specificity. 26C) A minibody is composed of single-chain Fv (scFv) fragments that are linked via to CH2-CH3 domains (also known as Fc domain). The Fc domain heterodimerizes to fulfill an effector function. 26D) Example for a minibody composing a protein domain, e.g. the extracellular domain of SIRPalpha (or SirpIg), fused to the CH2-CH3 (Fc domain), which upon heterodimerization built the minibody.

FIGS. 27A-27B schematically show exemplary antibody derivatives in preclinical or clinical development. 27A) Bispecific T cell engager (BiTE) consists of two single-chain Fv (scFv) fragments with different specificities. One scFv has a strong effector function mediated by the anti-CD3 binding, the other scFv has a tumor specificity, e.g. CD19 or CD33). ScFvs consist of the variable domains of the heavy and light chain of an IgG antibody, connected by a linker. 27B) A triplebody format consists of three scFvs that are connected by flexible linkers. Triplebodies can have up to three different specificities (indicated by solid lines, dashed lines, no fill). For example, SPM-2 has three different specificities, one tumor specificity (anti-CD123), one effector (cell) specificity (anti-CD16) and one second tumor specificity (anti-CD33).

FIGS. 28A-28B schematically show the trispecific antibodies examples according to the present invention. 28A) Local inhibitory checkpoint antibody derivatives (liCAD) are composed of the extracellular domain of a protein interfering with an immune checkpoint, e. g. SIRPalpha or SirpIg interfering with CD47, a scFv specific for an effector (cell) function and a scFv specific for a tumor antigen. Thus, liCADs combine three functions in one molecule. 28B) A liCAD with two repeats of the extracellular domain of a protein interfering with an immune checkpoint, e.g SIRPalpha or SirpIg or PD-1, which are connected by a linker.

FIGS. 29A-29C schematically show the trispecific antibodies examples according to the present invention. 29A) Local inhibitory checkpoint monoclonal antibody (licMAB) are composted of a tumor specific antibody, preferably in the IgG1 format, which comprises a fusion of the extracellular domain of a protein interfering with an immune checkpoint, e. g. SIRPalpha or SirpIg interfering with CD47. The extracellular domain is fused by a flexible linker. 29B) The licMAB according to A) can comprise mutations in the amino acid sequence of the Fc domain to obtain a stronger effector (cell) function (licMAB Fc engineered) as indicated by the "star." 29C) A licMAB according to A) can comprise two or more repeats of the extracellular domain of a protein interfering with an immune checkpoint, e. g. SIRPalpha or SirpIg.

In the following, reference is made to the examples, which are given to illustrate, not to limit the present invention.

EXAMPLES

Example 1

In this example, methodology is described that was used by the present inventors for embodiments of the present invention. More specifically, the construction and production of exemplary molecules according to the present invention is described as well as details on cell lines, patients, the preparation of various cells, assays for thermal stability, the detection of binding by flow cytometry, the quantitative determination of cell surface antigens, assays for $K_D$ determination, internalization assays by flow cytometry and/or confocal microscopy, assays for determining antibody-dependent cellular cytotoxicity (ADCC) and antibody-dependent cellular phagocytosis (ADCP) and antibody-dependent cellular cytotoxicity in primary AML patient samples.

SIRPα-antiCD33 licMAB, 2×SIRPα-antiCD33 licMAB and antiCD33 mAb Construction and Production The antiCD33 variable light (VL) and variable heavy (VH) (clone hP67.6) were generated using custom gene synthesis (GeneArt, Thermo Fisher Scientific). The antiCD33 VL was subcloned into the pFUSE2-CLIg-hk vector (InvivoGen) and the antiCD33 VH into the pFUSE-CHIg-hG1 vector (InvivoGen). To generate the SIRPα-antiCD33 licMAB, the N-terminal Ig-like V-type domain of SIRPα (residues 1-120) was synthesized using custom gene synthesis (GeneArt, Thermo Fisher Scientific) and subcloned into the N-terminus of the antiCD33 light chain (LC) together with a $(G_4S)_4$ linker. A second SIRPα-$(G_4S)_4$ linker cassette was cloned N-terminal of the SIRPα-antiCD33 LC to obtain the 2×SIRPα-antiCD33 light chain. A cassette of SIRPα-$(G_4S)_2$ linker, containing a PreScission protease cleavage site (PreSc) at the C-terminus, was cloned N-terminal of the antiCD33 LC to generate an SIRPα-PreSc-antiCD33 antibody with a cleavable SIRPα. The corresponding plasmids were transfected into Expi293F cells (Thermo Fisher Scientific) according to the manufacturer's protocol. After five to seven days, the cell culture supernatant was harvested and licMABs were purified by protein A affinity chromatography. To obtain the antiCD33 mAb, SIRPα-PreSc-antiCD33 was incubated with PreScission protease for 4 h followed by a second round of protein A affinity chromatography. LicMABs and mAb were dialyzed against Phosphate Buffered Saline (PBS) and size exclusion chromatography (SEC) of the purified molecules was performed using a Superdex 200 increase 10/300 column (GE Healthcare Life Sciences, Little Chalfont, Buckinghamshire, United Kingdom). LicMABs and mAb were then analyzed by 4-20% SDS-PAGE (Expedeon) under reducing conditions and visualized by Coomassie Brilliant Blue staining. Protein concentration was measured with a spectrophotometer (NanoDrop, GE Healthcare Life Sciences, Little Chalfont, Buckinghamshire, United Kingdom) and aliquots were stored at −80° C.

Cell Lines

The MOLM-13 cell line was purchased from the 'Deutsche Sammlung von Mikroorganismen und Zellkulturen' (DSMZ, Leibniz-Institut DSMZ, Braunschweig, Germany) and the Flp-IN™-CHO and Flp-IN™ T-Rex™-293 cell lines from Thermo Fisher Scientific (Waltham, Mass., USA). The THP-1 and the Jurkat cell line was kindly provided by collaborators and cultured in RPMI 1640+GlutaMAX (Gibco, Thermo Fisher Scientific) and supplemented with 10% fetal bovine serum (FBS, Gibco, Thermo Fisher Scientific). MOLM-13 cells were cultured in RPMI 1640+ GlutaMAX (Gibco, Thermo Fisher Scientific) and supplemented with 20% FBS. Flp-IN™-CHO was maintained in Ham's F-12 (Biochrom) media supplemented with 10% FBS and Flp-IN™ T-Rex™-293 cell line was cultured in DMEM+GlutaMAX and supplemented with 10% FBS and 2 mM L-glutamine. The Flp-IN™-CHO or Flp-IN™ T-Rex™-293 cell lines were engineered to stably express either human CD33 (referred to as CHO_CD33 or CHO-.exCD33, HEK.exCD33 or HEK293_CD33), human CD16 (referred to as CHO.exCD16), human CD47 (referred to as CHO_CD47 or CHO.exCD47) or human PD-L1 (referred to as HEK293_PD-L1) and maintained in selection media according to manufacturers' instruction. The HEK293_CD33 cell line has further been engineered to additionally stably express human PD-L1 (HEK_CD33_PD-L1 cell line). The MOLM-13 cell line was engineered to stably expressed human PD-L1 and is referred to MOLM-13_PD-L1 cell line. The Expi293F™ and Freestyle™ 293-F cell line was obtained from Thermo Fisher Scientific and cultured in Expi293™ Expression Medium or FreeStrylc™ 293 Expression Medium, respectively.

Patients

After written informed consent in accordance with the Declaration of Helsinki and approval by the Institutional Review Board of the Ludwig-Maximilians-Universität (Munich, Germany), peripheral blood (PB) or bone marrow (BM) samples were collected from healthy donors (HDs) and patients with AML at initial diagnosis or relapse. PB or BM samples from AML patients were cryoconserved at ≤−80° C. in 80% FCS and 20% dimethyl sulfoxide (Serva Electrophoresis) until usage. PB from IIDs was obtained on the day of the experiment.

Preparation of Peripheral Blood Mononuclear Cells (PBMCs), NK Cells and Monocytes from Whole Human Blood PBMCs from AML patients and HDs were separated from PB by density gradient using the Biocoll separating solution (Biochrom), according to the manufacturer's protocol. NK cells were either expanded ex vivo by culturing PBMCs under IL-2 stimulus as described previously (Carlens et al., 2001; Hum. Immunol.; 62(10); 1092-1098) or freshly isolated by magnetic separation using a human NK cell isolation kit (MACS Miltenyi Biotech) according to the manufacturer's protocol. Monocytes were isolated from PBMCs with human CD14 MicroBeads (MACS Miltenyi Biotech) by magnetic separation following the manufacturer's instructions.

Thermal Stability

The thermal stability of the licMABs and mAb was determined by fluorescence thermal shift assays using the CFX96 Touch Real-Time PCR Detection System (Bio-Rad, Munich, Germany) (Boivin et al., 2013; Protein Expr. Purif.; 91(2); 192-206). 10 µg of protein containing 1×SYPRO Orange (Thermo Fisher Scientific) were measured using FAM and SYBR Green I filter pairs.

Detection of Binding by Flow Cytometry

If not otherwise stated, flow cytometry analyses were performed on a Guava easyCyte 6HT instrument (Merck Millipore, Billerica, Mass., USA) and data was plotted with GuavaSoft software version 3.1.1 (Merck Millipore, Billerica, Mass., USA).

MOLM-13, SEM, CHO_CD33 and CHO_CD47 cells were stained with 15 µg/ml of licMABs or mAb followed by staining with a secondary FITC antiHuman IgG Fc antibody (clone HP6017, BioLegend). The median fluorescence intensity (MFI) ratio was calculated dividing MFI of the antibody by the MFI of the isotype control.

$K_D$ Determination

CD33 equilibrium binding constants ($K_L$, as an avidity measurement) of the licMABs and mAb were determined by calibrated flow cytometry analyses as previously described (Benedict et al., 1997; J. Immunol. Methods; 201(2); 223-231). Briefly, MOLM-13 cells were incubated with licMABs or mAb in concentrations ranging from 0.01 to 15 µg/ml and stained with a FITC antiHuman IgG Fc (clone HP6017, BioLegend) secondary antibody by flow cytometry. The instrument was calibrated with 3.0-3.4 µm Rainbow Calibration particles of 8 peaks (BioLegend), the maximum MFI value was set to 100% and all data points were normalized accordingly. The assay was performed in quadruplicates and the values were analyzed by non-linear regression using a one-site specific binding model.

Internalization Assay by Flow Cytometry

MOLM-13 cells were incubated with 15 µg/ml of licMABs or mAb either on ice-cold water for 2 h (to prevent internalization) or at 37° C. for 30, 60 or 120 min. Cells were then washed with ice-cold FACS buffer and antibodies remaining on the surface were detected by staining with FITC antiHuman IgG Fc (clone HP6017, BioLegend). To define the background fluorescence, MOLM-13 cells were directly stained with the secondary antibody. The internalization was calculated as follows:

Internalization (%) =

$$\frac{(MFI_{4°\,C.} - MFI_{background}) - (MFI_{37°\,C.} - MFI_{background})}{(MFI_{4°\,C.} - MFI_{background})} \times 100$$

Internalization Assay by Confocal Microscopy

MOLM-13 cells were grown on a poly-L-lysine (Sigma-Aldrich) coated 96-well plate. Subsequently, cells were incubated with 15 µg/ml of licMABs or mAb directly labeled with Alexa Fluor 488 (Antibody Labeling Kit, Thermo Fisher Scientific), either on ice-cold water for 2 h or at 37° C. for 30, 60 or 120 min. Then, cells were fixed and permeabilized in 20 mM PIPES pH 6.8, 4% formaldehyde, 0.2% Triton X-100, 10 mM EGTA, 1 mM $MgCl_2$ at room temperature for 10 min, followed by incubation in blocking solution (3% bovine serum albumin in PBS). Cells were washed three times with 0.05% Tween 20 in PBS and stored in PBS until examination on a fully automated Zeiss inverted microscope (AxioObserver Z1) equipped with a MS-2000 stage (Applied Scientific Instrumentation, Eugene, Orlando, USA), a CSU-X1 spinning disk confocal head (Yokogawa) and a LaserStack Launch with selectable laser lines (Intelligent Imaging Innovations, Denver, Colo.). Images were acquired using a CoolSnap HQ camera (Roper Scientific, Planegg, Germany), a 63× oil objective (Plan Neofluoar 63×/1.25) and the Slidebook software (version 6.0; Intelligent Imaging Innovations, Denver, Colo.). Images were processed with Adobe Photoshop CS4 (Adobe Systems, Mountain View, Calif., USA).

Antibody-Dependent Cellular Cytotoxicity (ADCC)

Target cells (MOLM-13 or SEM) were labeled with calcein AM (Thermo Fisher Scientific) according to manufacturer's protocol. Calcein-labeled target cells were incubated with freshly isolated or IL-2 expanded NK cells in an effector-to-target (E:T) ratio of 2:1 and licMABs or mAb at different concentrations for 4 h. Target cells were cultured in 10% Triton X-100 to assess the maximum unspecific lysis. Calcein release was measured by fluorescence intensity with an Infinite® M100 plate reader instrument (TECAN, Männedorf, Switzerland) and specific lysis was calculated as follows:

Specific lysis (%) =

$$\frac{Fluorescence_{Sample} - Fluorescence_{Spontaneous\ lysis}}{Fluorescence_{Maximum\ lysis} - Fluorescence_{Background}} \times 100$$

Averaged specific lysis of triplicates or quadruplicates were plotted according to a dose-response curve and analyzed using the integrated four parameter non-linear fit model.

Antibody-Dependent Cellular Phagocytosis (ADCP)

Phagocytosis assay was performed as described previously (Blume et al., 2009; J. Immunol.; 183(12); 8138-8147). Briefly, isolated monocytes were stained with PKH67 (Sigma-Aldrich) according to the manufacturer's instructions and differentiated to macrophages by 20 ng/ml Macrophage-Colony Stimulator Factor (M-CSF) (R&D Systems) in X-VIVO 10 medium (Lonza) supplemented with 10% autologous serum. MOLM-13 cells were stained with PKH26 (Sigma-Aldrich) following the manufacturer's instructions and incubated in a 1:2 E:T ratio with licMABs or mAb concentrations ranging from 0.01 nM to 100 nM for 2 h. Polybead® Carboxylate Red Dye Microspheres 6 µm (Polysciences) were used as a positive control and incubation either at 4° C. or at 37° C. in the presence of 10 µM Cytochlasin D (Sigma-Aldrich) served as a negative control. Cells were harvested, measured by imaging flow cytometry using an ImageStream®$^X$ Mark II instrument (Merck Millipore, Billerica, Mass., USA) and analyzed with IDEAS® and INSPIRE® Software (Merck Millipore, Billerica, Mass., USA). The maximum phagocytosis value was set to 100% and all data points were normalized accordingly. Mean values and standard errors of triplicates were calculated and plotted.

Antibody-Dependent Cellular Cytotoxicity in Primary AML Patient Samples

Ex vivo expanded primary AML cells were co-cultured with freshly isolated healthy donor NK cells, at an E:T ratio of 5:1 in an ex vivo long term culture system as described by Krupka and coworkers (Krupka et al., 2016; Leukemia; 30(2); 484-491) (Krupka et al., 2014; Blood; 123(3); 356-365). Antibodies were added at a final concentration of 10 nM. After 24 hours, cells were harvested, stained for CD16 (clone B73.1), CD56 (clone HCD 56), CD33 (clone WM53) and in some cases CD123 (clone 6H6; all antibodies from Biolegend) and analyzed by flow cytometry with a BD LSR 11 (Becton Dickinson, Heidelberg, Germany). The percentage of residual CD33 or CD123 positive cells in treated cultures relative to control cultures was used to determine licMAB-mediated cellular cytotoxicity.

Plotting and Statistical Analysis

Unless stated otherwise, data were analyzed and plotted with GraphPad Prism version 6.00 for Windows (GraphPad Software, La Jolla, Calif., USA).

Differences in phagocytosis were calculated using an unpaired, parametric Student's t-test with Welch correction and statistical differences of patient characterization and responses were assessed by the Mann-Whitney U test. Statistical significance was considered for p-value <0.05 (*), <0.01 (), <0.001 (*) and <0.0001 (****).

Example 2

In this example, a molecule comprising a binding site with specificity for CD33 (to bind to CD33-positive leukemic cells), a binding site with specificity for CD16 (for recruitment of immune cells as effector cells), and a binding site with specificity for the checkpoint molecule CD47 (for inhibition of antiphagocytic checkpoint signaling) and several related constructs were generated and tested. Since these molecules included antibody-derived binding domains, they are referred to as a "local inhibitory checkpoint antibody derivatives" (liCADs).

Design, Expression and Purification of liCADs

To target CD47, the extracellular N-terminal Ig variable domain of SIRPα (herein called SIRP-Ig or SirpIg) was used, which has been shown to be sufficient for CD47 binding (Barclay et al., 2009). In order to modulate binding affinities, molecules carrying two copies of SIRP-Ig were designed. Apart from the varying N-terminal module 1 all constructs had a central anti-CD16 scFv (derived from murine hybridoma 3G8) (Fleit et al., 1982), recruiting immune effector cells (module 2). CD16, also known as Fc gamma receptor IIIa (FcγRIIIa) is expressed on NK cells, dendritic cells (DCs) and macrophages and mediates antibody dependent cellular cytotoxicity (ADCC) or antibody dependent phagocytosis (ADCP), respectively (Guilliams et al., 2014). Using a scFv specific for CD16 allows to exclude side effects generated by the Fc part of a conventional mAb that would activate far more Fc receptor expressing immune cells, thus leading to fatal side effects like the cytokine release syndrome (Brennan et al., 2010). On the C-terminus of the molecule an anti-CD33 scFv (derived from gemtuzumab ozogamicin) is expressed (module 3). CD33 is a tumor specific marker that is highly overexpressed in acute myeloid leukemia (AML) and has successfully been used as tumor target before (Larson et al., 2005; Krupka et al., 2014). As control molecules, an anti-CD47 scFv (triplebody control) was included, as well as a high affinity version of SIRP-Ig (SirpIg_CV1) that had been published before (FIG. 4 A). SirpIg_CV1 binds to CD47 with much higher affinity (1 μM) compared to SIRP-Ig (1 μM) (Weiskopf et al., 2013).

The protein domains used had the following sequences:
Amino Acid Sequence of Sirp-Ig (SEQ ID NO: 1):

EEELQVIQPDKSVLVAAGETATLRCTATSLIPVGPIQWFRGAGPGRELIY

NQKEGHFPRVTTVSDLTKRNNMDFSIRIGNITPADAGTYYCVKFRKGSPD

DVEFKSGAGTELSVRAKPS

Amino Acid Sequence of Vh CD16scFv (3G8 Clone) (SEQ ID NO: 2):

QVTLKESGPGILQPSQTLSLTCSFSGFSLRTSGMGVGWIRQPSGKGLEWL

AHIWWDDDKRYNPALKSRLTISKDTSSNQVFLKIASVDTADTATYYCAQI

NPAWFAYWGQGTLVTVSA

Amino Acid Sequence of Vl CD16scFv (3G8 Clone) (SEQ ID NO: 3):

DTVLTQSPASLAVSLGQRATISCKASQSVDFDGDSFMNWYQQKPGQPPKL

LIYTTSNLESGIPARFSASGSGTDFTLNIHPVEEEDTATYYCQQSNEDPY

TFGGGTKLEIK

Amino Acid Sequence of Vl CD33scFv (SEQ ID NO: 4):

DIQLTQSPSTLSASVGDRVTITCRASESLDNYGIRFLTWFQQKPGKAPKL

LMYAASNQGSGVPSRFSGSGSGTEFTLTISSLQPDDFATYYCQQTKEVPW

SFGQGTKVEVK

Extracted CDRS for light chain are:
CDRL1: RASESLDNYGIRFLT (SEQ ID NO: 29)
CDRL2: AASNQGS (SEQ ID NO: 30)
CDRL3: QQTKEVPWS (SEQ ID NO: 31)
Amino Acid Sequence of Vh CD33scFv (SEQ ID NO: 5):

EVQLVQSGAEVKKPGSSVKVSCKASGYTITDSNIHWVRQAPGQSLEWIGY

IYPYNGGTDYNQKFKNRATLTVDNPTNTAYMELSSLRSEDTAFYYCVNGN

PWLAYWGQGTLVTVSS

Extracted CDRS for heavy chain are:
CDRH1: DSNIH (SEQ ID NO: 32)
CDRH2: YIYPYNGGTDYNQKFKN (SEQ ID NO: 33)
CDRH3: GNPWLAY (SEQ ID NO: 34)
Between the checkpoint binding module (third binding site, e.g. Sirp-Ig, PD1ex, CTLA4ex, αPDL1), Vh und Vl domains and between the scFvs, GGGS-based linkers were included.

Linker Sequences:

(SEQ ID NO: 6)
Gly Gly Gly Ser and tandem-repeats thereof, n=2-8, (SEQ ID NO: 7-13)

(SEQ ID NO: 14)
Gly Gly Gly Gly Ser and tandem-repeats thereof, n=2-8, (SEQ ID NO: 15-21)
Sequence Constant Region IgG1 Format (CH1, Hinge, CH2, CH3): (SEQ ID NO: 22)

```
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

Sequence Constant Region of the Light Chain (CL): (SEQ ID NO: 23)

```
VAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSF

NRGEC
```

Sequence Constant Region IgG1 Format; Fc-Engineered (SEQ ID NO: 24)

Examplarily used mutations: S239D and I332E (shown below in bold) EU numbering according to Kabat, E. A., Wu, T. T., Perry, H. M., Gottesman, K. S. & Foeller, C. (1991) Sequences of Proteins of Immunological Interest (U.S.Dept.ofHealthandHum. Serv., Bethesda)

The used mutations in this example were S239D and I332E, but others may also be used.

```
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPDVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPEEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

Fc-engineered mutations may be produced and used for example in accordance with: Engineered antibody Fc variants with enhanced effector function Greg A. Lazar, Wei Dang, Sher Karki, Omid Vafa, Judy S. Peng, Linus Hyun, Cheryl Chan, Helen S. Chung, Araz Eivazi, Sean C. Yoder, Jost Vielmetter, David F. Carmichael, Robert J. Hayes, and Bassil I. Dahiyat Sequence Used for PD1ex (Extracellular Domain of PD1) (SEQ ID NO: 25)

```
NPPTFSPALLVVTEGDNATFTCSFSNTSESFVLNWYRMSPSNQTDKLAAF

PEDRSQPGQDCRFRVTQLPNGRDFHMSVVRARRNDSGTYLCGAISLAPKA

QIKESLRAELRVTERRA
```

Sequence Used for αPDL1 (Anti-PDL1; SEQ ID NO: 26 & 27)

Vl PDL1 scFv
(SEQ ID NO: 26)
```
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR
```

Vh PDL1 scFv
(SEQ ID NO: 27)
```
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSA
```

SEQ ID NO: 28 is the combination of SEQ ID NO: 26 and 27 with a (GGGGS)$_4$-linker in between.

SEQ ID NO: 22 is the sequence for the constant regions of the IgG1 format and includes the domains CH1, hinge, CH2 and CH3; this is the wildtype sequence. In contrast thereto, SEQ ID NO: 24 shows the same sequence for the constant regions of the IgG1 format but with mutations S239D and I332E; this is the mutated sequence for producing an Fc-engineered fragment. This is also the sequence which was used in embodiments of the present disclosure; the mutations are located in the CH2 domain. The Fc-fragment and the Fc-engineered fragment consist of domains CH2 and CH3 only. In all of these constant regions of the IgG1 format, the numbering according to Kabat is used. In SEQ ID NO: 24 the entire constant region including domains CH1, hinge, CH2 and CH3 is shown; however, it is clear to a person skilled in the art that the corresponding Fc-engineered fragment only contains the respective CH2 and CH3 domains.

For the various molecules according to the present invention a number of linkers were used, shown herein as SEQ ID NO: 6-SEQ ID NO: 21. SEQ ID NO: 6 is a GGGS-linker and SEQ ID NO: 7-13 are tandem repeats thereof, wherein the linker occurs 2-8 times, SEQ ID NO: 14 is a GGGGS-linker and SEQ ID NO: 15-21, again, are tandem repeats thereof, wherein the linker occurs 2-8 times. These linkers allow for an occurrence of respective domains/binding sites (first binding site, second binding site and third binding site) within molecules (liCADs and licMABs) of the present invention.

PDL1 as used herein refers to the programmed death-ligand 1 which binds to its corresponding receptor PD1. "PD1ex" is the extracellular domain of PD1.

The liCADs were expressed in *Drosophila melanogaster* Schneider 2 (S2) cells and purified from the insect cell medium after secretion. The purification strategy included a capture step (Ni-NTA affinity chromatography) via the N-terminal hexa-histidine (6×HIS) tag, followed by anion exchange (IEC) and size exclusion chromatography (SEC), resulting in monomeric soluble protein (FIG. 4B).

For binding tests using flow cytometry, cells expressing CD47, CD33 or CD16, respectively, were incubated with the purified liCADs for 30 minutes on ice. Unbound protein was washed away and bound protein was detected using an Alexa488-conjugated antibody specific for the 6×HIS tag. Cells were again incubated for 30 minutes on ice, washed twice and subsequently analysed in a Guava easyCyte 6HT (Merck Millipore).

Figure 5:
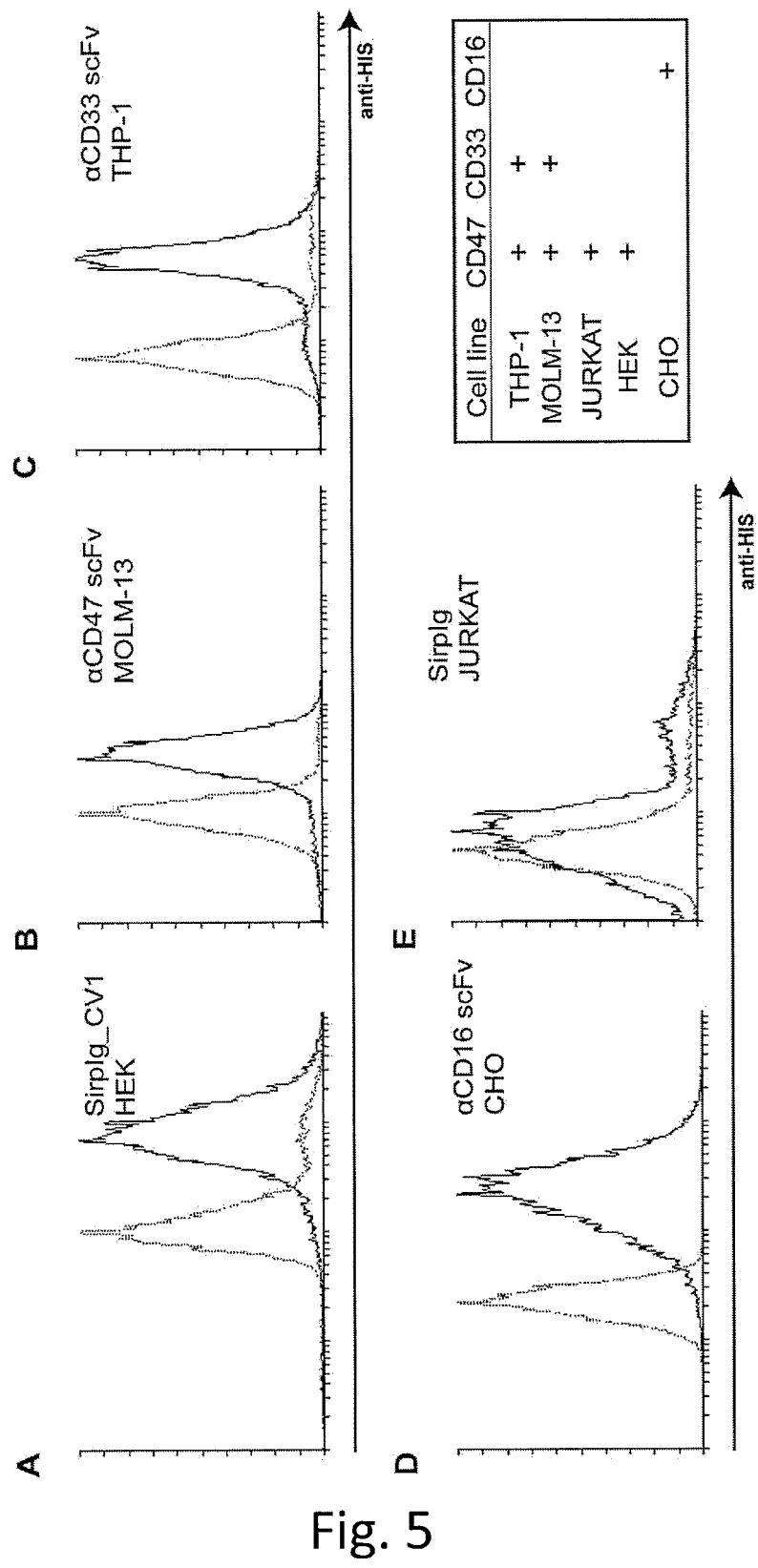

These experiments confirmed binding of SirpIg, anti-CD16 scFv and anti-CD33 scFv to their respective binding partners/antigens (i.e. binding of Sirp-Ig to CD47, binding of anti-CD16 scFv to CD16 and binding of anti-CD33 scFv to CD33) (see FIGS. 5 and 6).

liCAD-Induced Redirected Lysis of Tumor Cells

In this experiment, it was tested whether the prepared liCAD molecules would indeed induce tumor cell killing by the recruitment of NK cells in vitro. To this end, a redirected lysis (RDL) assay was carried out with the MOLM 13 cell line, which expresses CD33 and CD47 at high level. The RDL assay functions analogous to an antibody dependent cellular cytotoxicity (ADCC) assay, but recruitment and activation of NK cells is not mediated by the Fc domain of an antibody, but by the scFv against CD16. As effector cells, isolated peripheral blood mononuclear cells (PBMCs) that had been expanded as described previously (Alici et al., 2008) were used. Effector cells and calcein labeled target cells were mixed in a ratio of 2:1 and incubated with increasing protein concentrations for 4 hours at 37° C./5% $CO_2$. Afterwards fluorescence intensity of calcein was measured from the cell supernatant using the Infinite M1000 PRO (Tecan) plate reader.

The results are shown in FIG. 7. As expected, molecules targeting CD47 and CD33 simultaneously show improved cell lysis (FIG. 7A) compared to monospecific molecules only targeting CD33. Further, we determined the $EC_{50}$ values (concentrations of half maximum lysis) by dose response curves. $EC_{50}$ values achieved for the liCADs were 1.5 µM and 22 µM for the double SIRP-Ig and single SIRP-Ig, respectively. Thus, it is possible to regulate the degree of checkpoint inhibition. This is advantageous for systemic administration in vivo. In comparison to the control molecules (triplebody) the liCADs achieved a similar range of specific lysis.

As CD47 is a marker of self and thus expressed on every cell, it is necessary to avoid killing all CD47 positive cells. To this end, a preferential RDL assays was carried out to show that liCADs preferentially eliminate CD47/CD33 double positive cells over CD47 single positive cells (FIGS. 7B and 7C).

The preferential lysis assay was carried out using CD47+ single positive HEK cells mixed with CD47+, CD33+ double positive HEK cells. Effector cells and calcein stained target cells (one reaction with single positive stained and one reaction with double positive stained) were mixed in a 2:1 ratio again and incubated with the maximal used protein concentration in the redirected lysis assay or with the evaluated EC50 value for 4 hours at 37° C./5% $CO_2$. Afterwards fluorescence intensity of calcein was measured from the cell supernatant using the Infinite M1000 PRO (Tecan) plate reader.

As shown in FIGS. 7B and 7C, CD47+CD33+ HEK cells are preferentially killed in case of the Sirp-Ig-CD16-CD33 and Sirp-Ig-Sirp-Ig-CD16-CD33 liCAD, but not in case of a control triplebody that targets CD47 with high affinity. Moreover, our low affinity molecules are comparable to a bispecific control that does not target CD47 and at the EC50 value these molecules do not redirect killing of CD47+ cells at all in contrast to the triplebody control.

Phagocytosis Assay

Besides expression on NK cells, CD16 is also expressed on macrophages. Therefore, it was investigated if the liCADs can recruit macrophages as effector cells. To support the results seen in the RDL assays, it was analyzed if the prepared liCADs affect phagocytosis.

Regarding the tri-specific molecules (SIRP-Ig-αCD16-αCD33 and SIRP-Ig-SIRP-Ig-αCD16-αCD33) it was hypothesized that macrophages may be activated through CD16 signaling. Hence, an increase in phagocytosis should mainly be dependent on the SIRPα-CD47 interaction. Consequently, the liCADs combine tumor cell targeting via CD33 together with a local immune checkpoint inhibition through their low binding affinity for CD47.

A phagocytosis assay was performed generating M2 macrophages for 5 days in culture and incubation of macrophages with MOLM13 target cells in a 1:2 ratio. Cells were mixed and incubated with increasing amount of LiCAD concentration in serum free conditions for 2 hours at 37° C./5% $CO_2$. Afterwards cells were collected and FACS analyzed for macrophages that had taken up target cells.

As shown in FIG. 8 the Sirp-Ig-Sirp-Ig-CD16-CD33 liCAD is better in mediating phagocytosis compared to the Sirp-Ig-CD16-CD33 molecule, which suggests indeed an additive effect of the blocking by Sirp-Ig. Overall both liCAD molecules perform considerably better than a conventional used mAB against CD47. As a control, Sirp-Ig only was used to test if blocking of the immune checkpoint alone is enough to induce phagocytosis, which is not the case.

Tables

TABLE 1

Exemplary antibody formats used in clinical therapy or studies, respectively

| Format | Effector function | Tumor specific | Checkpoint inhibition | Example |
|---|---|---|---|---|
| IgG targeting tumor antigen | + | + | − | Herceptin (α-Her2) Rituximab (α-CD20) |
| IgG targeting immune checkpoint | + | − | + | Ipilimumab, Tremelimumab (α-CTLA4) CT-011 (α-PD1) BMS-936558, MPDL3280A (α-PDL1) |
| IgG | + | + | + | Ipilimumab + Bevaeizumab (α-CTLA4 + α-VEGF) Galiximab + Rituximab (α-PDL1 + α-CD20) CT-011 + Rituximab (α-PD1 + α-CD20) |
| bisepcific IgG | + | + | − | Catumaxotnab (α-CD3 × α-EpCAM) Ertumaxumab (α-CD3 × α-Her2) |
| F(ab')2 | − | + | − | MDX-2120, MDX-H210 (α-CD64 × α-HER2) MDX-447 (α-CD64 × α-EGFR) |
| Minibody | + | − | + | Sirpα - Fc fusions |
| BiTE | ++ | + | − | Blinaturnomab α-CD3 × α-CD19 AMG330 α-CD3 × α-CD33 |
| Triplebody | ++ | ++ | − | SPM-2 (α-CD123 × α-CD16 α-CD33) |

Figure 25:
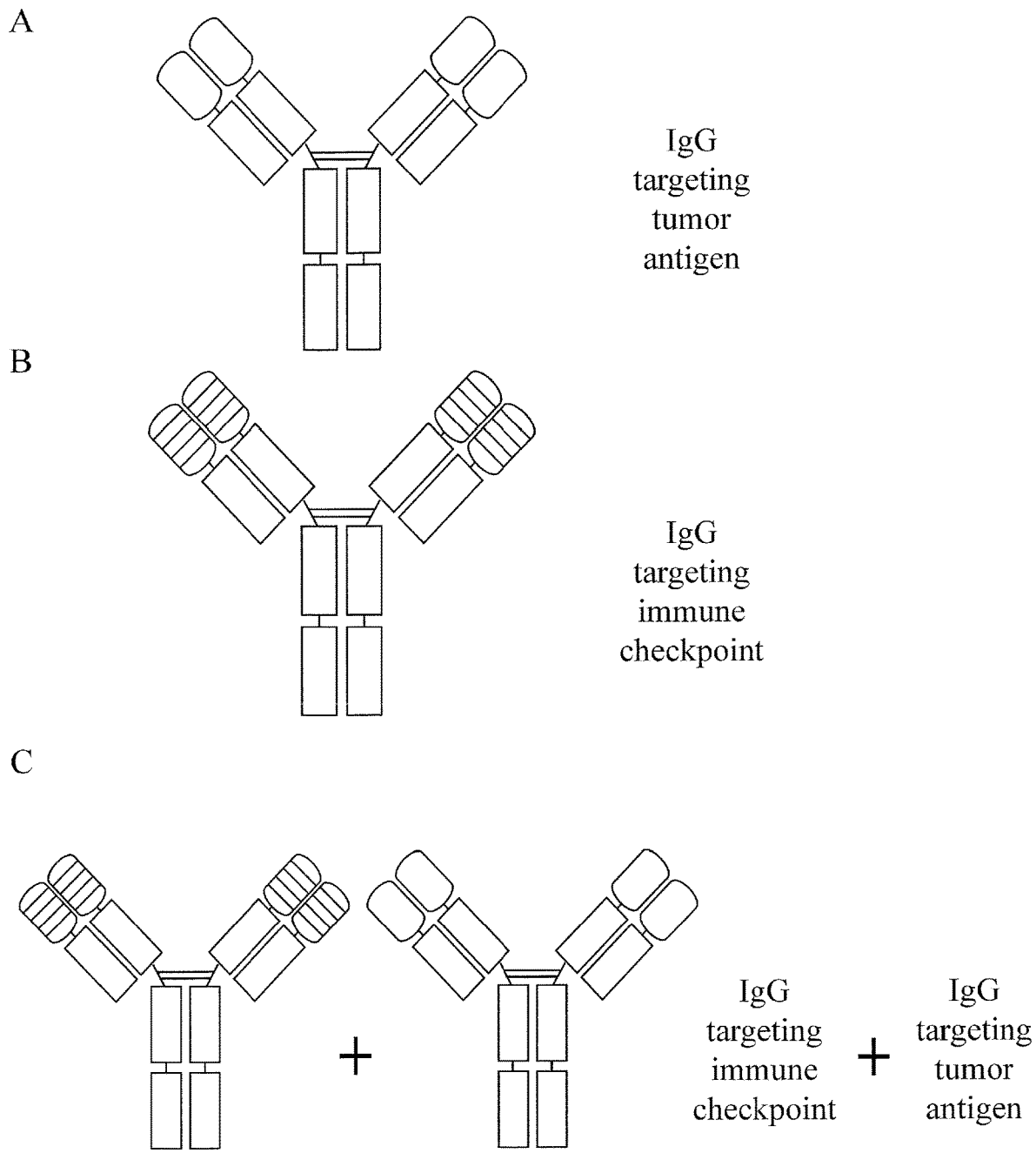
Figure 26:
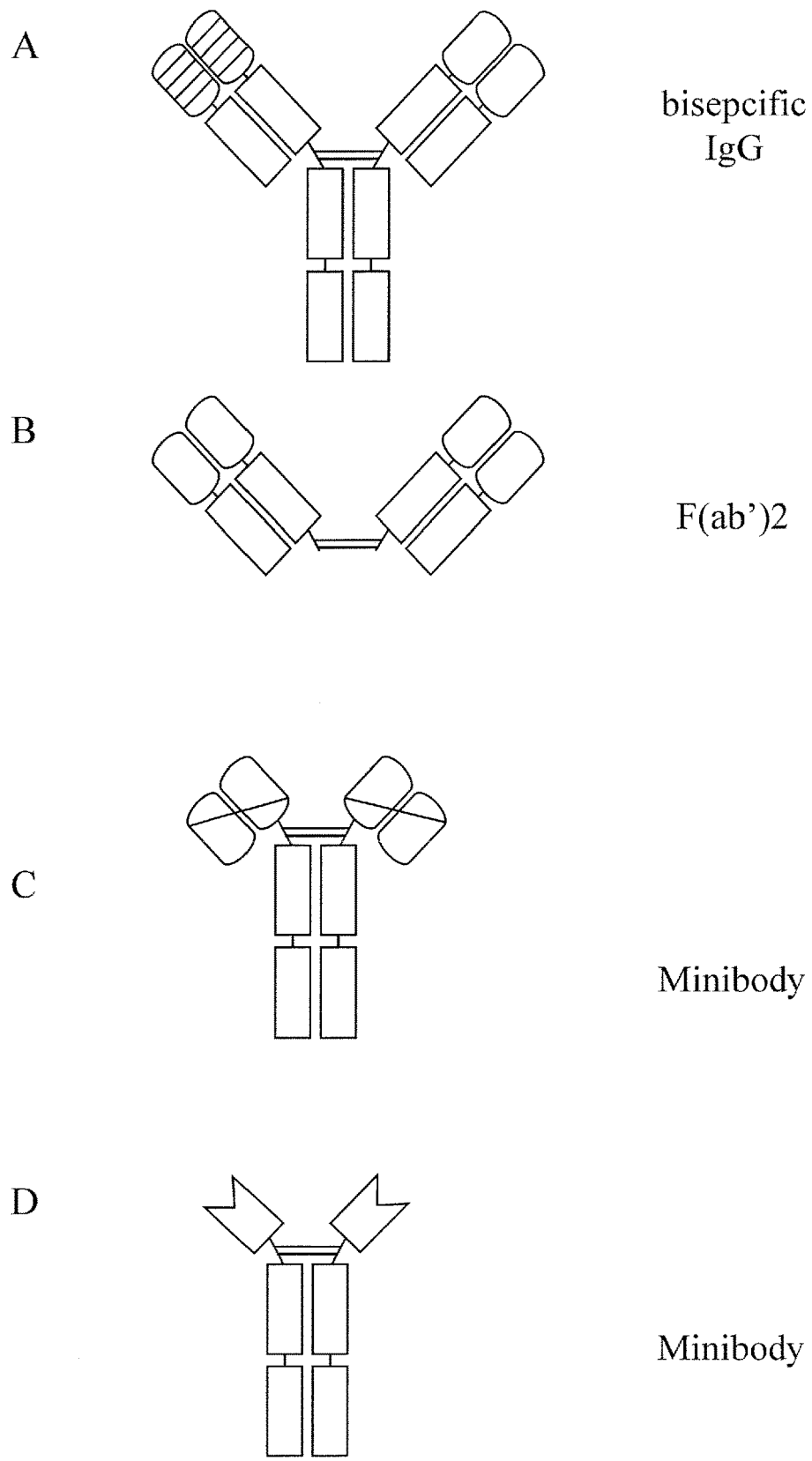

In FIGS. 25-27, antibody constant domains are shown as white rectangles. Variable heavy and light chains are shown in white (tumor antigen specific), dotted (effector cell specific) and dashed line rounded rectangles (immune checkpoint specific). White spikes represent endogenous extracellular domains of immune checkpoint receptors. BiTE, bispecific T cell engager; F(ab')2, Fragment antigen binding; IgG, immunoglobulin G. Single chain fragment variables (scFv) are depicted as two rounded rectangles with a diagonal black line across (e.g. the triplebody at the bottom of the table includes three scFv).

TABLE 2

Examples of tumor specific makers, related disease and available immunotherapy format

| Antigen | Disease |
|---|---|
| CD19 | NHL, B-ALL |
| CD20 | B cell lymphoma |
| Her2/neu | Breast cancer |
| CD123 | AML |
| CEA | Gastrointestinal cancer, lung cancer |
| EPCAM | Ovarian cancer, colorectal cancer |

TABLE 3

Cell surface molecules on different immune effector cells

| Immune cells | Surface receptors |
|---|---|
| T cells | CD3, TCRαβ, |
| Nk cells | CD16, NKG2D, NKp30, NKp40, LFA1 |
| Macrophages | CD89, CD64, CD32a, CD15a, CD16 |
| Monocytes | CD89, CD64, CD32a, CD15a, CD16 |
| Neutrophilic Granulocytes | CD89, CD64, CD32a, CD16 |

TABLE 4

Examples for molecules according to the invention

| Format | Effector function | Tumor specificity | Checkpoint function | Effector recruitment |
|---|---|---|---|---|
| liCAD | ++ | ++ | + | + |
| liCAD | ++ | ++ | ++ | + |
| licMAB | + | ++ | ++ | + |
| licMAB |  | ++ | ++ | + |

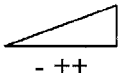

− ++

| | | | | |
|---|---|---|---|---|
| Fc engineered licMAB | + | ++ | +++ | + |

In FIGS. 28-29, variable heavy and light chains are shown in white (tumor antigen specific) and black (effector cell specific). White spikes represent endogenous extracellular domains of immune checkpoint receptors (FIGS. 28A-28B and 29A-29C).

The first molecule comprises a SIRPα-Ig linked to a tumor cell-specific and an immune cell-specific scFv. The second molecule comprises two SIRPα-Igs linked to a tumor cell-specific and an immune cell-specific scFv. The third molecule consists of an IgG antibody with variable domains having binding specificity for the tumor cell and further linked to two SIRPα-Igs.

REFERENCES

Aigner, M. et al. T lymphocytes can be effectively recruited for ex vivo and in vivo lysis of AML blasts by a novel CD33/CD3-bispecific BiTE antibody construct. Leukemia 27, 1107-1115, doi:leu2012341 [pii] 10.1038/leu.2012.341 (2013).

Alici, E. et al. Autologous antitumor activity by NK cells expanded from myeloma patients using GMP-compliant components. Blood 111, 3155-3162, doi:blood-2007-09-110312 [pii]10.1182/blood-2007-09-110312 (2008).

Barclay, A. N. & Van den Berg, T. K. The interaction between signal regulatory protein alpha (SIRPalpha) and CD47: structure, function, and therapeutic target. Annu Rev Immunol 32, 25-50, doi:10.1146/annurev-immunol-032713-120142 (2014).

Barclay, A. N. Signal regulatory protein alpha (SIRPalpha)/CD47 interaction and function. Curr Opin Immunol 21, 47-52, doi:S0952-7915(09)00004-1 [pii] 10.1016/j.coi.2009.01.008 (2009).

Brennan, F. R. et al. Safety and immunotoxicity assessment of immunomodulatory monoclonal antibodies. MAbs 2, 233-255, doi:11782 [pii] (2010).

Chao, M. P. et al. Anti-CD47 antibody synergizes with rituximab to promote phagocytosis and eradicate non-Hodgkin lymphoma. Cell 142, 699-713, doi:S0092-8674(10)00892-5 [pii]10.1016/j.cell.2010.07.044 (2010).

Fleit, H. B., Wright, S. D. & Unkeless, J. C. Human neutrophil Fc gamma receptor distribution and structure. Proceedings of the National Academy of Sciences of the United States of America 79, 3275-3279 (1982).

Guilliams, M., Bruhns, P., Saeys, Y., Hammad, H. & Lambrecht, B. N. The function of Fcgamma receptors in dendritic cells and macrophages. Nat Rev Immunol 14, 94-108, doi:nri3582 [pii] 10.1038/nri3582 (2014).

Krupka, C. et al. CD33 target validation and sustained depletion of AML blasts in long-term cultures by the bispecific T-cell-engaging antibody AMG 330. Blood 123, 356-365, doi:blood-2013-08-523548 [pii] 10.1182/blood-2013-08-523548 (2014).

Larson, R. A. et al. Final report of the efficacy and safety of gemtuzumab ozogamicin (Mylotarg) in patients with CD33-positive acute myeloid leukemia in first recurrence. Cancer 104, 1442-1452, doi:10.1002/cncr.21326 (2005).

Majeti, R. et al. CD47 is an adverse prognostic factor and therapeutic antibody target on human acute myeloid leukemia stem cells. Cell 138, 286-299, doi:S0092-8674(09)00650-3 [pii] 10.1016/j.cell.2009.05.045 (2009).

Pardoll, D. M. The blockade of immune checkpoints in cancer immunotherapy. Nat Rev Cancer 12, 252-264, doi:nrc3239 [pii] 10.1038/nrc3239 (2012).

Petersdorf, S. H. et al. A phase 3 study of gemtuzumab ozogamicin during induction and postconsolidation therapy in younger patients with acute myeloid leukemia. Blood 121, 4854-4860, doi:blood-2013-01-466706 [pii] 10.1182/blood-2013-01-466706 (2013).

Weiskopf, K. et al. Engineered SIRPalpha variants as immunotherapeutic adjuvants to anticancer antibodies. Science 341, 88-91, doi:science.1238856 [pii]10.1126/science.1238856 (2013).

Willingham, S. B. et al. The CD47-signal regulatory protein alpha (SIRPα) interaction is a therapeutic target for human solid tumors. Proc Natl Acad Sci USA 109, 6662-6667, doi:1121623109 [pii] 10.1073/pnas.1121623109 (2012).

Wines, B. D. et al. The IgG Fc contains distinct Fc receptor (FcR) binding sites: the leukocyte receptors Fc gamma RI and Fc gamma RIIa bind to a region in the Fc distinct from that recognized by neonatal FcR and protein A. J Immunol. 164(10), 5313-5318 (2000).

The invention claimed is:
1. A trispecific protein comprising:
(i) a first domain, wherein said first domain is formed by a Fab domain that specifically binds to a cell surface molecule at the cell surface of a tumor cell, wherein said cell surface molecule at the cell surface of the tumor cell is CD33, wherein the first domain comprises light chain CDR1 having an amino acid sequence of RASESLDNYGIRFLT (SEQ ID NO: 29), light chain CDR2 having an amino acid sequence of AASNQGS (SEQ ID NO: 30), light chain CDR3 having an amino acid sequence of QQTKEVPWS (SEQ ID NO: 31), heavy chain CDR1 having an amino acid sequence of DSNIH (SEQ ID NO: 32), heavy chain CDR2 having an amino acid sequence of YIYPYNGGT-DYNQKFKN (SEQ ID NO: 33), and heavy chain CDR3 having an amino acid sequence of GNPWLAY (SEQ ID NO: 34);
(ii) a second domain, wherein said second domain is formed by an IgG Fc domain and specifically binds to a cell surface molecule at the cell surface of an immune cell/immune cells; and
(iii) a third domain, wherein said third domain is formed by one or more SirpIg domains that specifically bind to a checkpoint molecule at the cell surface of said tumor cell, wherein said checkpoint molecule at the cell surface of said tumor cell is CD47, wherein said third domain is formed by an immunoglobulin-like domain of SIRPα (signal regulatory protein alpha),
and wherein said trispecific protein does not comprise any other part of said immune cell checkpoint receptor besides said immunoglobulin-like domain of SIRPα;
wherein two copies of the first domain and the second domain form an IgG and wherein the third domain is fused on its C-terminus to the N-terminus of each first domain by a flexible linker;
wherein the flexible linker comprises two to eight tandem repeats, each tandem repeat consisting of four or five amino acids with the amino acid sequence GGGS (SEQ ID NO: 6 or GGGGS (SEQ ID NO: 14).

2. The trispecific protein according to claim 1, wherein said tumor cell is an acute myeloid leukemia (AML) cell.

3. The trispecific protein according to claim 1,
wherein said trispecific protein further comprises a fourth domain, wherein said fourth domain specifically binds to a cell surface molecule at the cell surface of said tumor cell;
and/or said trispecific protein further comprises a second copy of said third domain.

4. The trispecific protein, according to claim 1, wherein the affinity of said first domain for said cell surface molecule at the cell surface of said tumor cell is higher than the affinity of said third domain for said checkpoint molecule by at least a factor of 10, when the affinity is measured by flow cytometry.

5. The trispecific protein, according to claim 1, wherein the affinity of said first domain for said cell surface molecule at the cell surface of said tumor cell is within the range of from 1 to 50 nM; and
the affinity of said third domain for said checkpoint molecule is within the range of from 500 nM to 3 µM, when the affinity is measured by flow cytometry.

6. The trispecific protein, according to claim 1, wherein the first domain comprises the sequence of SEQ ID NO: 4.

7. The trispecific protein, according to claim 1, wherein the first domain comprises the sequence of SEQ ID NO: 5.

8. The trispecific protein, according to claim 1, wherein the first domain comprises the sequences of SEQ ID NOs: 4 and 5.

9. The trispecific protein, according to claim 1, wherein the third domain comprises the sequence of SEQ ID NO: 1.

10. A pharmaceutical composition comprising the trispecific protein according to claim 1, and a pharmaceutically acceptable carrier.

* * * * *

SEQUENCE LISTING

<160> NUMBER OF SEQ ID NOS: 34

<210> SEQ ID NO 1

<211> LENGTH: 334
<212> TYPE: PRT
<213> ORGANISM: Artificial Sequence
<220> FEATURE:
<223> OTHER INFORMATION: Sirp-Ig

<400> SEQUENCE: 1

```
Gly Leu Gly Leu Gly Leu Leu Glu Gly Leu Asn Val Ala Leu Ile Leu
1               5                   10                  15

Glu Gly Leu Asn Pro Arg Ala Ser Pro Leu Tyr Ser Ser Glu Arg Val
            20                  25                  30

Ala Leu Leu Glu Val Ala Leu Ala Leu Ala Leu Ala Gly Leu Tyr
        35                  40                  45

Gly Leu Thr His Arg Ala Leu Ala Thr His Arg Leu Glu Ala Arg Gly
    50                  55                  60

Cys Tyr Ser Thr His Arg Ala Leu Ala Thr His Arg Ser Glu Arg Leu
65                  70                  75                  80

Glu Ile Leu Glu Pro Arg Val Ala Leu Gly Leu Tyr Pro Arg Ile Leu
                85                  90                  95

Glu Gly Leu Asn Thr Arg Pro Pro His Glu Ala Arg Gly Gly Leu Tyr
            100                 105                 110

Ala Leu Ala Gly Leu Tyr Pro Arg Gly Leu Tyr Ala Arg Gly Gly Leu
        115                 120                 125

Leu Glu Ile Leu Glu Thr Tyr Arg Ala Ser Asn Gly Leu Asn Leu Tyr
    130                 135                 140

Ser Gly Leu Gly Leu Tyr His Ile Ser Pro His Glu Pro Arg Ala Arg
145                 150                 155                 160

Gly Val Ala Leu Thr His Arg Thr His Arg Val Ala Leu Ser Glu Arg
                165                 170                 175

Ala Ser Pro Leu Glu Thr His Arg Leu Tyr Ser Ala Arg Gly Ala Ser
            180                 185                 190

Asn Ala Ser Asn Met Glu Thr Ala Ser Pro Pro His Glu Ser Glu Arg
        195                 200                 205

Ile Leu Glu Ala Arg Gly Ile Leu Glu Gly Leu Tyr Ala Ser Asn Ile
    210                 215                 220

Leu Glu Thr His Arg Pro Arg Ala Leu Ala Ala Ser Pro Ala Leu Ala
225                 230                 235                 240

Gly Leu Tyr Thr His Arg Thr Tyr Arg Thr Tyr Arg Cys Tyr Ser Val
                245                 250                 255

Ala Leu Leu Tyr Ser Pro His Glu Ala Arg Gly Leu Tyr Ser Gly Leu
            260                 265                 270

Tyr Ser Glu Arg Pro Arg Ala Ser Pro Ala Ser Pro Val Ala Leu Gly
        275                 280                 285

Leu Pro His Glu Leu Tyr Ser Ser Glu Arg Gly Leu Tyr Ala Leu Ala
    290                 295                 300

Gly Leu Tyr Thr His Arg Gly Leu Leu Glu Ser Glu Arg Val Ala Leu
305                 310                 315                 320

Ala Arg Gly Ala Leu Ala Leu Tyr Ser Pro Arg Ser Glu Arg
                325                 330
```

<210> SEQ ID NO 2
<211> LENGTH: 118
<212> TYPE: PRT
<213> ORGANISM: Artificial Sequence
<220> FEATURE:
<223> OTHER INFORMATION: Vh CD16scFv

```
<400> SEQUENCE: 2

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ala
        115

<210> SEQ ID NO 3
<211> LENGTH: 111
<212> TYPE: PRT
<213> ORGANISM: Artificial Sequence
<220> FEATURE:
<223> OTHER INFORMATION: Vl CD16scFv

<400> SEQUENCE: 3

Asp Thr Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 4
<211> LENGTH: 111
<212> TYPE: PRT
<213> ORGANISM: Artificial Sequence
<220> FEATURE:
<223> OTHER INFORMATION: Vl CD33scFv

<400> SEQUENCE: 4

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60
```

```
Arg Phe Ser Gly Ser Gly Ser Gly Thr Glu Phe Thr Leu Thr Ile Ser
 65                  70                  75                  80

Ser Leu Gln Pro Asp Asp Phe Ala Thr Tyr Tyr Cys Gln Gln Thr Lys
                 85                  90                  95

Glu Val Pro Trp Ser Phe Gly Gln Gly Thr Lys Val Glu Val Lys
            100                 105                 110

<210> SEQ ID NO 5
<211> LENGTH: 116
<212> TYPE: PRT
<213> ORGANISM: Artificial Sequence
<220> FEATURE:
<223> OTHER INFORMATION: Vh CD33scFv

<400> SEQUENCE: 5

Glu Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Ile Thr Asp Ser
                 20                  25                  30

Asn Ile His Trp Val Arg Gln Ala Pro Gly Gln Ser Leu Glu Trp Ile
             35                  40                  45

Gly Tyr Ile Tyr Pro Tyr Asn Gly Gly Thr Asp Tyr Asn Gln Lys Phe
 50                  55                  60

Lys Asn Arg Ala Thr Leu Thr Val Asp Asn Pro Thr Asn Thr Ala Tyr
 65                  70                  75                  80

Met Glu Leu Ser Ser Leu Arg Ser Glu Asp Thr Ala Phe Tyr Tyr Cys
                 85                  90                  95

Val Asn Gly Asn Pro Trp Leu Ala Tyr Trp Gly Gln Gly Thr Leu Val
            100                 105                 110

Thr Val Ser Ser
        115

<210> SEQ ID NO 6
<211> LENGTH: 4
<212> TYPE: PRT
<213> ORGANISM: Artificial Sequence
<220> FEATURE:
<223> OTHER INFORMATION: Linker sequence

<400> SEQUENCE: 6

Gly Gly Gly Ser
 1

<210> SEQ ID NO 7
<211> LENGTH: 8
<212> TYPE: PRT
<213> ORGANISM: Artificial Sequence
<220> FEATURE:
<223> OTHER INFORMATION: Linker sequence

<400> SEQUENCE: 7

Gly Gly Gly Ser Gly Gly Gly Ser
 1               5

<210> SEQ ID NO 8
<211> LENGTH: 12
<212> TYPE: PRT
<213> ORGANISM: Artificial Sequence
<220> FEATURE:
<223> OTHER INFORMATION: Linker sequence

<400> SEQUENCE: 8
```

Gly Gly Gly Ser Gly Gly Gly Ser Gly Gly Gly Ser
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Linker sequence

<400> SEQUENCE: 9

Gly Gly Gly Ser Gly Gly Gly Ser Gly Gly Gly Ser Gly Gly Gly Ser
1               5                   10                  15

<210> SEQ ID NO 10
<211> LENGTH: 20
<212> TYPE: PRT
<213> ORGANISM: Artificial Sequence
<220> FEATURE:
<223> OTHER INFORMATION: Linker sequence

<400> SEQUENCE: 10

Gly Gly Gly Ser Gly Gly Gly Ser Gly Gly Gly Ser Gly Gly Gly Ser
1               5                   10                  15

Gly Gly Gly Ser
            20

<210> SEQ ID NO 11
<211> LENGTH: 24
<212> TYPE: PRT
<213> ORGANISM: Artificial Sequence
<220> FEATURE:
<223> OTHER INFORMATION: Linker sequence

<400> SEQUENCE: 11

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 12
<211> LENGTH: 28
<212> TYPE: PRT
<213> ORGANISM: Artificial Sequence
<220> FEATURE:
<223> OTHER INFORMATION: Linker sequence

<400> SEQUENCE: 12

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser
            20                  25

<210> SEQ ID NO 13
<211> LENGTH: 32
<212> TYPE: PRT
<213> ORGANISM: Artificial Sequence
<220> FEATURE:
<223> OTHER INFORMATION: Linker sequence

<400> SEQUENCE: 13

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

<210> SEQ ID NO 14
<211> LENGTH: 5
<212> TYPE: PRT
<213> ORGANISM: Artificial Sequence
<220> FEATURE:
<223> OTHER INFORMATION: Linker sequence

<400> SEQUENCE: 14

Gly Gly Gly Gly Ser
1               5

<210> SEQ ID NO 15
<211> LENGTH: 10
<212> TYPE: PRT
<213> ORGANISM: Artificial Sequence
<220> FEATURE:
<223> OTHER INFORMATION: Linker sequence

<400> SEQUENCE: 15

Gly Gly Gly Gly Ser Gly Gly Gly Gly Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Linker sequence

<400> SEQUENCE: 16

Gly Gly Gly Gly Ser Gly Gly Gly Gly Ser Gly Gly Gly Gly Ser
1               5                   10                  15

<210> SEQ ID NO 17
<211> LENGTH: 20
<212> TYPE: PRT
<213> ORGANISM: Artificial Sequence
<220> FEATURE:
<223> OTHER INFORMATION: Linker sequence

<400> SEQUENCE: 17

Gly Gly Gly Gly Ser Gly Gly Gly Gly Ser Gly Gly Gly Gly Ser Gly
1               5                   10                  15

Gly Gly Gly Ser
            20

<210> SEQ ID NO 18
<211> LENGTH: 25
<212> TYPE: PRT
<213> ORGANISM: Artificial Sequence
<220> FEATURE:
<223> OTHER INFORMATION: Linker sequence

<400> SEQUENCE: 18

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 19
<211> LENGTH: 30
<212> TYPE: PRT
<213> ORGANISM: Artificial Sequence
<220> FEATURE:
<223> OTHER INFORMATION: Linker sequence

<400> SEQUENCE: 19

Gly Gly Gly Gly Ser Gly Gly Gly Gly Ser Gly Gly Gly Gly Ser Gly
1               5                   10                  15

Gly Gly Gly Ser Gly Gly Gly Ser Gly Gly Gly Ser
            20                  25                  30

<210> SEQ ID NO 20
<211> LENGTH: 35
<212> TYPE: PRT
<213> ORGANISM: Artificial Sequence
<220> FEATURE:
<223> OTHER INFORMATION: Linker sequence

<400> SEQUENCE: 20

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 21
<211> LENGTH: 40
<212> TYPE: PRT
<213> ORGANISM: Artificial Sequence
<220> FEATURE:
<223> OTHER INFORMATION: Linker sequence

<400> SEQUENCE: 21

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser Gly Gly
            20                  25                  30

Gly Gly Ser Gly Gly Gly Gly Ser
        35                  40

<210> SEQ ID NO 22
<211> LENGTH: 330
<212> TYPE: PRT
<213> ORGANISM: Artificial Sequence
<220> FEATURE:
<223> OTHER INFORMATION: Sequence constant region IgG1 format (CH1,
      hinge, CH2, CH3) wildtype

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 23
<211> LENGTH: 105
<212> TYPE: PRT
<213> ORGANISM: Artificial Sequence
<220> FEATURE:
<223> OTHER INFORMATION: Sequence constant region of the light chain
      (CL)

<400> SEQUENCE: 23

Val Ala Ala Pro Ser Val Phe Ile Phe Pro Pro Ser Asp Glu Gln Leu
1               5                   10                  15
Lys Ser Gly Thr Ala Ser Val Val Cys Leu Leu Asn Asn Phe Tyr Pro
            20                  25                  30
Arg Glu Ala Lys Val Gln Trp Lys Val Asp Asn Ala Leu Gln Ser Gly
        35                  40                  45
Asn Ser Gln Glu Ser Val Thr Glu Gln Asp Ser Lys Asp Ser Thr Tyr
    50                  55                  60
Ser Leu Ser Ser Thr Leu Thr Leu Ser Lys Ala Asp Tyr Glu Lys His
65                  70                  75                  80
Lys Val Tyr Ala Cys Glu Val Thr His Gln Gly Leu Ser Ser Pro Val
                85                  90                  95
Thr Lys Ser Phe Asn Arg Gly Glu Cys
            100                 105

<210> SEQ ID NO 24
<211> LENGTH: 330
<212> TYPE: PRT
<213> ORGANISM: Artificial Sequence
```

<220> FEATURE:
<223> OTHER INFORMATION: Sequence constant region IgG1 format (CH1, hinge, CH2, CH3) with mutations S239D and I332E, Fc-engineered

<400> SEQUENCE: 24

| | | | | | | | | | | | | | |
|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Lys | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Asp | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| | 130 | | | | | 135 | | | | | 140 | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | 195 | | | | | 200 | | | | | 205 | | | |
| Lys | Ala | Leu | Pro | Ala | Pro | Glu | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

<210> SEQ ID NO 25
<211> LENGTH: 117
<212> TYPE: PRT
<213> ORGANISM: Artificial Sequence
<220> FEATURE:
<223> OTHER INFORMATION: PD1ex

<400> SEQUENCE: 25

```
Asn Pro Pro Thr Phe Ser Pro Ala Leu Leu Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Cys Arg Phe Arg
50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
            85                  90                  95

Ala Pro Lys Ala Gln Ile Lys Glu Ser Leu Arg Ala Glu Leu Arg Val
            100                 105                 110

Thr Glu Arg Arg Ala
        115
```

<210> SEQ ID NO 26
<211> LENGTH: 108
<212> TYPE: PRT
<213> ORGANISM: Artificial Sequence
<220> FEATURE:
<223> OTHER INFORMATION: Vl PDL1scFv

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
            85                  90                  95

Thr Phe Gly Gln Gly Thr Lys Val Glu Ile Lys Arg
            100                 105
```

<210> SEQ ID NO 27
<211> LENGTH: 118
<212> TYPE: PRT
<213> ORGANISM: Artificial Sequence
<220> FEATURE:
<223> OTHER INFORMATION: Vh PDL1scFv

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 28
<211> LENGTH: 246
<212> TYPE: PRT
<213> ORGANISM: Artificial Sequence
<220> FEATURE:
<223> OTHER INFORMATION: Vl PDL1scFv + linker + Vh PDL1scFv

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Gly Gly Gly Gly Ser
        115                 120                 125

Glu Val Gln Leu Val Glu Ser Gly Gly Gly Leu Val Gln Pro Gly Gly
        130                 135                 140

Ser Leu Arg Leu Ser Cys Ala Ala Ser Gly Phe Thr Phe Ser Asp Ser
145                 150                 155                 160

Trp Ile His Trp Val Arg Gln Ala Pro Gly Lys Gly Leu Glu Trp Val
                165                 170                 175

Ala Trp Ile Ser Pro Tyr Gly Gly Ser Thr Tyr Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ala Arg Arg His Trp Pro Gly Gly Phe Asp Tyr Trp Gly Gln Gly Thr
225                 230                 235                 240

Leu Val Thr Val Ser Ala
                245

<210> SEQ ID NO 29
<211> LENGTH: 15
<212> TYPE: PRT
<213> ORGANISM: Artificial Sequence
<220> FEATURE:
<223> OTHER INFORMATION: light chain CDR1

<400> SEQUENCE: 29

Arg Ala Ser Glu Ser Leu Asp Asn Tyr Gly Ile Arg Phe Leu Thr
```

```
<210> SEQ ID NO 30
<211> LENGTH: 7
<212> TYPE: PRT
<213> ORGANISM: Artificial Sequence
<220> FEATURE:
<223> OTHER INFORMATION: light chain CDR2

<400> SEQUENCE: 30

Ala Ala Ser Asn Gln Gly Ser
1               5

<210> SEQ ID NO 31
<211> LENGTH: 9
<212> TYPE: PRT
<213> ORGANISM: Artificial Sequence
<220> FEATURE:
<223> OTHER INFORMATION: light chain CDR3

<400> SEQUENCE: 31

Gln Gln Thr Lys Glu Val Pro Trp Ser
1               5

<210> SEQ ID NO 32
<211> LENGTH: 5
<212> TYPE: PRT
<213> ORGANISM: Artificial Sequence
<220> FEATURE:
<223> OTHER INFORMATION: heavy chain CDR1

<400> SEQUENCE: 32

Asp Ser Asn Ile His
1               5

<210> SEQ ID NO 33
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 33

Tyr Ile Tyr Pro Tyr Asn Gly Gly Thr Asp Tyr Asn Gln Lys Phe Lys
1               5                   10                  15

Asn

<210> SEQ ID NO 34
<211> LENGTH: 7
<212> TYPE: PRT
<213> ORGANISM: Artificial Sequence
<220> FEATURE:
<223> OTHER INFORMATION: heavy chain CDR3

<400> SEQUENCE: 34

Gly Asn Pro Trp Leu Ala Tyr
1               5
```